(12) United States Patent
Lewis et al.

(10) Patent No.: US 7,521,228 B2
(45) Date of Patent: Apr. 21, 2009

(54) SPIDER SILK PROTEIN ENCODING NUCLEIC ACIDS, POLYPEPTIDES, ANTIBODIES AND METHODS OF USE THEREOF

(75) Inventors: Randolph V. Lewis, Laramie, WY (US);
Cheryl Y. Hayashi, Riverside, CA (US);
John E. Gatesy, Riverside, CA (US);
Dagmara Motriuk, Laramie, WY (US)

(73) Assignee: The University of Wyoming, Laramie, WY (US)

( * ) Notice: Subject to any disclaimer, the term of this patent is extended or adjusted under 35 U.S.C. 154(b) by 239 days.

(21) Appl. No.: 10/488,056

(22) PCT Filed: Mar. 28, 2002

(86) PCT No.: PCT/US02/09663

§ 371 (c)(1),
(2), (4) Date: Jul. 22, 2004

(87) PCT Pub. No.: WO03/020916

PCT Pub. Date: Mar. 13, 2003

(65) Prior Publication Data

US 2005/0010035 A1    Jan. 13, 2005

Related U.S. Application Data

(60) Provisional application No. 60/315,529, filed on Aug. 29, 2001.

(51) Int. Cl.
*C12N 15/00* (2006.01)
*C07K 14/00* (2006.01)
*C07H 21/02* (2006.01)

(52) U.S. Cl. .......... 435/320.1; 435/252.3; 435/352; 530/350; 530/300; 536/23.1

(58) Field of Classification Search .......... 530/350, 530/300; 536/23.1; 435/320.1, 325, 252.3
See application file for complete search history.

(56) References Cited

OTHER PUBLICATIONS

Beckwitt, R., et al., Sequence Conservation in the C-terminal Region of Spider Silk Proteins (Spidroin) from *Nephila clavipes* (Tetragnathidae) and *Araneus bicentenarius* (Araneidae), J. of Biol. Chem., vol. 269: pp. 6661-6663, (1994).
Gosline, J.M., et al., "The Mechanical Design of Spider Silks: From Fibroin Sequence to Mechanical Function", J. of Experimental Biol., vol. 202: pp. 3295-3303, (1999).
Hayashi, C.Y., et al., "Hypotheses that correlate the sequence, structure, and mechanical properties of spider silk proteins", International J. of Biological Macromolecules, vol. 24: pp. 271-275, (1999).
Hayashi, C.Y., et al., "Molecular Architecture and Evolution of a Modular Spider Silk Protein Gene", Science, vol. 287: pp. 1477-1479, (2000).
Xu, M., et al., "Structure of a protein superfiber: Spider dragline silk", Proc. Nat. Acad. Sci., USA., vol. 87: pp. 7120-7124, (1990).
Hinman, M.B., et al., "Isolation of a Clone Encoding a Second Dragline Silk Fibroin: *Nephila clavipes* Dragline Silk is a Two-Protein Fiber", J. of Biol. Chem., vol. 267: pp. 19320-19324, (1992).
Hayashi, C.Y., et al., "Evidence from Flagelliform Silk cDNA for the Structural Basis of Elasticity and Modular Nature of Spider Silks", J. Mol. Biol., vol. 275: pp. 773-784, (1998).
Colgin, M.A., et al., "Spider minor ampullate silk proteins contain new repetitive sequences and highly conserved non-silk-like "spacer regions"", Protein Science, vol. 7: 667-672, (1998).
Gatesy, J., et al., "Extreme Diversity, Conservation, and Convergence of Spider Silk Fibroin Sequences", Science, vol. 291: pp. 2603-2605, (2001).

*Primary Examiner*—Karen Cochrane Carlson
(74) *Attorney, Agent, or Firm*—Dann, Dorfman, Herrell and Skillman, P.C.; Patrick J. Hagan

(57) ABSTRACT

Spider silk protein encoding nucleic acids, polypeptides and antibodies immunologically specific therefore are disclosed. Methods of use thereof are also provided.

16 Claims, 3 Drawing Sheets

Figure 2

*Dolomedes* cDNA1
GGAGSGQGGYGNQGGLGGYGQGAGAGAAAAAAA

*Dolomedes* cDNA2
GGAGSGQGGYGGQGGLGGYGQGAGAGAAAAAAA

*Plectreurys* cDNA1
GAGAGAGAGAGAGAGSGASTSVSTSSSSGSGAGAGAGSGAGSGAGAGSGAGAGA
GAGGAGAGPGSGLGLGYGVGLSSAQAQAQAQAAAQAQAQAQAQAYAAAQAQAQAQAQ
AQAAAAAAAAAAA

*Plectreurys* cDNA2
TIAGLGYGRQGQGTDSSASSVSTSTSVSSSATGPDTGYPVGYYGAGQAEAAASAAAAAA
ASAAEAA

*Plectreurys* cDNA3
repeat type 1:
AISSSLYAPNYQASAASSAAAQSSAQTASTSAKQTAASTSASTAATSTTQTAATTSASTA
ASSQTVQKASTSSAASTAASKSQSSSVGSSTTSTAAASASSSYAPAQSLSQYLLSSQQFT
TAPASSTAVASSQQYAEAMAQSVATSLGLGYTYTSALSVAMAQAISGVGGGASAYSYAT
AISQAISRVLTSSGVSLSSSQATSVAS
repeat type 2:
SSQQSSYDTSSDLSSASSSAAAAAASASSYESQFSDASSSSNAAAAA

*Plectreurys* cDNA4
SQQGPIGGVGGSNAFSSSFASALSLNRGFTEVISSASATAVASAFQKGLAPYGTAFALSA
ASAAADAYNSIGSGANAFAYAQAFARVLYPLVRQYGLSSSAKASAFASAIASSFSSGTSG
QGPSIGQQQPPVTISAASASAGASAAAVGGGQVGQGPYGGQQQSTAASASAAAATATS
GGAQKQPSGESSVATASAAATSVTSAGAPVGKPGVPAPIFYPQGPLQQGPAPGPSNVQ
PGT

*Euagrus* cDNA
ASQIAASVASAVASSASAAAAAASSSAAAAGASSAAGAASSSSTTTTTSTSSSAAAAAAA
AAAASASGASSASAAAASASAAASAFSSALISDLLGIGVFGNTFGSIGSASAASSIASAAAQ
AALSGLGLSYLASAGASAVASAVAGVGVGAGAYAYAYAIANAFASILANTGLLSVSSAASV
ASSVASAIATSVSSSSAAAAASASAAAAASASASAASSASASSSASAAAAAGASAAAGAA
SSASASAAAASAFSSAFISDLLGFSQFNSVFGSITSSSLGLGIAANAVQSGLASLGLRAAAS
AAASAVANAGLNGSGAYAYATAIASAIGNALLGAGFLTAGN

Figure 3

MaSp1

```
Nep.c.*        GGA--GQGGYGGLGSQGA------GRGGLGGQ---GA--GAAAAAA---
Nep.m.†        GGA--GQGGYGGLGSQGA------GRGGYGGQ---GA--GAAAAAA---
Nep.s.†        GGA--GQGGYGGLGGQGA-------------------GAAAAAA---
Tet.k.†        GGLGGGQ-GAGQGGQQGAGQGGYGSGLGGAGQ-------GASAAAAAAAA
Tet.v.†        GGLGGGQGGY---------GSGLGGAGQGGQQGAGQGAAAAAASAAA
Lat.g.$^m$     GGA--GQGGY------GQ------GGQGGA-------GAAAAAAAAA-
Arg.a.†        GGQ-GGXGGYGGLGSQGAGQ-GYGSGLGGQGGAGQG---GAAAAAAAAAA
Arg.t.$^m$     GGQ-GGQGGYGGLGXQGAGQ-GYGAGSGGQGGXGQG---GAAAAAAAA--
Ara.d.*(ADF-2) GGQ-GGQGGQGGLGSQGAG----GAGQGGY-GAGQG---GAAAAAAAA--
```

MaSp2

```
Nep.c.*        ---GPG--QQGPGGYGPG---QQGPGGYGPGQQGPSGPGSAAAAAAAAA
Nep.m.1†       ---GPG--QQGPGGYGPG---QQGPGGYGPGQQGPSGPGSAAAAAAAA-
Nep.s.†        ---GPG--QQGPGXY----------GPSGPGSAAAAA---
Lat.g.$^{m,t}$ ---------GPGGYGPGPGXQQGY-------GPGGSGAAAAAAAA-
Arg.a.†        GGYGPGAGQQGPGSQGPGSGGQQGPGGX----GPYGPSAAAAAAAA-
Arg.t.1$^m$    GGYGPGAGQQGPGSQGPGSGGQQGPGGQ----GPYGPSAAAAAAAA-
Gas.m.†        GGYGPGSGQQGPGQQGPGSGGQQGPGGQ----GPYGPGAAAAAAAA-
Ara.b.*        GGYGPGSGQQGPGQQ-------GPGQQ----GPYGPGASAAAAAA-
Ara.d.1*(ADF-3)GGYGPGSGQQGPGQQ-------GPGGQ----GPYGPGASAAAAAA-
Nep.m.2†       -GRGPGGY--GPGQQ-------------GPGGPGAAAAAA---
Arg.t.2†       ---GPGGQ--GPGQQ-------GPGGYGPS--GPGGASAAAAAAAA-
Ara.d.2*(ADF-4)---GPGGY--GPGSQGPS----GPGAYGPG--GP-GSSAAAAAAAAS
```

MiSp

```
Nep.c.1*    [GAGGAGGYGR--GAGAGAGAAAGAGAGAGGYGGQGGYGAGAGAGAAAAAGA-]$_{10}$ [spacer]$_1$
Nep.c.2*    [----GGYGRGVGAGAGAGAAAGXGAGAGGYGGQGGYGAGXGA---AAAGAG]$_{10}$ [spacer]$_1$
Ara.d.*(ADF-1) [GAGAAGGYGG--GAGAGAG------GAGGY-GQ-GYGAGAGAGAAAAAGA-]$_5$ [spacer]$_1$
```

Flag

```
Nep.c.*   [GPGGX]$_{41}$ [GGX]$_7$ TIIEDLDITIDGADGPITISEELTIS--GAGGS [GPGGX$_n$]$_{25}$
Nep.m.*   [GPGGX]$_{36}$ [GGX]$_7$ TVIEDLDITIDGADGPITISEELTIGGAGAGGS [3PGGX$_n$]$_{19}$
Arg.t.$^§$ [GPGGX$_n$]$_6$  GPVTVDVDVSVGGAPGG [GPGGX$_n$]$_5$ [GGX]$_6$ [GPGGX$_n$]$_7$
```

SPIDER SILK PROTEIN ENCODING NUCLEIC ACIDS, POLYPEPTIDES, ANTIBODIES AND METHODS OF USE THEREOF

This application is a §371 application of PCT/US02/09663, filed Mar. 28, 2002, which in turn claims priority to U.S. Provisional Application 60/315,529 filed August 29, 2001, the entire disclosure of each of the above-identified applications being incorporated by reference herein.

Pursuant to 35 U.S.C. §202(c) it is acknowledged that the U.S. Government has certain rights in the invention described herein, which was made in part with funds from the National Science Foundation, Grant Number MCB-9806999.

FIELD OF THE INVENTION

This invention relates to the fields of molecular and cellular biology. Specifically, nucleic acids encoding spider silk polypeptides, spider silk polypeptides, spider silk polypeptide-specific antibodies, and methods of use thereof are provided.

BACKGROUND OF THE INVENTION

Several publications are referenced in this application by numerals in parentheses in order to more fully describe the state of the art to which this invention pertains. Full citations for these references are found at the end of the specification. The disclosure of each of these publications is incorporated by reference herein.

Spider silks comprise a model system for exploring the relationship between the amino acid composition of a protein, the structural properties that result from variations in the amino acid composition of a protein, and how such variations impact protein function. While silk production has evolved multiple times within arthropods, silk use is most highly developed in spiders. Spiders are unique in their lifelong ability to spin an array of different silk proteins (or fibroin proteins) and the degree to which they depend on this ability. There are over 34,000 described species of Araneae (1). Each species utilizes silk, and some ecribellate orb-weavers (Araneoidea) have a varied toolkit of task-specific silks with divergent mechanical properties (2). Araneoid major ampullate silk, the primary dragline, is extremely tough. Minor ampullate silk, used in web construction, has high tensile strength. An orb-web's capture spiral, in part composed of flagelliform silk, is elastic and can triple in length before breaking (3). Each of these fibers is composed of one or more proteins encoded by the spider silk fibroin gene family (4). Sequencing of araneoid fibroins has revealed that these fibroins are dominated by iterations of four simple amino acid motifs: poly-alanine ($A_n$), alternating glycine and alanine (GA), GGX (where X represents a small subset of amino acids), and $GPG(X)_n$ (5).

Spiders draw fibers from dissolved fibroin proteins that are stored in specialized sets of abdominal glands. Each type of silk is secreted and stored by a different abdominal gland until extruded by tiny spigots on the spinnerets. Spiders use fibroin proteins singly or in combination for a variety of different purposes, including: draglines, retreats, egg sacs, and prey-catching snares. Given these specialized applications, individual silks appear to have evolved to possess mechanical properties (e.g., tensile strength and flexibility) that optimize their utility for particular applications.

Orb web spiders like *Nephila* are known to produce spider silk proteins derived from several types of silk synthetic glands and are designated according to their organ of origin. Spider silk proteins known to exist include: major ampullate spider proteins (MaSp), minor ampullate spider proteins (MiSp), and flagelliform (Flag), tubuliform, aggregate, aciniform, and pyriform spider silk proteins. Spider silk proteins derived from each organ are generally distinguishable from those derived from other synthetic organs by virtue of their physical and chemical properties, which render them well suited to different uses. Tubuliform silk, for example, is used in the outer layers of egg-sacs, whereas aciniform silk is involved in wrapping prey and pyriform silk is laid down as the attachment disk.

Most molecular and structural investigations of spider silks have focused on dragline silk, which has an extraordinarily high tensile strength (e.g. Xu & Lewis, Proc. Natl. Acad. Sci., USA 87, 7120-7124, 1990; Hinman & Lewis, J. Biol. Chem. 267, 19320-19324, 1992; Thiel et al., Biopolymers 34, 1089-1097, 1994; Simmons et al., Science 271, 84-87, 1996; Kümmerlen et al., Macromol. 29, 2920-2928, 1996; and Osaki, Nature 384, 419, 1996). Dragline silk, often referred to as major ampullate silk because it is produced by the major ampullate glands, has a high tensile strength ($5\times10^9$ $Nm^{-2}$) similar to Kevlar ($4\times10^9$ $Nm^{-2}$) (Gosline et al., *Endeavour* 10, 37-43, 1986; Stauffer et al., *J. Arachnol.* 22, 5-11, 1994). In addition to this exceptional strength, dragline silk also exhibits substantial (~35%) elasticity (Gosline et al., Endeavour 10, 37-43, 1986). Thus a structure/function analysis of dragline silk is revealing in terms of the features of a protein which confer strength and elasticity.

Silk strength is widely attributed to crystalline beta-sheet structures. Such protein domains are found in both lepidopteran silks (e.g. *Bombyx mori*, Mita et al., *J. Mol. Evol.* 38, 583-592, 1994) and spider silks (Xu & Lewis, Proc. Natl. Acad. Sci., USA 87, 7120-7124, 1990; Hinman & Lewis, J. Biol. Chem. 267, 19320-19324, 1992; Gosline et al., *Endeavour* 10, 37-43, 1986). In contrast, elasticity is generally thought to involve amorphous regions (Wainwright et al., Mechanical design in organisms, Princeton University Press, Princeton, 1982). More precise characterization of these amorphous components can be revealed by molecular sequence data.

Based on the protein sequences of major ampullate silk proteins, a beta-turn structure was suggested to be the likely mechanism of elasticity (Hinman & Lewis, J. Biol. Chem. 267, 19320-19324, 1992). Assessing this proposition, however, was problematic because dragline silk is a hybrid of at least two distinct proteins which impart both strength and moderate elasticity.

*Nephila* minor ampullate silk can be distinguished from *Nephila* major ampullate silk by both physical and chemical properties. On a basic level, the amino acid composition of solubilized minor ampullate silk differs from that of solubilized major ampullate silk. Like the major ampullate silk proteins (major spidroin 1, MaSP1; major spidroin 2, MaSP2), the proteins comprising minor ampullate silk (minor spindroin 1, MiSP1; minor spindroin 2, MiSP2) have a primary structure dominated by imperfect repetition of a short sequence of amino acids. Moreover, in contrast to the elasticity exhibited by major ampullate silk, minor ampullate silk yields without recoil. Minor ampullate silk will stretch to about 25% of its initial length before breaking, thereby exhibiting a tensile strength of nearly 100,000 pounds per square inch (psi). The minor ampullate silk proteins, therefore, exhibit comparatively lower tensile strength and elasticity relative to major ampullate silk proteins.

The capture spiral, on the other hand, is formed from silk proteins derived from the flagelliform and aggregate silk glands. The capture spiral of an orb-web comprises a structure having significant ability to stretch, as would be anticipated for a structure that must capture and retain prey. The capture thread has a lower tensile strength ($1 \times 10^9$ $Nm^{-2}$) but several times the elasticity (>200%) of dragline silk (Vollrath & Edmonds, Nature 340, 305-307, 1989; Kohler & Vollrath, J. Exp. Zool. 271, 1-17, 1995). The flagelliform silk comprises the core fiber of the spiral, while aggregate silk provides a non-fibrous, aqueous coating. Thus, while aggregate silk is an integral part of the elastic capture spiral, it is flagelliform silk that provides the ability to stretch.

SUMMARY OF THE INVENTION

In view of the unique properties of different silks produced by spiders, the identification of novel spider silk proteins and characterization of their chemical and physical properties provide useful new reagents having utility for a number of applications. Spider silk proteins are unique in that they possess properties which include, but are not limited to, high tensile strength and elasticity. Moreover, individual spider silk proteins have evolved to possess different combinations of properties that contribute to the physical balance between protein strength and elasticity.

Spider silk is composed of fibers formed from proteins. Naturally occurring spider silk fibers can be composites of two or more proteins. In general, spider silk proteins are found to have primary amino acid sequences that can be characterized as indirect repeats of a short consensus sequence. Variation in the consensus sequence is then responsible for the distinguishable properties of different silk proteins.

Silk fibers can be made from synthetic polypeptides having amino acid sequences substantially similar to a consensus repeat unit of a silk protein or from polypeptides expressed from nucleic acid sequences encoding a natural or engineered silk protein, or derivative thereof. Depending on the application for which a synthetic spider silk protein is intended, it may also be desirable to form fibers from a single spider silk protein or combinations of different spider silk proteins, the ratio of which can be modified accordingly.

According to one aspect of the invention, nucleic acid sequences encoding novel spider silk-proteins are provided. Exemplary nucleic acid sequences of the invention have sequences comprising SEQ ID NOS: 1-28.

In a particular aspect of the invention, exemplary nucleic acid sequences encoding novel MaSp1-like spider silk proteins are provided. Exemplary nucleic acid sequences of this type have sequences comprising SEQ ID NOs: 1-7.

In another aspect of the invention, exemplary nucleic acid sequences encoding novel MaSp2-like spider silk proteins are provided. Exemplary nucleic acid sequences of this type have sequences comprising SEQ ID NOs: 8-16.

In another aspect of the invention, exemplary nucleic acid sequences encoding novel flagelliform (flag)-like spider silk proteins are provided. Exemplary nucleic acid sequences of this type have sequences comprising SEQ ID NOs: 17 and 18.

In another aspect of the invention, nucleic acid sequences encoding novel spider silk proteins are provided. Exemplary nucleic acid sequences of this type have sequences comprising SEQ ID NOs: 19 and 20.

In yet another aspect of the invention, nucleic acid sequences encoding novel spider silk proteins which comprise atypical repetitive motifs are provided. Exemplary nucleic acid sequences of this type have sequences comprising SEQ ID NOs: 21-27.

In a particular aspect of the invention, an isolated nucleic acid sequence which encodes a novel spider silk protein comprising atypical repetitive motifs is provided. An exemplary nucleic acid sequence of this type has a sequence comprising SEQ ID NO: 28.

In a preferred embodiment of the invention, the isolated nucleic acid molecules provided encode spider silk proteins. In a particularly preferred embodiment, spider silk proteins of the present invention have amino acid sequences comprising SEQ ID NOS: 29-56.

In a particular aspect of the invention, novel MaSp1-like spider silk proteins have amino acid sequences comprising SEQ ID NOs: 29-35.

In another aspect of the invention, novel MaSp2-like spider silk proteins have amino acid sequences comprising SEQ ID NOs: 36-44.

In another aspect of the invention, novel flag-like spider silk proteins have amino acid sequences comprising SEQ ID NOs: 45 and 46.

In another aspect of the invention, novel spider silk proteins have amino acid sequences comprising SEQ ID NOs: 47 and 48.

In yet another aspect of the invention, novel spider silk proteins comprising atypical repetitive motifs have amino acid sequences comprising SEQ ID NOs: 49-55.

In a particular aspect of the invention, a novel spider silk protein comprising atypical repetitive motifs is provided. An exemplary spider silk protein amino acid sequence of this type comprises SEQ ID NO: 56.

According to another aspect of the present invention, an isolated nucleic acid molecule is provided, which has a sequence selected from the group consisting of: (1) SEQ ID NOs: 1-28; (2) a sequence specifically hybridizing with preselected portions or all of an individual complementary strand of SEQ ID NOs: 1-28 comprising nucleic acids encoding amino acids of SEQ ID NOs: 29-56; (3) a sequence encoding preselected portions of SEQ ID NOs: 1-28, and (4) a sequence comprising nucleic acids encoding amino acids of a consensus sequence (SEQ ID NO: 57) which was derived from SEQ ID NO: 56.

Such partial sequences are useful as probes to identify and isolate homologues of spider silk protein genes of the invention. Additionally, isolated nucleic acid sequences encoding natural allelic variants of the nucleic acids of SEQ ID NOs: 1-28 are also contemplated to be within the scope of the present invention. The term natural allelic variants will be defined hereinbelow.

According to another aspect of the present invention, antibodies immunologically specific for the spider silk proteins described hereinabove are provided.

In yet another aspect of the invention, host cells comprising at least one of the spider silk protein encoding nucleic acids are provided. Such host cells include but are not limited to bacterial cells, fungal cells, insect cells, mammalian cells, and plant cells. Host cells overexpressing one or more of the spider silk protein encoding nucleic acids of the invention provide valuable reagents for many applications, including, but not limited to, production of silk fibers comprising at least one silk protein that can be incorporated into a material to modulate the structural properties of the material.

Naturally occurring spider silk proteins have an imperfectly repetitive structure. Imperfections in the repetition are likely to be a consequence of the process by which the silk protein genes evolved, rather than a requirement for fiber formation. Imperfections in repetition are thus not likely to affect properties of fibers formed following aggregation of protein molecules.

Accordingly, in another embodiment of the present invention nucleic acid sequences are provided which encode engineered spider silk proteins, each of which comprises a polypeptide having direct repeats of a unit amino acid sequence. Alternatively, nucleic acid sequences may include several different unit amino acid sequences to form a "copolymer" silk protein.

In yet another embodiment of the present invention a spider silk protein expressed from a nucleic acid sequence is provided, wherein the nucleic acid sequence is obtained from cDNA, genomic DNA, synthetic DNA, or fragments of all of the above, derived from a spider ampullate gland.

In another embodiment of the present invention fibers made from silk protein obtained by expression of nucleic acid sequences encoding at least one spider silk protein are provided.

BRIEF DESCRIPTION OF THE DRAWINGS

FIG. 2 shows consensus ensemble repeat units for non-araneoid spider fibroins. Single letter symbols for amino acids are used, and GGX, GA, and $A_n$ motifs are indicated in green, brown, and red, respectively. *Plectreurys* cDNA1 and *Plectreurys* cDNA2 were derived from the larger ampule-shaped glands of *Plectreurys*, and *Plectreurys* cDNA3 and *Plectreurys* cDNA4 were from the smaller ampullate glands of this spider.

FIG. 3 shows consensus ensemble repeat units for four araneoid fibroin orthologue groups. Single letter symbols for amino acids are used, and GGX, GA, $A_n$, and $GPG(X)_n$ motifs are indicated in green, brown, red, and blue, respectively. The "[spacer]" region of the MiSp fibroins is a serine-rich sequence that is 137 amino acids long in *Nephila clavipes* (Genbank #AF027735). Nep.c.=*Nephila clavipes*, Nep.m.=*N. madagascariensis*, Nep.s.=*N. senegalensis*, Tet.k.=*Tetragnatha kauaiensis*, Tet.v.=*T. versicolor*, Lat.g.=*Latrodectus geometricus*, Arg.t.=*Argiope trifasciata*, Arg.a.=*A. aurantia*, Ara.b.=*Araneus bicentenarius*, Ara.d.=*A. diadematus*, Gas.m.=*Gasteracantha mammosa*. §m=cDNA from major ampullate glands, §f=cDNA from flagelliform glands, †=PCR/genomic clone, *=previously published sequence. The previous designations for *A. diadematus* fibroins (4) are shown in parentheses (ADF1-4).

DETAILED DESCRIPTION OF THE INVENTION

Figure 1:
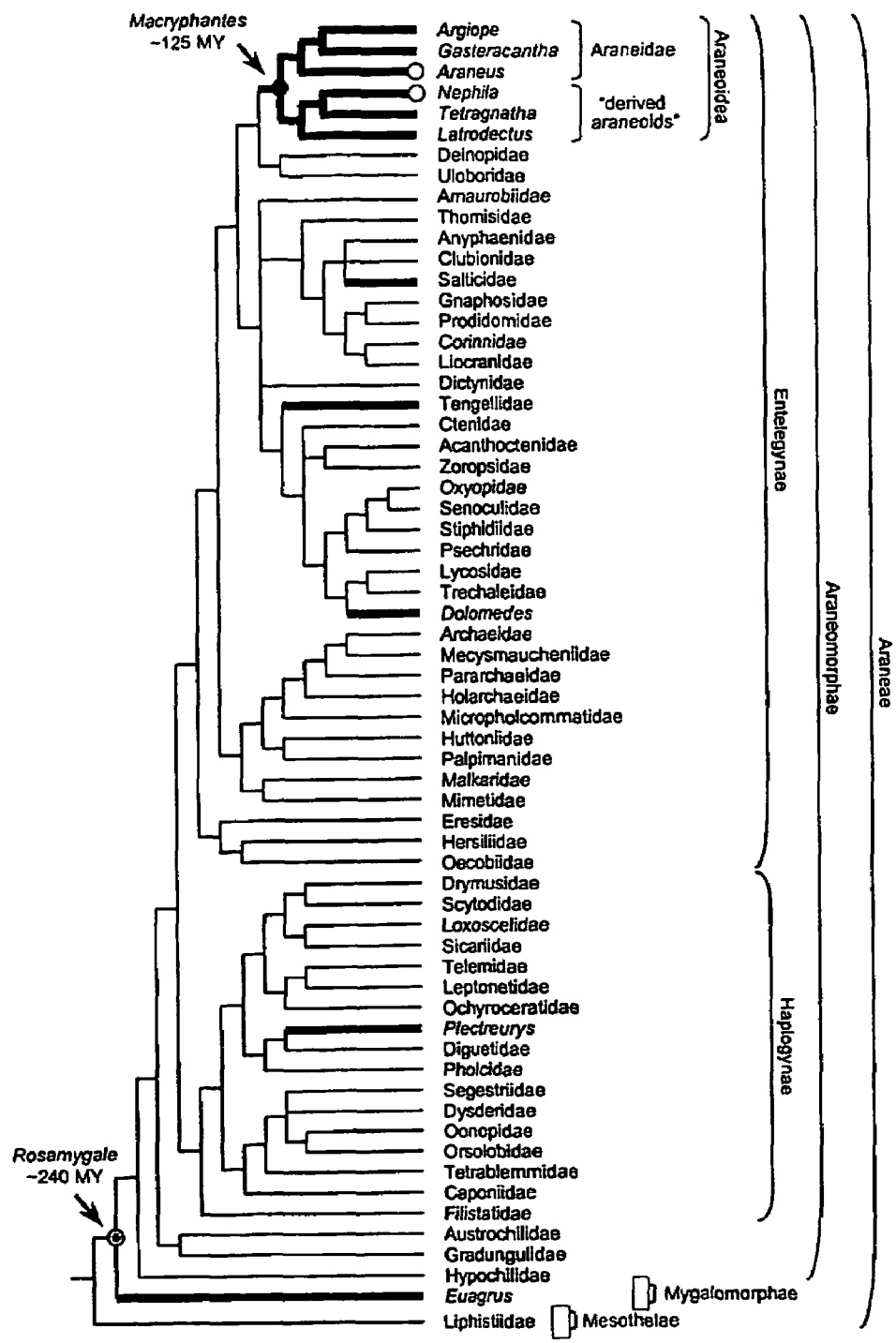
FIG. 1 shows an analysis of phylogenetic relationships of Araneae based on morphological evidence (1,27). Previously published spider fibroin sequences are from the two genera marked by white circles. Including data presented herein, fibroin sequences have been characterized for the taxa in red. Circles at internal nodes mark fossil calibration points. Extinct taxa that calibrate these nodes, *Macryphantes* (16—black circle) and *Rosamygale* (13—gray circle), are indicated, and higher level taxa are to the right of brackets. *Dolomedes, Plectreurys*, and *Euagrus* are from the families Pisauridae, Plectreuridae, and Dipluridae, respectively.

The physical characteristics of spider silk proteins confer unparalleled mechanical properties to these fibroins and, thus, render spider silk proteins ideally suited to a variety of applications. Identification of novel spider silk proteins as described herein, therefore, provides useful tools for the generation of natural and synthetic spider silk proteins which can be woven into fibers to imbue fibers comprised of such proteins with unique properties.

In a preferred embodiment of the invention, nucleic acid sequences encoding novel spider silk proteins have sequences comprising SEQ ID NOS: 1-28.

In a particularly preferred embodiment, spider silk proteins of the present invention have amino acid sequences comprising SEQ ID NOS: 29-56.

In yet another preferred embodiment, a consensus sequence derived from SEQ ID NO: 56 has amino acid sequences comprising SEQ ID NO: 57.

Other spider silk proteins have been previously identified, see for example U.S. Pat. Nos. 5,773,771; 5,989,894; and 5,728,810, the entire disclosures of which are incorporated herein by reference.

I. Definitions

The following definitions are provided to facilitate an understanding of the present invention:

With reference to nucleic acids used in the invention, the term "isolated nucleic acid" is sometimes employed. This term, when applied to DNA, refers to a DNA molecule that is separated from sequences with which it is immediately contiguous (in the 5' and 3' directions) in the naturally occurring genome of the organism from which it was derived. For example, the "isolated nucleic acid" may comprise a DNA molecule inserted into a vector, such as a plasmid or virus vector, or integrated into the genomic DNA of a procaryote or eucaryote. An "isolated nucleic acid molecule" may also comprise a cDNA molecule. An isolated nucleic acid molecule inserted into a vector is also sometimes referred to herein as a recombinant nucleic acid molecule.

With respect to RNA molecules, the term "isolated nucleic acid" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form.

With respect to single stranded nucleic acids, particularly oligonucleotides, the term "specifically hybridizing" refers to the association between two single-stranded nucleotide molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence. Appropriate conditions enabling specific hybridization of single stranded nucleic acid molecules of varying complementarity are well known in the art.

For instance, one common formula for calculating the stringency conditions required to achieve hybridization between nucleic acid molecules of a specified sequence homology is set forth below (Sambrook et al., 1989):

$$T_m = 81.5° C. + 16.6 \text{ Log [Na+]} + 0.41(\% \, G+C) - 0.63(\% \text{ formamide}) - 600/\#bp \text{ in duplex}$$

As an illustration of the above formula, using [Na+]=[0.368] and 50% formamide, with GC content of 42% and an average probe size of 200 bases, the $T_m$ is 57°C. The $T_m$ of a DNA duplex decreases by 1-1.5° C. with every 1% decrease in homology. Thus, targets with greater than about 75% sequence identity would be observed using a hybridization temperature of 42°C.

The term "oligonucleotide," as used herein refers to primers and probes of the present invention, and is defined as a nucleic acid molecule comprised of two or more ribo- or deoxyribonucleotides, preferably more than three. The exact size of the oligonucleotide will depend on various factors and on the particular application and use of the oligonucleotide. Preferred oligonucleotides comprise 15-50 consecutive bases of SEQ ID Nos: 1-28.

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and use of the method. For example, depending on the complexity of the target sequence, the oligonucleotide probe typically contains 15-25 or more nucleotides, although it may contain fewer nucleotides. The probes herein are selected to be complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield a primer extension product. The primer may vary in length depending on the particular conditions and requirement of the application. For example, in diagnostic applications, the oligonucleotide primer is typically 15-25 or more nucleotides in length. The primer must be of sufficient complementarity to the desired template to prime the synthesis of the desired extension product, that is, to be able to anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

Polymerase chain reaction (PCR) has been described in U.S. Pat. Nos. 4,683,195, 4,800,195, and 4,965,188, the entire disclosures of which are incorporated by reference herein.

Amino acid residues described herein are preferred to be in the "L" isomeric form. However, residues in the "D" isomeric form may be substituted for any L-amino acid residue, provided the desired properties of the polypeptide are retained. All amino-acid residue sequences represented herein conform to the conventional left-to-right amino-terminus to carboxy-terminus orientation.

Amino acid residues are identified in the present application according to the three-letter or one-letter abbreviations in the following Table:

TABLE 1

| Amino Acid | 3-letter Abbreviation | 1-letter Abbreviation |
|---|---|---|
| L-Alanine | Ala | A |
| L-Arginine | Arg | R |
| L-Asparagine | Asn | N |
| L-Aspartic Acid | Asp | D |
| L-Cysteine | Cys | C |
| L-Glutamine | Gln | Q |
| L-Glutamic Acid | Glu | E |
| Glycine | Gly | G |
| L-Histidine | His | H |
| L-Isoleucine | Ile | I |
| L-Leucine | Leu | L |
| L-Methionine | Met | M |
| L-Phenylalanine | Phe | F |
| L-Proline | Pro | P |
| L-Serine | Ser | S |
| L-Threonine | Thr | T |
| L-Tryptophan | Trp | W |
| L-Tyrosine | Tyr | Y |
| L-Valine | Val | V |
| L-Lysine | Lys | K |

The term "isolated protein" or "isolated and purified protein" is sometimes used herein. This term refers primarily to a protein produced by expression of an isolated nucleic acid molecule of the invention. Alternatively, this term may refer to a protein that has been sufficiently separated from other proteins with which it would naturally be associated, so as to exist in "substantially pure" form. "Isolated" is not meant to exclude artificial or synthetic mixtures with other compounds or materials, or the presence of impurities that do not interfere with the fundamental activity, and that may be present, for example, due to incomplete purification, addition of stabilizers, or compounding into, for example, immunogenic preparations or pharmaceutically acceptable preparations.

"Mature protein" or "mature polypeptide" shall mean a polypeptide possessing the sequence of the polypeptide after any processing events that normally occur to the polypeptide during the course of its genesis, such as proteolytic processing from a polyprotein precursor. In designating the sequence or boundaries of a mature protein, the first amino acid of the mature protein sequence is designated as amino acid residue 1. As used herein, any amino acid residues associated with a mature protein not naturally found associated with that protein that precedes amino acid 1 are designated amino acid −1, −2, −3 and so on. For recombinant expression systems, a methionine initiator codon is often utilized for purposes of efficient translation. This methionine residue in the resulting polypeptide, as used herein, would be positioned at −1 relative to the mature protein sequence.

A low molecular weight "peptide analog" shall mean a natural or mutant (mutated) analog of a protein, comprising a linear or discontinuous series of fragments of that protein and which may have one or more amino acids replaced with other amino acids and which has altered, enhanced or diminished biological activity when compared with the parent or nonmutated protein.

The term "biological activity" is a function or set of functions performed by a molecule in a biological context (i.e., in an organism or an in vitro surrogate or facsimile model). For spider silk proteins, biological activity is characterized by physical properties (e.g., tensile strength and elasticity) as described herein.

The term "substantially pure" refers to a preparation comprising at least 50-60% by weight the compound of interest (e.g., nucleic acid, oligonucleotide, polypeptide, protein, etc.). More preferably, the preparation comprises at least 75% by weight, and most preferably 90-99% by weight, the compound of interest. Purity is measured by methods appropriate for the compound of interest (e.g. chromatographic methods, agarose or polyacrylamide gel electrophoresis, HPLC analysis, mass spectrometry and the like).

The term "tag," "tag sequence" or "protein tag" refers to a chemical moiety, either a nucleotide, oligonucleotide, polynucleotide or an amino acid, peptide or protein or other chemical, that when added to another sequence, provides additional utility or confers useful properties, particularly in the detection or isolation, of that sequence. Thus, for example, a homopolymer nucleic acid sequence or a nucleic acid sequence complementary to a capture oligonucleotide may be added to a primer or probe sequence to facilitate the subsequent isolation of an extension product or hybridized product. In the case of protein tags, histidine residues (e.g., 4 to 8 consecutive histidine residues) may be added to either the amino- or carboxy-terminus of a protein to facilitate protein isolation by chelating metal chromatography. Alternatively, amino acid sequences, peptides, proteins or fusion partners representing epitopes or binding determinants reactive with specific antibody molecules or other molecules (e.g., flag epitope, c-myc epitope, transmembrane epitope of the influenza A virus hemaglutinin protein, protein A, cellulose binding domain, calmodulin binding protein, maltose binding protein, chitin binding domain, glutathione S-transferase, and the like) may be added to proteins to facilitate protein isolation by procedures such as affinity or immunoaffinity chromatography. Chemical tag moieties include such molecules as biotin, which may be added to either nucleic acids or proteins, and facilitates isolation or detection by interaction with avidin reagents, and the like. Numerous other tag moieties are known to, and can be envisioned by the trained artisan, and are contemplated to be within the scope of this definition.

A "vector" is a replicon, such as a plasmid, cosmid, bacmid, phage or virus, to which another genetic sequence or element (either DNA or RNA) may be attached so as to bring about the replication of the attached sequence or element. An "expression vector" is a specialized vector that contains a gene with the necessary regulatory regions needed for expression in a host cell.

The term "operably linked" means that the regulatory sequences necessary for expression of the coding sequence are placed in the DNA molecule in the appropriate positions relative to the coding sequence so as to effect expression of the coding sequence. This same definition is sometimes applied to the arrangement of coding sequences and transcription control elements (e.g. promoters, enhancers, and termination elements) in an expression vector. This definition is also sometimes applied to the arrangement of nucleic acid sequences of a first and a second nucleic acid molecule wherein a hybrid nucleic acid molecule is generated.

The phrase "consisting essentially of" when referring to a particular nucleotide or amino acid means a sequence having the properties of a given SEQ ID NO:. For example, when used in reference to an amino acid sequence, the phrase includes the sequence per se and molecular modifications that would not affect the basic and novel characteristics of the sequence.

A "clone" or "clonal cell population" is a population of cells derived from a single cell or common ancestor by mitosis.

A "cell line" is a clone of a primary cell or cell population that is capable of stable growth in vitro for many generations.

An "immune response" signifies any reaction produced by an antigen, such as a viral antigen, in a host having a functioning immune system. Immune responses may be either humoral in nature, that is, involve production of immunoglobulins or antibodies, or cellular in nature, involving various types of B and T lymphocytes, dendritic cells, macrophages, antigen presenting cells and the like, or both. Immune responses may also involve the production or elaboration of various effector molecules such as cytokines, lymphokines and the like. Immune responses may be measured both in in vitro and in various cellular or animal systems. Such immune responses may be important in protecting the host from disease and may be used prophylactically and therapeutically.

An "antibody" or "antibody molecule" is any immunoglobulin, including antibodies and fragments thereof, that binds to a specific antigen. The term includes polyclonal, monoclonal, chimeric, and bispecific antibodies. As used herein, antibody or antibody molecule contemplates both an intact immunoglobulin molecule and an immunologically active portion of an immunoglobulin molecule such as those portions known in the art as Fab, Fab', F(ab')2 and F(v).

With respect to antibodies, the term "immunologically specific" refers to antibodies that bind to one or more epitopes of a protein or compound of interest, but which do not substantially recognize and bind other molecules in a sample containing a mixed population of antigenic biological molecules.

"Natural allelic variants", "mutants" and "derivatives" of particular sequences of nucleic acids refer to nucleic acid sequences that are closely related to a particular sequence but which may possess, either naturally or by design, changes in sequence or structure. By closely related, it is meant that at least about 75%, but often, more than 90%, of the nucleotides of the sequence match over the defined length of the nucleic acid sequence referred to using a specific SEQ ID NO. Changes or differences in nucleotide sequence between closely related nucleic acid sequences may represent nucleotide changes in the sequence that arise during the course of normal replication or duplication in nature of the particular nucleic acid sequence. Other changes may be specifically designed and introduced into the sequence for specific purposes, such as to change an amino acid codon or sequence in a regulatory region of the nucleic acid. Such specific changes may be made in vitro using a variety of mutagenesis techniques or produced in a host organism placed under particular selection conditions that induce or select for the changes. Such sequence variants generated specifically may be referred to as "mutants" or "derivatives" of the original sequence.

A "derivative" of a spider silk protein or a fragment thereof means a polypeptide modified by varying the amino acid sequence of the protein, e.g. by manipulation of the nucleic acid encoding the protein or by altering the protein itself. Such derivatives of the natural amino acid sequence may involve insertion, addition, deletion or substitution of one or more amino acids, and may or may not alter the essential activity of original the spider silk protein.

As mentioned above, the spider silk polypeptide or protein of the invention includes any analogue, fragment, derivative or mutant which is derived from a spider silk protein and which retains at least one property or other characteristic of a spider silk protein. Different "variants" of spider silk proteins exist in nature. These variants may be alleles characterized by differences in the nucleotide sequences of the gene coding for the protein, or may involve different RNA processing or post-translational modifications. The skilled person can produce variants having single or multiple amino acid substitutions, deletions, additions or replacements. These variants may include inter alia: (a) variants in which one or more amino acids residues are substituted with conservative or non-conservative amino acids, (b) variants in which one or more amino acids are added to a spider silk protein, (c) variants in which one or more amino acids include a substituent group, and (d) variants in which a spider silk protein or fragment thereof is fused with another peptide or polypeptide such as a fusion partner, a protein tag or other chemical moiety, that may confer useful properties to a spider silk protein, such as, for example, an epitope for an antibody, a polyhistidine sequence, a biotin moiety and the like. Other spider silk proteins of the invention include variants in which amino acid residues from one species are substituted for the corresponding residue in another species, either at the conserved or non-conserved positions. In another embodiment, amino acid residues at non-conserved positions are substituted with conservative or non-conservative residues. The techniques for obtaining these variants, including genetic (suppressions, deletions, mutations, etc.), chemical, and enzymatic techniques are known to the person having ordinary skill in the art.

To the extent such allelic variations, analogues, fragments, derivatives, mutants, and modifications, including alternative nucleic acid processing forms and alternative post-translational modification forms result in derivatives of spider silk protein that retain any of the biological properties of a spider silk protein, they are included within the scope of this invention.

The term "functional" as used herein implies that the nucleic or amino acid sequence is functional for the recited assay or purpose.

A "unit repeat" constitutes a repetitive short sequence. Thus, the primary structure of the spider silk proteins is considered to consist mostly of a series of small variations of a unit repeat. The unit repeats in the naturally occurring proteins are often distinct from each other. That is, there is little or no exact duplication of the unit repeats along the length of the protein. Synthetic spider silks, however, can be made wherein the primary structure of the protein comprises a number of exact repetitions of a single unit repeat. Additional synthetic spider silks can be synthesized which comprise a number of repetitions of one unit repeat together with a number of repetitions of a second unit repeat. Such a structure would be similar to a typical block copolymer. Unit repeats of several different sequences can also be combined to provide a synthetic spider silk protein having properties suited to a particular application.

The term "direct repeat" as used herein is a repeat in tandem (head-to-tail arrangement) with a similar repeat.

II. Preparation of Spider Silk-Encoding Nucleic Acid Molecules. Spider Silk Proteins, and Antibodies Thereto A. Nucleic Acid Molecules Nucleic acid molecules encoding the polypeptides of the invention may be prepared by two general methods: (1) synthesis from appropriate nucleotide triphosphates, or (2) isolation from biological sources. Both methods utilize protocols well known in the art. The availability of nucleotide sequence information, such as the DNA sequences encoding a spider silk protein, enables preparation of an isolated nucleic acid molecule of the invention by oligonucleotide synthesis. Synthetic oligonucleotides may be prepared by the phosphoramidite method employed in the Applied Biosystems 38A DNA Synthesizer or similar devices. The resultant construct may be used directly or purified according to methods known in the art, such as high performance liquid chromatography (HPLC).

Specific probes for identifying such sequences as a spider silk protein encoding sequence may be between 15 and 40 nucleotides in length. For probes longer than those described above, the additional contiguous nucleotides are provided within sequences encoding a spider silk protein.

In accordance with the present invention, nucleic acids having the appropriate level of sequence homology with sequences encoding a spider silk protein may be identified by using hybridization and washing conditions of appropriate stringency. For example, hybridizations may be performed, according to the method of Sambrook et al., *Molecular Cloning*, Cold Spring Harbor Laboratory (1989), using a hybridization solution comprising: 5×SSC, 5×Denhardt's reagent, 1.0% SDS, 100 µg/ml denatured, fragmented salmon sperm DNA, 0.05% sodium pyrophosphate and up to 50% formamide. Hybridization is carried out at 37-42°C. for at least six hours. Following hybridization, filters are washed as follows: (1) 5 minutes at room temperature in 2×SSC and 1% SDS; (2) 15 minutes at room temperature in 2×SSC and 0.1% SDS; (3) 30 minutes-1 hour at 37°C. in 1×SSC and 1% SDS; (4) 2 hours at 42-65° C. in 1×SSC and 1% SDS, changing the solution every 30 minutes.

The nucleic acid molecules described herein include cDNA, genomic DNA, RNA, and fragments thereof which may be single- or double-stranded. Thus, oligonucleotides are provided having sequences capable of hybridizing with at least one sequence of a nucleic acid sequence, such as selected segments of sequences encoding a spider silk protein. Also contemplated in the scope of the present invention are methods of use for oligonucleotide probes which specifically hybridize with DNA from sequences encoding a spider silk protein under high stringency conditions. Primers capable of specifically amplifying sequences encoding a spider silk protein are also provided. As mentioned previously, such oligonucleotides are useful as primers for detecting, isolating and amplifying sequences encoding a spider silk protein.

Antisense nucleic acid molecules which may be targeted to translation initiation sites and/or splice sites to inhibit the expression of spider silk protein genes or production of their encoded proteins are also provided. Such antisense molecules are typically between 15 and 30 nucleotides in length and often span the translational start site of a spider silk protein mRNA molecule.

B. Proteins

Full-length spider silk proteins of the present invention may be prepared in a variety of ways, according to known methods. The proteins may be purified from appropriate sources, e.g., transformed bacterial or animal cultured cells or tissues, by immunoaffinity purification. However, this is not a preferred method due to the low levels of protein likely to be present in a given cell type at any time. The availability of nucleic acid molecules encoding spider silk proteins enables production of the proteins using in vitro expression methods known in the art. For example, a cDNA or gene may be cloned into an appropriate in vitro transcription vector, such as pSP64 or pSP65 for in vitro transcription, followed by cell-free translation in a suitable cell-free translation system, such as wheat germ or rabbit reticulocytes. In vitro transcription and translation systems are commercially available, e.g., from Promega Biotech, Madison, Wis. or Gibco-BRL, Gaithersburg, Md.

Alternatively, according to a preferred embodiment, larger quantities of spider silk protein may be produced by expression in a suitable prokaryotic or eukaryotic system. For example, part or all of at least one DNA molecule, such as nucleic acid sequences having a sequence selected from the group of SEQ ID NOs: 1-28 may be inserted into a plasmid vector adapted for expression in a bacterial cell, such as $E.$ $coli.$ Such vectors comprise the regulatory elements necessary for expression of the DNA in the host cell positioned in such a manner as to permit expression of the DNA in the host cell. Such regulatory elements required for expression include promoter sequences, transcription initiation sequences and, optionally, enhancer sequences.

The spider silk proteins produced by gene expression in a recombinant prokaryotic or eukaryotic system may be purified according to methods known in the art. In a preferred embodiment, a commercially available expression/secretion system can be used, whereby the recombinant protein is expressed and thereafter secreted from the host cell, to be easily purified from the surrounding medium. If expression/secretion vectors are not used, an alternative approach involves purifying the recombinant protein from cell lysates (remains of cells following disruption of cellular integrity) derived from prokaryotic or eukaryotic cells in which a protein was expressed. Methods for generation of such cell lysates are known to those of skill in the art. Recombinant protein can be purified by affinity separation, such as by immunological interaction with antibodies that bind specifically to the recombinant protein or nickel columns for isolation of recombinant proteins tagged with 6-8 histidine residues at their N-terminus or C-terminus. Alternative tags may comprise the FLAG epitope or the hemagglutinin epitope. Such methods are commonly used by skilled practitioners.

The spider silk proteins of the invention, prepared by the aforementioned methods, may be analyzed according to standard procedures. For example, such proteins may be subjected to amino acid sequence analysis, according to known methods.

A protein produced according to the present invention can be chemically modified after synthesis of the polypeptide. The presence of several carboxylic acid side chains (Asp or Glu) in the spacer regions facilitates the attachment of a variety of different chemical groups to silk proteins including amino acids having such side chains. The simplest and easiest procedure is to use a water-soluble carbo-diimide to attach the modifying group via a primary amine. If the group to be attached has no primary amine, a variety of linking agents can be attached via their own primary amines and then the modifying group attached via an available chemistry. Jennes, L. and Stumpf, W. E. Neuroendocrine Peptide Methodology, Chapter 42. P. Michael Conn, editor. Academic Press, 1989.

Desirable chemical modifications include, but are not limited to, derivatization with peptides that bind to cells, e.g. fibroblasts, derivatization with antibiotics and derivatization with cross-linking agents so that cross-linked fibers can be made. The selection of derivatizing agents for a particular purpose is within the skill of the ordinary practitioner of the art.

Exemplary Methods for Generation of Spider Silk Proteins

In view of the unique properties of spider silk proteins, special considerations should be applied to the generation of synthetic spider silk proteins. The repetitive nature of amino acid sequences encoding these proteins may render synthesis of a full length spider silk protein, or fragments thereof, technically challenging. To facilitate production of full length silk protein molecules, the following protocol is provided.

The polypeptides of the present invention can be made by direct synthesis or by expression from cloned DNA. Means for expressing cloned DNA are set forth above and are generally known in the art. The following considerations are recommended for the design of expression vectors used to express DNA encoding the spider silk proteins of the present invention.

First, since spider silk proteins are highly repetitive in their structure, cloned DNA should be propagated and expressed in host cell strains that can maintain repetitive sequences in extrachromosomal elements (e.g. SURE™ cells, Stratagene). The prevalence of specific amino acids (e.g., alanine, glycine, proline, and glutamine) also suggests that it might be advantageous to use a host cell that overexpresses tRNA for these amino acids.

The proteins of the present invention can otherwise be expressed using vectors providing for high level transcription, fusion proteins allowing affinity purification through an epitope tag, and the like. The hosts can be either bacterial or eukaryotic cells. Eukaryotic cells such as yeast, especially *Saccharomyces cerevisisae*, or insect cells might be particularly useful eukaryotic hosts. Expression of an engineered minor ampullate silk protein is described in U.S. Pat. No. 5,756,677, herein incorporated by reference. Such an approach can be used to express proteins of the present invention.

A useful spider silk protein or fragment thereof may be (1) insoluble inside a cell in which it is expressed or (2) capable of being formed into an insoluble fiber under normal conditions by which fibers are made. Preferably, the protein is insoluble under conditions (1) and (2). Specifically, the protein or fragment may be insoluble in a solvent such as water, alcohol (methanol, ethanol, etc.), acetone and/or organic acids, etc. The spider silk protein or fragment thereof should be capable of being formed into a fiber having high tensile strength, e.g., a tensile strength of 0.5x to 2x wherein x is the tensile strength of a fiber formed from a corresponding natural silk or whole protein. A spider silk protein or fragment thereof should also be capable of being formed into a fiber possessing high elasticity, e.g., at least 15%, more preferably about 25%.

Variants of a spider silk protein may be formed into a fiber having a tensile strength and/or elasticity which is greater than that of the natural spider silk or natural protein. The elasticity may be increased up to 100%. Variants may also possess properties of protein fragments.

A fragment or variant may have substantially the same characteristics as a natural spider silk. The natural protein may be particularly insoluble when in fiber form and resistant to degradation by most enzymes.

Recombinant spider silk proteins may be recovered from cultures by lysing cells to release spider silk proteins expressed therein. Initially, cell debris can be separated by centrifugation. Clarified cell lysate comprised of debris and supernatant can then be repeatedly extracted with solvents in which spider silk proteins are insoluble, but cellular debris is soluble. A differential solubilization process such as described above can be used to facilitate isolation of a purified spider silk protein precipitate. These procedures can be repeated and combined with other procedures including filtration, dialysis and/or chromatography to obtain a pure product.

Fibrillar aggregates will form from solutions by spontaneous self-assembly of spider silk proteins when the protein concentration exceeds a critical value. The aggregates can be gathered and mechanically spun into macroscopic fibers according to the method of O'Brien et al. [I. O'Brien et al., "Design, Synthesis and Fabrication of Novel Self-Assembling Fibrillar Proteins", in Silk Polymers: *Materials Science and Biotechnology*, pp. 104-117, Kaplan, Adams, Farmer and Viney, eds., c. 1994 by American Chemical Society, Washington, D.C.].

Exemplary Methods for Preparation of Fibers From Spider Silk Proteins

As noted above, the spider silk proteins can be viewed as derivatized polyamides. Accordingly, methods for producing fiber from soluble spider silk proteins are similar to those used to produce typical polyamide fibers, e.g. nylons, and the like.

O'Brien et al. supra describe fiber production from adenovirus fiber proteins. In a typical fiber production, spider silk proteins can be solubilized in a strongly polar solvent. The protein concentration of such a protein solution should typically be greater than 5% and is preferably between 8 and 20%.

Fibers should preferably be spun from solutions having properties characteristic of a liquid crystal phase. The fiber concentration at which phase transition can occur is dependent on the polypeptide composition of a protein or combination of proteins present in the solution. Phase transition, however, can be detected by monitoring the clarity and birefringence of the solution. Onset of a liquid crystal phase can be detected when the solution acquires a translucent appearance and registers birefringence when viewed through crossed polarizing filters.

The solvent used to dissolve a spider silk protein should be polar, and is preferably highly polar. Such solvents are exemplified by di- and tri-haloacetic acids, and haloalcohols (e.g. hexafluoroisopropanol). In some instances, co-solvents such as acetone are useful. Solutions of chaotropic agents, such as lithium thiocyanate, guanidine thiocyanate or urea can also be used.

In one fiber-forming technique, fibers can first be extruded from the protein solution through an orifice into methanol, until a length sufficient to be picked up by a mechanical means is produced. Then a fiber can be pulled by such mechanical means through a methanol solution, collected, and dried. Methods for drawing fibers are considered well-known in the art. For example, fibers made from a 58 kDa synthetic MaSp consensus polypeptide were drawn by methods similar to those used for drawing low molecular weight nylons. Such methods are described in U.S. Pat. No. 5,994,099, the entirety of which is incorporated herein by reference.

Of note, spider silk proteins of the present invention have primary structures dominated by imperfect repetition of a short sequence of amino acids. A "unit repeat" constitutes one such short sequence. Thus, the primary structure of a spider silk protein can be thought to consist mostly of a series of small variations of a unit repeat. Unit repeats in a naturally occurring protein are often distinct from each other. In other words, there is little or no exact duplication of a unit repeat along the length of a protein. Synthetic spider silks, however, can be generated wherein the primary structure of a synthetic spider silk protein can be described as a number of exact repetitions of a single unit repeat. Additional synthetic spider silks can be described as a number of repetitions of one unit repeat together with a number of repetitions of a second unit repeat. Such a structure would be similar to a typical block copolymer. The present invention also encompasses generation of synthetic spider silk proteins comprising unit repeats derived from several different spider silk sequences (naturally occurring variants or genetically engineered variants thereof).

Such synthetic hybrid spider silk proteins may each have 900 to 2700 amino acids with 25 to 100, preferably 30 to 90 repeats. A spider silk or fragment or variant thereof usually has a molecular weight of at least about 16,000 daltons, preferably 16,000 to 150,000 daltons, more preferably 50,000 to 120,000 daltons for fragments and greater than 100,000 but less than 500,000 daltons, preferably 120,000 to 350,000 for a full length protein.

C. Antibodies

The present invention also provides antibodies capable of immunospecifically binding to proteins of the invention. Polyclonal antibodies directed toward a spider silk protein may be prepared according to standard methods. In a preferred embodiment, monoclonal antibodies are prepared, which react immunospecifically with various epitopes of the spider silk proteins described herein. Monoclonal antibodies may be prepared according to general methods of Köhler and Milstein, following standard protocols. Polyclonal or monoclonal antibodies that immunospecifically interact with spider silk proteins can be utilized for identifying and purifying such proteins. For example, antibodies may be utilized for affinity separation of proteins with which they immunospecifically interact. Antibodies may also be used to immunoprecipitate proteins from a sample containing a mixture of proteins and other biological molecules. Other uses of anti-spider silk protein antibodies are described below.

III. Uses of Spider Silk-Encoding Nucleic Acids, Spider Silk Proteins and Antibodies Thereto A. Spider Silk-Encoding Nucleic Acids Spider silk protein-encoding nucleic acids may be used for a variety of purposes in accordance with the present invention. Spider silk protein-encoding DNA, RNA, or fragments thereof may be used as probes to detect the presence of and/or expression of genes encoding spider silk proteins. Methods in which spider silk protein-encoding nucleic acids may be utilized as probes for such assays include, but are not limited to: (1) in situ hybridization; (2) Southern hybridization; (3) northern hybridization; and (4) assorted amplification reactions such as polymerase chain reactions (PCR).

The spider silk protein-encoding nucleic acids of the invention may also be utilized as probes to identify related genes from other animal species. As is well known in the art, hybridization stringencies may be adjusted to allow hybridization of nucleic acid probes with complementary sequences of varying degrees of homology. Thus, spider silk protein-encoding nucleic acids may be used to advantage to identify and characterize other genes of varying degrees of relation to the spider silk protein genes of the invention. Such information enables further characterization of nucleic acid sequences which encode proteins that possess physical properties typical of spider silk proteins and thus facilitate structure/function analysis of such proteins. Additionally, they may be used to identify genes encoding proteins that interact with spider silk proteins (e.g., by the "interaction trap" technique), which should further accelerate identification of other components utilized in webs comprised of spider silk proteins. Moreover, interacting proteins identified in such screens maybe of utility in the generation and/or optimization of materials comprised of synthetic spider silk proteins. Spider silk protein encoding nucleic acids may also be used to generate primer sets suitable for PCR amplification of target spider silk protein DNA. Criteria for selecting suitable primers are well known to those of ordinary skill in the art.

Host cells comprising at least one spider silk protein encoding DNA molecule are encompassed in the present invention. Host cells contemplated for use in the present invention include but are not limited to bacterial cells, fungal cells, insect cells, mammalian cells, and plant cells. The spider silk protein encoding DNA molecules may be introduced singly into such host cells or in combination to assess the phenotype of cells conferred by such expression. Methods for introducing DNA molecules are also well known to those of ordinary skill in the art. Such methods are set forth in Ausubel et al. eds., *Current Protocols in Molecular Biology*, John Wiley & Sons, NY, N.Y. 1995, the disclosure of which is incorporated by reference herein.

As described above, spider silk protein-encoding nucleic acids are also used to advantage to produce large quantities of substantially pure spider silk proteins, or selected portions thereof.

B. Proteins and Antibodies

Purified spider silk protein, or fragments thereof, produced by methods of the present invention can be used to advantage in a variety of different applications, including, but not limited to, production of fabric, sutures, medical coverings, high-tech clothing, rope, reinforced plastics, and other applications in which various combinations of strength and elasticity are required.

TABLE II lists physical properties of various biological and manmade materials

| Material | Material Strength (N m$^{-2}$) | Elasticity (%) | Energy to Break (J kg$^{-1}$) |
| --- | --- | --- | --- |
| Dragline Silk | $4 \times 10^9$ | 35 | $1 \times 10^5$ |
| Minor Silk | $1 \times 10^9$ | 5 | $3 \times 10^4$ |
| Flagelliform Silk | $1 \times 10^9$ | 200+ | $1 \times 10^5$ |
| KEVLAR | $4 \times 10^9$ | 5 | $3 \times 10^4$ |
| Rubber | $1 \times 10^9$ | 600 | $8 \times 10^4$ |
| Tendon | $1 \times 10^9$ | 5 | $5 \times 10^3$ |

As shown in Table II, spider silks are characterized by advantageous physical properties, including, but not limited to, high tensile strength and pronounced elasticity, that are highly desirable for numerous applications. It is significant to note that spider silks possess these physical properties in aggregation which renders them unique proteins having unparalleled utility. For example, spider dragline silk has a tensile strength greater than steel or carbon fibers (200 ksi), elasticity as great as some nylon (35%), a stiffness as low as silk (0.6 msi), and the ability to supercontract in water (up to 60% decrease in length). In view of its high tensile strength and elasticity, the energy required to break dragline silk exceeds that required to break any known fiber including Kelvar™ and steel. These properties are unmatched by any known natural or manmade material. Moreover, the new materials of the present invention would also provide unique combinations of such desirable features in a very low weight material.

In view of the foregoing advantageous properties, use of the spider silk proteins disclosed in the present invention as components in materials would produce superior products. When spider silk is dissolved in an appropriate solvent and forced through a small orifice to generate spider silk fibers, such fibers can be woven into a fabric/material or added into a composite fabric/material. For example, spider silk fibers can be woven into fabrics to modulate the strength and elasticity of a fabric, thus rendering materials comprising such modified fabric optimized for different applications. Spider silk fibers can be of particular utility when incorporated into materials used to make high-tech clothing, rope, sails, parachutes, wings on aerial devices (e.g., hang gliders), flexible tie downs for electrical components, sutures, and even as a biomaterial for implantation (e.g., artificial ligaments or aortic banding). Biomedical applications involve use of natural and/or synthetic spider silk fibers of the present invention in sutures used in surgical procedures, including, but not limited to: eye surgery, reconstructive surgery (e.g., nerve or tympanic membrane reconstruction), vascular closure, bowel surgery, cosmetic surgery, and central nervous system surgery. Natural and synthetic spider silk fibers may also be of utility in the generation of antibiotic impregnated sutures and implant material and matrix material for reconstruction of bone and connective tissue. Implants and matrix material for reconstruction may be impregnated with aggregated growth factors, differentiation factors, and/or cell attractants to facilitate incorporation of the exogenous material and optimize recovery of a patient. Spider silk proteins and fibers of the present invention can be used for any application in which various combinations of strength and elasticity are required. Moreover, spider silk proteins can be modified to optimize their utility in any application. As described above, sequences of spider silk proteins can be modified to alter various physical properties of a fibroin and different spider silk proteins and variants thereof can be woven in combination to produce fibers comprised of at least one spider silk protein or variant thereof.

In a preliminary study designed to evaluate the potential for an immune response to a natural spider silk protein, natural dragline silk was implanted into mice and rats intramuscularly, intraperitoneally, or subcutaneously. Animals into which natural dragline silk was introduced did not mount an immune response to the spider silk protein, irrespective of the site of implantation. Of note, tissue sections surrounding spider silk protein implants were essentially identical to tissue sections derived from implantation sites into which a polyethylene rod was inserted. Since a polyethylene rod was used as the solid matrix about which the dragline spider silk protein was wrapped prior to implantation, introduction of a polyethylene rod alone serves as a negative control for the experiment. In view of the above, spider silk proteins of the present invention are expected to elicit minimal immunological responses when introduced into vertebrate animals.

Synthetic spider silk fibers are of utility in any application for which natural spider silk fibers can be used. For example, synthetic fibers may be mixed with various plastics and/or resins to prepare a fiber-reinforced plastic and/or resin product. Because spider silk is stable up to 180° C., spider silk protein fibers would be of utility as structural reinforcement material in thermal injected plastics.

It should be apparent from the foregoing that the spider silk proteins of the present invention and derivatives thereof can be generated in large quantities by means generally known to those of skill in the art. Spider silk proteins and derivatives thereof can be made into fibers for any intended use. Moreover, mixed composites of fibers are also of interest as a consequence of their unique combined properties. Such mixed composites can confer characteristics of flexibility and strength to any material into which they can be incorporated.

Purified spider silk protein, or fragments' thereof, may be used to produce polyclonal or monoclonal antibodies which also may serve as sensitive detection reagents for the presence and accumulation of a spider silk protein (or complexes containing spider silk protein) in cells. Recombinant techniques enable expression of fusion proteins containing part or all of a spider silk protein. The full length protein or fragments of the protein may be used to advantage to generate an array of monoclonal antibodies specific for various epitopes of a spider silk protein, thereby providing even greater sensitivity for detection of a spider silk protein in cells.

Polyclonal or monoclonal antibodies immunologically specific for a spider silk protein may be used in a variety of assays designed to detect and quantitate these proteins. Such assays include, but are not limited to: (1) flow cytometric analysis; and (2) immunoblot analysis (e.g., dot blot, Western blot) of extracts from various cells. Additionally, anti-spider silk protein antibodies can be used for purification of a spider silk protein and any associated subunits (e.g., affinity column purification, immunoprecipitation).

From the foregoing discussion, it can be seen that spider silk-encoding nucleic acids, spider silk expressing vectors, spider silk and anti-spider silk antibodies of the invention can be used separately or in combination, for example, 1) to identify nucleic acid sequences encoding other spider silk proteins or proteins comprising similar motifs, 2) generate novel hybrid spider silk proteins selected for optimization of different physical properties, 3) to express large quantities of spider silk proteins or fragments or derivatives thereof, and 4) to detect expression of spider silk proteins in cells and/or organisms.

The following examples are provided to illustrate an embodiment of the invention. They are not intended to limit the scope of the invention in any way.

EXAMPLE I

Identification of Clones Encoding Spider Silk Proteins

In order to identify novel spider silk proteins and expand the limited database of nucleic acid sequences encoding fibroin proteins, eleven cDNA libraries derived from silk glands of seven spider genera were generated. cDNA data were supplemented by information from two genomic libraries and PCR-amplified sequences (7). Partial cDNA or gene sequences for 28 fibroins from seven families of Araneae were identified. The data, as described herein, greatly extend the phylogenetic diversity of characterized fibroins (FIG. 1).

Methods for Collection of Sequence Data cDNA libraries were made from major ampullate glands of *Argiope trifasciata* (Araneidae) and *Lactrodectus geometricus* (Theridiidae), flagelliform glands of *A. trifasciata*, ampullate glands of *Dolomedes tenebrosus* (Pisauridae), two sets of silk glands from *Plectreurys tristis* (Plectreuridae), and silk glands of the mygalomorph *Euagrus chisoseus* (Dipluridae). Glands from *Dolomedes* were the four pairs of spindly ampullate glands with long tails that are connected to the spinnerets via extensive looped ducts. Glands from *Plectreurys* were the two largest pairs of ampule-shaped glands. The relatively uniform silk glands of *Euagrus* were combined in the RNA extraction for this species. Genomic libraries were constructed for *Nephila madagascariensis* (Tetragnathidae) and for *A. trifasciata*. Data from the thirteen libraries were augmented by PCR amplified genomic sequences from eight araneoids.

All the silk glands from *Phidippus audax* (Salticidae) were combined in the RNA extraction for this species. Similarly, all the silk glands from *Zorocrates* sp. (Zorocratidae) were combined in the RNA extraction for this species. Separate cDNA libraries were made from the aciniform glands connected to the median spinnerets and aciniform glands connected to the posterior spinnerets of *Argiope trifasciata* (Araneidae). Identical cDNA sequences for an aciniform fibroin were isolated from both libraries.

Procedures for construction and screening of the seven cDNA libraries were as follows. Silk glands were dissected from euthanized spiders and flash-frozen in liquid nitrogen. mRNA was extracted from the glands using Dynabeads Oligo (dT)25 (Dynal). cDNA was synthesized using the SuperScript Choice System (Life Technologies) with oligo(dT) as the first-strand synthesis primer. Size-fractionated cDNAs (ChromaSpin-1000, Clontech) were ligated into either pGEM-3zf(+)(Promega) and electroporated into SURE cells (Stratagene), pZErO®-2 cells (Invitrogen) or TOP10 cells (Invitrogen). Eleven libraries of ~1500 recombinant colonies each were constructed, and colonies were replicated onto nylon membranes for screening.

Silk cDNA clones were identified by sequential hybridizations (QuikHyb, Stratagene) with the $\gamma^{32}$P-labeled probes CCWAYWCCNCCATATCCWCC (SEQ ID NO: 58), CCWCCWGGWCCNNNWCCWCCWGGWCC (SEQ ID NO: 59), CCWGGWCCTTGTTGWCCWGGWCC (SEQ ID NO: 60), GCDGCDGCDGCDGCDGC (SEQ ID NO: 61), CCWGCWCCWGCWCCWGCWCC (SEQ ID NO: 62), and CCAGADAGACCAGGATTACT (SEQ ID NO: 63) and through the sequencing of clones selected for large insert sizes. The above oligonucleotides were designed based on published spider silk sequences (see 4, 5, 8, 9). Hundreds of positive clones were screened with restriction enzymes, and a subset of clones was sequenced (ABI) using standard M13 sequencing primers and by inserting transposons with the Genome Priming System (NEB). Divergent transcripts were recognized as members of the spider silk fibroin gene family by internal repetitiveness, sequence similarity to previously sequenced araneoid fibroins in the nonrepetitive COOH-terminus, and consistency of sequence translations with amino acid compositions from dissected silk glands and from published studies (J. Palmer (1985) J. Morphol. 186:195).

Genomic libraries were constructed for the tetragnathid, *Nephila madagascariensis* (λXGem-12, Promega), and for the araneid *Argiope trifasciata* (λFixII, Stratagene). The genomic libraries were screened with the radiolabeled probes CCWCCWGGWCCNNNWCCWCCWGGWCC (SEQ ID NO: 59) and CCWGGWCCTTGTTGWCCWGGWCC (SEQ ID NO: 60). Selected silk gene inserts were excised from the λ arms, subcloned into pGEM (Promega) vectors, and sequenced as above.

Genomic sequences were amplified from the araneoids, *N. madagascariensis, N. senegalensis, A. trifasciata, A. aurantia, Tetragnatha kauaiensis, T. versicolor, Latrodectus geometricus*, and *Gasteracantha mammosa*. PCR was by standard procedures (Gibco recombinant Taq polymerase) using primers GGTGCTGGACAAGGAGGATACG (SEQ ID NO: 64), GGCTTGATAAACTGATTGACCAACG (SEQ ID NO: 65), and CACAGCCAGAGAGACCAGGATTGC (SEQ ID NO: 66) for MaSp1 and CCAGGAGGATATGGACCAGGTC (SEQ ID NO: 67), CCGACAACTTGGGCGAACTGAG (SEQ ID NO: 68), CAAGGATCTGGACAGCAAGG (SEQ ID NO: 69), CAACAAGGACCAGGAAGTGGC (SEQ ID NO: 70), CCAACCAWTTGCGCATACTG (SEQ ID NO: 71), GCTTGAGTTAAAGAYTGACC (SEQ ID NO: 72), and GCAGGACCAGGAAGTTATG (SEQ ID NO: 73) for MaSp2. A PCR reaction generally resulted in production of a ladder of DNA fragments. Such ladders result from annealing of PCR primers to multiple binding sites in the repetitive sequences of a silk gene. For each fibroin amplified, the largest tight band in the PCR ladder was excised and cloned using the TOPO XL PCR cloning kit (Invitrogen). Two to three clones of each silk gene were sequenced as above. Additional sequences from 11 spider fibroins were taken from GenBank (accession numbers M37137, U03848, M92913, AF027735, AF027736, AF027737, AF027972, AF027973, AF218623, AF218624, U20328, U47853, U47854, U47855, and U47856). These published sequences are from the araneoid genera, Nephila and Araneus (FIG. 1).

Results

Like previously published fibroins from spiders (4-5,8-9) and lepidopterans (10-11), the sequences of the invention encode repetitive alanine and glycine-rich proteins. In each molecule, iterated amino acid motifs are organized into higher-order ensemble repeats. Ensemble repeats within each fibroin were aligned, and a consensus ensemble repeat was generated for each molecule (12). In part, silk DNA sequences from non-araneoid spiders (FIG. 2) reiterate the importance of amino acid motifs that comprise orb-weaver fibroins. GA, GGX, and $A_n$ form the consensus ensemble repeat units of silk fibroins from the pisaurid fishing spider, *Dolomedes*. The association of these three motifs in *Dolomedes* silk proteins mirrors the pattern seen in major and minor ampullate fibroins of orb-weavers (FIG. 3). GA, GGX, and $A_n$ motifs are also distributed, sometimes sparsely, among ensemble repeat units from successively more basal lineages of spiders (Haplogynae and Mygalomorphae). $A_n$ is represented in each of the fibroins from these taxa and from all lineages of Araneae studied thus far (FIGS. 2 and 3). Mygalomorphae, tarantulas and their kin, diverged from Araneomorphae, "true" spiders, minimally 240 million years ago in the middle Triassic (13, FIG. 1), thus $A_n$ motifs may have been maintained in different spider silks since that time.

Although the fibroins of *Plectreurys* (Haplogynae) and *Euagrus* (Mygalomorphae) are internally repetitive, the ensemble repeats from these basal taxa (FIG. 2) are unlike analogous units from previously described silks (FIG. 3). Each of the fibroins from these primitive groups contains stretches of serine. *Plectreurys* cDNA1 is highly internally repetitive with iterations of $A_n$, $S_n$, $(GX)_n$, and $(AQ)_n$. *Plectreurys* cDNA3 has a unique molecular architecture with the 5' end encoding a tandem array of long repeat units, and the 3' end encoding 15 repeats of a much shorter ensemble unit. The ~346 amino acid *Euagrus* repeat unit is a complex mixture of serine and alanine-rich sequences that includes a string of threonine, an amino acid that is rare in araneoid fibroins (FIG. 2).

Aside from an overall modular structure, scattered GA, GGX, and $A_n$ motifs, and amino acid matches in the non-repetitive carboxy terminus, there is only limited sequence similarity between araneoid fibroins and those from *Plectreurys* and *Euagrus* (FIGS. 2 and 3). Data presented herein clearly indicate that spiders utilize a broad diversity of fibroin sequences to spin silk threads, such diversity may be a reflection of the divergent ecosystems inhabited by these species (1,14). The novel fibroin repeats of basal Araneae suggest that spider silk design may not be especially dependent on specific sequences, but comparisons of fibroins among orb-weavers contradict this notion (FIG. 3).

In combination with published data (4-5,8-9), these new sequences allow comparisons between the two basal-most clades of ecribellate orb-weavers, Araneidae and "derived araneoids" (FIG. 1), for four groups of fibroins (15): major ampullate spidroin 1-like (MaSp1), major ampullate spidroin 2-like (MaSp2), minor ampullate spidroins (MiSp), and flagelliform silk protein (Flag). Differences among fibroins within each of these four groups are primarily variations in the arrangement and frequency of $A_n$, GA, GGX, and GPG $(X)_n$ motifs (FIG. 3). $A_n$, GA, and GGX are present in consensus repeats for both araneid and derived araneoid MiSp orthologues. Major ampullate fibroins are similarly conserved among araneoids. Stable repeats for MaSp1 are $A_n$, GA, and GGX, and for MaSp2 are $GPG(X)_n$ and $A_n$. These motifs are retained even in major ampullate fibroins of the widow *Latrodectus*, a cob-web weaving araneoid that does not spin a conventional orb web. The long Flag repeats are divergent within Araneoidea, but both araneid and derived araneoid repeat units are comprised primarily of clustered $GPG(X)_n$ and GGX motifs (FIG. 3).

Fossil evidence suggests that the divergence of Araneidae from derived araneoids occurred no later than the early Cretaceous (FIG. 1). Therefore, the motifs conserved within MaSp1, MaSp2, MiSp, and Flag have been maintained, presumably by stabilizing selection, for over 125 million years (16). Motifs that have been retained over such long evolutionary periods are likely to be critical to the divergent mechanical properties of the specialized orb-weaver silks.

EXAMPLE II

Clones of MaSp1- and Masp2-Like Spider Silk Proteins

For the purposes of further classification and structure/function analyses of the novel spider silk proteins of the present invention, fibroin sequences were allocated to different ortholog groups of *Nephila clavipes*. Silk fibroins are long proteins, comprised largely (>90%) of ensemble repeat units which are internally repetitive (4, 5, 8, 9). Ensemble repeat units from different fibroins vary in length, sometimes by an order of magnitude. It is difficult to make residue-to-residue homology statements between molecules because of this length variation and the overall modular structure of silk proteins. The gross similarities and differences between ensemble repeat units were, therefore, initially used to sort araneoid fibroins into four classes. The following proteins correspond to the MaSp1-like type of fibroin previously described in *N. clavipes* (5, 9).

MaSp1-like group proteins were characterized by short ensemble repeats with single polyalanine stretches. The remainder of a repeat was comprised of numerous GGX motifs and scattered GA motifs. The MaSp1-like group of spider silk proteins includes *N. clavipes* MaSp1, and proteins encoded by a genomic MaSp1 clone from *Argiope aurantia* (*A. aurantia*) (SEQ ID NO: 1), an *A. trifasciata* MaSp1 cDNA (SEQ ID NO: 2), a *Latrodectus geometricus* (*L. geometricus*) MaSp1 cDNA (SEQ ID NO: 3), a genomic MaSp1 clone from *N. madagascariensis* (SEQ ID NO: 4), a genomic MaSp1 clone from *N. senegalensis* (SEQ ID NO: 5), a genomic MaSp1 clone from *Tetragnatha kauaiensis* (*T. kauaiensis*) (SEQ ID NO: 6), and a genomic MaSp1 clone from *T. versicolor* (SEQ ID NO: 7). Amino acid sequences encoded by SEQ ID NOs: 1-7 are provided in SEQ ID NOs: 29-35, respectively.

MaSp2-like group proteins were characterized by short ensemble repeats comprised of one polyalanine stretch and various iterations of $GPG(X)_n$ and GP motifs. The MaSp2-like group of spider silk proteins includes *N. clavipes* MaSp2, and proteins encoded by a genomic MaSp2 clone from *A. aurantia* (SEQ ID NO: 8), an *A. trifasciata* MaSp2 cDNA (SEQ ID NO: 9), a genomic MaSp2 clone from *A. trifasciata*

(SEQ ID NO: 10), a genomic MaSp2 clone from Gasteracantha mammosa (SEQ ID NO: 11), a *L. geometricus* MaSp2 cDNA (SEQ ID NO: 12), a genomic MaSp2 clone from *L. geometricus* (SEQ ID NO: 13), two genomic MaSp2 clones from *N. madagascariensis* (SEQ ID NOs: 14-15), and a MaSp2 genomic clone from *N. senegalensis* (SEQ ID NO: 16). Amino acid sequences encoded by SEQ ID NOs: 8-16 are provided in SEQ ID NOs: 36-44, respectively.

EXAMPLE III

Clones of Flagelliform-Like Spider Silk Proteins

Based on the gross similarities and differences between ensemble repeat units, the following group of proteins was classified as flag-like type fibroins, similar to those previously described in *N. clavipes* (5, 9).

Flag-like group proteins were characterized by long ensemble repeats comprised mainly of clustered GGX and GPG(X)$_n$ motifs. Each ensemble repeat had a single "spacer" region that contained amino acids atypical of araneoid silks (5). The flag-like group of spider silk proteins includes Flag from *N. clavipes* and two proteins encoded by *A. trifasciata* Flag cDNA clones (SEQ ID Nos: 17-18). Amino acid sequences encoded by SEQ ID NOs: 17-18 are provided in SEQ ID NOs: 45-46, respectively.

EXAMPLE IV

Clones of Spider Silk Proteins Comprised of Divergent Motifs

Two of the novel spider silk proteins described herein could not be allocated readily into one of the four classes of araneoid fibroins previously described in *N. clavipes*. This group of fibroins includes spider silk proteins comprised of divergent repetitive motifs, a feature which may reflect the diverse ecosystems of the species from which the nucleic acid sequences encoding these fibroins were derived. This category includes proteins encoded by a *Dolomedes tenebrosus* (*D. tenebrosus*) fibroin 1 cDNA (SEQ ID NO: 19) and a *D. tenebrosus* fibroin 2 cDNA (SEQ ID NO: 20). Amino acid sequences encoded by SEQ ID NOs: 19-20 are provided in SEQ ID NOs: 47-48, respectively.

EXAMPLE V

Clones of Spider Silk Proteins Comprised of Atypical Motifs

Seven novel spider silk proteins of the present invention comprise atypical spider silk motifs unlike those described for any previously characterized araneoid fibroin. This group of fibroins includes spider silk proteins comprised of divergent repetitive motifs, a feature which may reflect the diverse ecosystems of the species from which the nucleic acid sequences encoding these fibroins were derived. This category includes proteins encoded by an *Euagrus chisoseus* (*E. chisoseus*) fibroin 1 cDNA (SEQ ID NO: 21), a *Plectreurys tristis* (*P. tristis*) fibroin 1 cDNA (SEQ ID NO: 22), a *P. tristis* fibroin 2 cDNA (SEQ ID NO: 23), a *P. tristis* fibroin 3 cDNA (SEQ ID NO: 24), a *P. tristis* fibroin 4 cDNA (SEQ ID NO: 25), a *Phidippus audax* (*P. audax*) fibroin 1 cDNA (SEQ ID NO: 26), and a *Zorocrates* sp. fibroin 1 cDNA (SEQ ID NO: 27). Amino acid sequences encoded by SEQ ID NOs: 21-27 are provided in SEQ ID NOs: 49-55, respectively.

EXAMPLE VI

An Exemplary Clone of a Spider Silk Protein Comprised of Divergent Motifs

A novel spider silk protein of the present invention comprises atypical spider silk motifs unlike those described for any previously characterized araneoid fibroin. This fibroin is comprised of highly divergent repetitive motifs and is encoded by a *A. trifasciata* aciniform fibroin 1 cDNA clone (SEQ ID NO: 28). Amino acid sequences encoded by SEQ ID NO: 28 are provided in SEQ ID NO: 56.

A consensus sequence repeat of the *A. trifasciata* aciniform fibroin 1 protein (SEQ ID NO: 56) comprised of approximately 200 amino acids has been identified herein.

Amino acid sequences comprising the consensus sequence repeat are provided in SEQ ID NO: 57. Such a consensus sequence is of use in a number of applications, including, but not limited to: 1) the generation of degenerative nucleic acid probes capable of encoding SEQ ID NO: 57 which can used to screen for and identify nucleic acid molecules encoding novel spider silk proteins, 2) the generation of antibodies specific for portions of or all of SEQ ID NO: 57 which can be used to screen for and identify novel spider silk proteins or derivatives thereof, and 3) utilization as a modular unit in the design and production of synthetic spider silk proteins.

EXAMPLE VII

Exemplary Methods for Designing Synthetic Spider Silk Proteins and Uses Thereof The following methods for designing synthetic spider silk proteins are based on the amino acid composition of spider silk proteins and how repetitive regions of amino acid sequences contribute to the structural/physical properties of spider silk proteins.

In general, synthetic spider silk proteins can be comprised of a series of tandem exact repeats of amino acid sequence regions identified as having a spectrum of physical properties. Exact repeats would comprise regions of amino acid sequences that are duplicated precisely. Alternatively, synthetic spider silk proteins can be comprised of a series of tandem inexact repeats identified as having a spectrum of physical properties. Inexact repeats would comprise regions of amino acid sequences in which at least one amino acid sequence can be altered in the basic inexact repeat unit as long as the alteration does not change the spectrum of physical properties characteristic of the basic inexact repeat unit.

In order to increase the tensile strength of minor ampullate silk for applications where strength and very little elasticity are needed, such as bulletproof vests, the (GA)n regions can be replaced by (A)n regions. This change would increase the tensile strength. The typical MiSp1 protein has sixteen (GA) units. Replacing eight (GA) regions, for example, with (A) regions would increase the tensile strength from 100,000 psi to at least 400,000 psi. Moreover, if the (A)n regions were as long as the (GA)n regions the tensile strength would increase to greater than 600,000 psi.

To create a fiber with high tensile strength and greater elasticity than major ampullate silk, the number of (GPGXX) regions can be increased from 4-5 regions, which is the range of (GPGXX) regions typically found in naturally occurring major ampullate spider silk proteins, to a larger number of regions. For example, if the number were increased to 10-12 (GPGXX) regions, the elasticity would increase to 50-60%. If the number were further increased to 25-30 regions, the elasticity would be near 100%. Such fibers can be used in coverings for wounds (for example, burn wounds) to facilitate easier placement and provide structural support. Such fibers can also be used for clothing and as fibers in composite materials.

The tensile strength of a very elastic flagelliform silk can be increased by replacing some of the (GPGXX) units with (A)n regions. A flagelliform silk protein contains an average of 50 (GPGXX) units per repeat. Replacing two units in each repeat with (A) regions can, therefore, increase the tensile strength of a flagelliform silk by a factor of four to achieve a tensile strength of about 400,000 psi. Uses for such flagelliform silk proteins are similar to those described for major ampullate proteins having augmented elasticity (as described hereinabove). The flagelliform proteins have additional utility in that the spacer regions therein confer the ability to attach functional molecules like antibiotics and/or growth factors (or combinations thereof) to composites comprising flagelliform proteins.

Fibers woven from combinations of the natural and/or synthetic spider silk proteins of the present invention are also encompassed herein. Such composite fibers have utility in a variety of applications, including, but not limited to, production of fabric, sutures, medical coverings, high-tech clothing, rope, and reinforced plastics.

REFERENCES AND NOTES

1. J. Coddington, H. Levi, *Annu. Rev. Ecol. Syst.* 22, 565 (1991).
2. F. Vollrath, *Intl. J. of Biol. Macromol.* 24, 81 (1999).
3. J. Gosline, P. Guerette, C. Ortlepp, K. Savage, *J. Exp. Biol.* 202, 3295 (1999).
4. P. Guerette, D. Ginzinger, B. Weber, J. Gosline, *Science* 272, 112 (1996).
5. C. Hayashi, R. Lewis, *J. Mol. Biol.* 275, 773 (1998).
6. P. Calvert, *Nature* 393, 309 (1998).
7. J. Gatesy, C. Hayashi, D. Motriuk, J. Woods, R. Lewis, *Science* 291, 2603 (2001).
8. R. Beckwitt, S. Arcidiacono, R. Stote, *Insect Biochem. Mol. Biol.* 28, 121 (1998).
9. Genbank #M37137, M92913, AF027735-AF027737, AF218621-AF218624.
10. K. Mita, S. Ichimura, T. James, *J. Mol. Evol.* 38, 583 (1994).
11. Genbank #AF08334, AF095239, AF095240.
12. DNA sequences for the various fibroins were translated into amino acid sequences. For each fibroin, ensemble repeat units, higher-order aggregations of iterated sequence motifs, were aligned algorithmically then manually using MacVector (Oxford Molecular), and a consensus ensemble repeat unit was generated. The consensus ensemble repeat was defined as the most common amino acid (or gap) at each position in the alignment of repeats for each molecule. When there was a tie at an alignment position, X denoted this ambiguity in the consensus sequence.
13. P. Selden, J. Gall, *Palaeontology* 35, 211 (1992).
14. C. Craig, *Annu. Rev. Entomol.* 42, 231 (1997).
15. Araneoid silk sequences initially were allocated to different fibroin orthologue groups in *Nephila clavipes* (5,9) according to sequence characteristics of ensemble repeat units. These assignments were assessed through phylogenetic analyses of non-repetitive carboxy-terminal sequences, expression patterns, fit to independent phylogenetic hypotheses for Araneoidea, and minimization of gene duplication events.
16. P. Selden, *Palaeontology* 33, 257 (1990).
17. A. Simmons, E. Ray, L. Jelinski, *Macromolecules* 27, 5235 (1994).
18. S. Sudo et al., *Nature* 387, 563 (1997).
19. X. Qin, K. Coyne, J. Waite, *J. Biol. Chem.* 272, 32623 (1997).
20. A. Tatham, P. Shewry, B. Miflin, *FEBS Lett.* 177, 205 (1984).
21. B. Thiel, K. Guess, C. Viney, *Biopolymers* 41, 703 (1996).
22. Q. Cao, Y. Wang, H. Bayley, *Curr. Biol.* 7, 677 (1997).
23. J. Schultz, *Biol. Rev.* 62, 89 (1987).
24. L. Chen, A. DeVries, C. Cheng, *Proc. Natl. Acad. Sci. USA* 94, 3817 (1997).
25. A. Seidel, O. Liivak, L. Jelinski, *Macromolecules* 31, 6733 (1998).
26. B. Madsen, Z. Shao, F. Vollrath, *Intl. J. Biol. Macromol.* 24, 301 (1999).
27. G. Hormiga, N. Scharff, J. Coddington, *Syst. Biol.* 49, 435 (2000).

While certain of the preferred embodiments of the present invention have been described and specifically exemplified above, it is not intended that the invention be limited to such embodiments. Various modifications may be made thereto without departing from the scope and spirit of the present invention, as set forth in the following claims.

---

What is claimed is:

1. An isolated nucleic acid molecule selected from the group consisting of a nucleic acid sequence encoding a protein of SEQ ID NOS: 36-44.

2. An isolated nucleic acid encoding an MaSP2-like spider silk protein having a plurality of repeating GPG(X)n and An units and a sequence having at least 90% identity to a sequence selected from the group consisting of SEQ ID NOS: 36-44.

3. An isolated nucleic acid encoding SEQ ID NO: 36 as claimed in claim 2.

4. An isolated nucleic acid encoding SEQ ID NO: 37 as claimed in claim 2.

5. An isolated nucleic acid encoding SEQ ID NO: 38 as claimed in claim 2.

6. An isolated nucleic acid encoding SEQ ID NO: 39 as claimed in claim 2.

7. An isolated nucleic acid encoding SEQ ID NO: 40 as claimed in claim 2.

8. An isolated nucleic acid encoding SEQ ID NO: 41 as claimed in claim 2.

9. An isolated nucleic acid encoding SEQ ID NO: 42 as claimed in claim 2.

10. An isolated nucleic acid encoding SEQ ID NO: 43 as claimed in claim 2.

11. An isolated nucleic acid encoding SEQ ID NO: 44 as claimed in claim 2.

12. An expression vector comprising at least one of the nucleic acids of claim 2.

13. A host cell comprising the expression vector of claim 12.

14. An isolated spider silk protein comprising a sequence selected from the group consisting of SEQ ID NOS: 36-44.

15. A silk fiber comprising at least one of the proteins of claim 14.

16. A copolymer fiber comprising at least two of the proteins of claim 14.

* * * * *

SEQUENCE LISTING

```
<160> NUMBER OF SEQ ID NOS: 73

<210> SEQ ID NO 1
<211> LENGTH: 1344
<212> TYPE: DNA
<213> ORGANISM: Argiope aurantia
<220> FEATURE:
<221> NAME/KEY: misc_feature
<222> LOCATION: (1020)
<223> OTHER INFORMATION: y = c or t
<220> FEATURE:
<221> NAME/KEY: misc_feature
<222> LOCATION: (1321)
<223> OTHER INFORMATION: r = a or g

<400> SEQUENCE: 1
gagccggaca aggaggagct ggagccgcag ctgctgcagc tgcagccggt ggagctggag    60
```

```
gtgctggaag aggaggatta ggtgctggcg gtgcaggaca aggatatgga tccggattag      120
gcggtcaagg aggagcaggt ggtggcgctg ccgcagctgc agcagcagca gcaggcggcc      180
aaggaggaca aggtggatat ggcggattag gttctcaagg tgctggtcaa ggaggatatg      240
gagctggaca aggaggagct ggagccgcag ctgctgcagc tgcagccggt ggagctggag      300
gtgctggaag aggaggatta ggtgctggcg gtgcaggaca aggatacgga tccggattag      360
gcggtcaagg aggagctggt caaggtggtg ctgccgcagc agcagcagca gctggcggcc      420
aaggaggaca aggtggatat ggcggattag gttctcaagg tgctggtcaa ggaggagctg      480
gtcgtggcgc tgccgcagcc gcagcagcag ctggcggcca aggaggacga ggcggatatg      540
gcggattagg ttctcaaggt gctggtcaag gaggatatgg agctggacaa ggaggagctg      600
gagccgcagc tgctgcagct gcagccggtg gagctggaga aggaggatta ggtgctggcg      660
gtgcaggaca aggatatgga tccggattag gcggtcaagg aggagctggt caaggtggtg      720
ctgccgcagc cgcagcagca gctggaggcc aaggaggaca tggtggatat ggcggattag      780
gttctcaagg tgctggtcaa ggaggagctg gtcgtggcgc tgccgcagcc gcagcagcag      840
ctggcggtca aggaggacag ggtggatatg gcggattagg ttctcaaggt gccggtcaag      900
gaggatatgg agctggacaa ggaggagctg cagccgcagc tgctgcagct gcagccggtg      960
gagctggagg tgctggaaga ggagaattag gtgctggcgg tgcaggacaa ggatatggay     1020
ccggattagg cggtcaagga ggagctggtc aacgtggtgc cgcttctgtt gcagcattag     1080
ctggagggca aggaggacaa ggtggttttg gcggatttag ttcacaagga gcaggtcaag     1140
gagcatatgg tggtggtgca tacagtggac aaggagcagc agcatctgtt tccgctgctt     1200
ccgctgcagc ttcacgtctg tcatcacctg gtgctgcttc gagagtgtct tccgctgtta     1260
cttctttggt atcaagtggc ggcccaacta atcctgcagc tttatcgaat actatcagca     1320
rtgttgtttc tcaaattagt gaga                                           1344

<210> SEQ ID NO 2
<211> LENGTH: 1947
<212> TYPE: DNA
<213> ORGANISM: Argiope trifasciata

<400> SEQUENCE: 2
gcagctgcag ccgcagcagc agcagccggt ggccaaggag acaaggtgg atatgacgga       60 ttaggttctc aaggagccgg tcaaggagga tacggacaag gaggagccgc tgccgcagca     120
gccgcagcca gtggagctgg tagtgcccaa cgaggaggct aggtgctgg aggtgcagga     180 caaggatatg gagccggatc aggcggtcaa ggaggagctg acaaggtgg cgcagctgca     240 gccacagcag cagcagccgg tggccaagga ggacaaggtg gatatggcgg attaggttcc     300
caaggatccg gtcaaggagg atacggacaa ggaggagccg ctgccgcagc agccgcagcc     360
agtggagatg gtggtgccgg acaagaaggc ttaggtgctg gaggtgcagg acaaggatat     420
ggtgctggat taggcggtca aggaggagct ggacaaggtg gcgcagctgc agccgcagca     480
gcagcagccg gtggccaagg aggacaaggt ggatatggcg gattaggttc tcaaggagcc     540
ggtcaaggag gatacggaca aggaggagcc gctgccgcag cagccgcagc cagtggagct     600
ggtggcgccg gacaaggagg cttaggtgct gcaggtgcag gacaaggata tggtgccgga     660
tcaggcggtc aaggaggagc tggacaaggt ggcgcagctg cagctgcagc agcagcagcc     720
ggtggccaag gaggacaagg tggatatggc ggattaggtt ctcaaggagc cggtcaagga     780
```

-continued

```
ggatacggac aaggaggagt cgctgctgca gcagccgcag ccagtggagc tggtggtgcc    840
ggacgaggag gcttaggtgc tggaggtgca ggacaagaat atggtgccgt atcaggcggt    900
caaggaggag ctggacaagg tggcgaagct gcagccgcag cagcagcagc cggtggccaa    960
ggaggacaag gtggatatgg cggattaggt tctcaaggag ccggtcaagg aggatacgga   1020
caaggaggag ccgctgccgc agcagcagca gccagtggag ctggtggtgc cagacgagga   1080
ggcttaggtg ctggaggtgc aggacaagga tatggtgccg gattaggtgg tcaaggagga   1140
gcaggacaag gtagcgcatc tgcagccgca gcagcagcag ccggtggcca aggaggacaa   1200
ggtggatatg gcggattagg ttctcaagga tccggtcaag gaggatacgg acaaggagga   1260
gccgctgccg cagcagccgc agccagtgga gctggtggtg ccggacgagg aagcttaggt   1320
gctggaggtg caggacaagg ttatggtgct ggattaggcg gtcaaggagg agctggacaa   1380
ggtggcgcag ctgcagccgc atcagcagca gccggtggcc aaggaggaca aggtggatat   1440
ggcggattag gttctcaagg agctggtcaa ggaggatacg gacaaggagg agccgctgcc   1500
gcagcagcat cagccggtgg ccaaggaggg caaggtggat atggtggatt aggttctcaa   1560
ggagccggtc agggaggata tggtggtggg gcattcagtg gccaacaagg cggagcagca   1620
tctgttgcca ctgcttccgc tgctgcttca cgcttgtcat cacctggtgc tgcttcgaga   1680
gtttcttctg ccgttacatc tttggtgtca agtggtggcc caactaattc tgcagcttta   1740
tctaatacta tcagcaatgt tgtttcacaa attagttcaa gcaatcctgg tctctctggc   1800
tgtgatgttc ttgttcaagc attacttgaa attgtttcag ctttggtaca tattcttggt   1860
tcagctaaca ttggacaagt taactccagc ggtgttgggc gatcagcttc tattgtggga   1920
caatctataa accaagcttt ctcataa                                        1947
```

<210> SEQ ID NO 3
<211> LENGTH: 1083
<212> TYPE: DNA
<213> ORGANISM: Latrodectus geometricus

<400> SEQUENCE: 3

```
gctggctcag gacaaggtgg ttatggacaa ggatatggtg aaggtggtgc tggacaaggg     60
ggagcaggag ccgcagcagc agccgctgca gcagctggtg gagctggaca aggtggacaa    120
ggcggttatg gacaaggata tggtcaaggt ggtgccggac aaggtggagc aggagccgca    180
gcagcagctg cagctggtgg agctggacaa ggaggctacg gccgaggtgg agcaggacaa    240
ggtgcagcag cggcagcagc agctgcaggt tcaggacaag gaggacaagg tggttatgga    300
caaggttatg gtcaaggtgg tgctggacaa gggggagcag gagccgcagc agcagcagct    360
gcagctggtg gagctggaca aggaggatac ggacgaggag gagcaggaca gggaggagca    420
gctgcagccg ctgcagcagc tggaggagcc ggtcaaggtg gacaaggcgg ttatggacaa    480
ggatatggtc aaggtggtgc cggacagggt ggagcaggag ccgcagcagc agcagctgca    540
gctggtggag ctggacaagg aggatatggc cgaggtggag caggacaagg tggatcagca    600
gcagccgcag cagcagctgg tggagcagga caaggaggat atggccgagg tggtgccgga    660
caaggtggag caggttcagc agcggcagca gctgcagctg gcggttctgg acaaggagga    720
caaggtggtt atggacaagg atatggtcaa ggtggtgctg gacaaggtgg agcagctgct    780
gcagcttctg ctttggcagc tccagctaca agtgcgagaa tttcttctca tgcctcgact    840
cttctttcaa atggtcccac caatccagct tcaatttcaa atgttattag taatgctgta    900
tcccaaatta gttcgagcaa tccaggagct tcttcgtgtg acgttcttgt tcaagctctt    960
```

-continued

```
cttgaacttg tcacagcgtt actcaccatt attgggtcct ctaatgttgg caatgttaat    1020
tatgattctt caggccaata tgcacaagtg gtttcacagt ccgtgcaaaa cgcatttgtt    1080
taa                                                                  1083

<210> SEQ ID NO 4
<211> LENGTH: 703
<212> TYPE: DNA
<213> ORGANISM: Nephila madagascariensis

<400> SEQUENCE: 4
gaggtcttgg tggacaaggt gcaggacaag gagctggagc agcagcagca gcagctggtg      60
gtgccggaca aggaggatat ggaggtcttg gaagccaagg tgctggccga ggcggatatg     120
gtggacaagg agctggagca gcagcagccg ctgccgcagg aggtgccgga caaggaggat     180
atggaggtct tggaagccaa ggtgctggac aaggaggata cggaggtctt ggtggacaag     240
gtgcaggaca aggagcagca gcagcagcag cagctggtgg tgccggacaa ggaggatatg     300
gaggtcttgg aagccaaggt gctggccgag gcggatatgg tggacaaggt gcaggagcag     360
cagcagctgc aactggtggt gctggacaag gaggatatgg tggtgtcggt tctggggcgt     420
ctgctgcctc tgcagctgca tcacgtttgt cttctcctca agctagttca agagtttcat     480
cagctgtttc caacttggtt gcaagtggtc ctacgaattc tgcggcattg tcaagtacaa     540
tcagtaacgc ggtttcacaa attggcgcca gcaatcctgg tctttctgga tgtgatgtcc     600
tcattcaagc tcttctcgag gttgtttctg ctccttatcc tatcttaggt tcttccagca     660
tcggccaagt taattatggt tccgctggtc aagccactca gat                       703

<210> SEQ ID NO 5
<211> LENGTH: 763
<212> TYPE: DNA
<213> ORGANISM: Nephila senegalensis

<400> SEQUENCE: 5
gaggtcttgg tggacaaggt gctggacgag gagctggagc agccgctgca gcagctggag      60
gtgctggaca aggaggatac ggaggtcttg gtggacaagg agctggagcc gctgccgcag     120
cagcgggtgg tgccggacaa ggaggacaag gattaggtgg aagaggtgca gcagcagctg     180 gagcgctgg acaaggagga tacggaggtc ttggtggaca aggtgctgga cgaggagctg     240
gagcagccgc tgcagcagct ggaggtgctg gtcaaggaga tacggaggt cttggtggac     300 aaggagctgg agcagcagca gcagccgctg cagcaggagg tgctggacaa ggagggtatg     360
gaggtcttgg aagccaaggt gctggacgag gaggatatgg aggacaaggt gcaggagcgg     420
cagtagcagc gattggtggc gttggacaag gaggctatgg tggtgtcggt tctggggcgt     480
ctgctgcctc tgcagctgct ctcgcttgt cttctcccga agctagttca agagtttcat     540
ctgctgtttc caacttggtt tcaagtggtc ctactaattc tgcggcattg tcaagtacta     600
tcagtaatgt ggtctcacaa ataggcgcca gcaatcctgg tctttctgga tgtgatgtcc     660
tcattcaagc tcttctcgaa gttgtttctg ctccttgtcca tatcttaggc tcttccagca     720
tcggccaggt taattatggt tccgctggtc aagccactca gat                       763

<210> SEQ ID NO 6
<211> LENGTH: 853
<212> TYPE: DNA
<213> ORGANISM: Tetragnatha kauaiensis
<220> FEATURE:
```

```
<221> NAME/KEY: misc_feature
<222> LOCATION: (59)
<223> OTHER INFORMATION: m = c or a
<220> FEATURE:
<221> NAME/KEY: misc_feature
<222> LOCATION: (70))
<223> OTHER INFORMATION: s = c or g
<220> FEATURE:
<221> NAME/KEY: misc_feature
<222> LOCATION: (122)
<223> OTHER INFORMATION: y = c or t

<400> SEQUENCE: 6
gatccggact cggaggagca ggacaaggag ccggccaagg agcatcagct gccgccgcmg      60
cagcagcags aggaggcctt ggaggtggcc aaggagcagg tcaaggagga caacaaggtg     120
cyggacaagg aggctacgga tccggactcg gaggagcagg acaaggagca tcagctgccg     180
ccgcagcagc agcagcagga ggccttggag gtggccaagg agcaggtcaa ggaggacaac     240
aaggtgctgg acaaggaggc tacgatccg gactcggagg agcaggacaa ggagcatcag     300
ctgccgccgc agcagcagca gcaggaggcc ttggaggtgg ccaaggagca ggtcaaggag     360
gacaacaagg tgctggacaa ggaggctacg atccggact cggaggagca ggacaaggag     420
ccggccaagg agcatcagct gccgccgcag cagcagcagg aggccttgga ggtggccaag     480
gaggttatgg ttctggtctt ggaggtgtag acaaggagg caaggggct ttaggtgggt      540 caagaaactc cgcaactaat gcaatttcta attctgcctc taacgctgtc tcacttctct     600
catcacctgc ttcaaatgca agaatttctt ctgctgtgtc tgccttggca tccggtgcag     660
catctggtcc tggatattta tctagcgtta tcagtaatgt tgtttctcaa gtcagctcaa     720
acagtggtgg acttgttggt tgcgatactc ttgttcaagc tcttcttgaa gctgctgctg     780
ctcttgtgca tgtattggct tcttctagtg gtggacaagt caaccttaac acagcgggat     840
acacttctca act                                                         853

<210> SEQ ID NO 7
<211> LENGTH: 535
<212> TYPE: DNA
<213> ORGANISM: Tetragnatha versicolor

<400> SEQUENCE: 7
gatctggaca aggagcatcc gccgctgcgg cagcagcagg aggccttgga ggtggacaag      60
gaggttacgg ttctggtcta ggaggtgcag acaaggagg acaacaagga gctggacaag     120
gagcagcagc tgccgcagca tcagcagcag caggaggcct tggaggtgga caaggaggtc     180
aacaaggagc aggccgaggt ggactacaag gagctggaca aggaggacaa ggtgctctag     240
gtggatcaag aaactccgca gctaatgcag tttcacgtct ctcttcacct gcttcaaatg     300
caagaatttc ttctgctgtg tctgccttgg catccggtgg agcatctagt cccggatatt     360
tatctagcat tattagcaat gtggtttctc aggttagctc aaacaatgat ggactttctg     420 gtgcgacac tgttgttcaa gctcttcttg aagttgctgc tgctcttgtg catgtattgg     480
cttcttctaa tattgggcaa gtcaaccttac atactgccgg atacacttcc caact          535

<210> SEQ ID NO 8
<211> LENGTH: 1049
<212> TYPE: DNA
<213> ORGANISM: Argiope aurantia
<220> FEATURE:
<221> NAME/KEY: misc_feature
<222> LOCATION: (117)
<223> OTHER INFORMATION: r = a or g
```

```
<220> FEATURE:
<221> NAME/KEY: misc_feature
<222> LOCATION: (142)
<223> OTHER INFORMATION: w = a or t
<220> FEATURE:
<221> NAME/KEY: misc_feature
<222> LOCATION: (238)
<223> OTHER INFORMATION: y = c or t

<400> SEQUENCE: 8
accaggmggt gccggccaac aaggtcctgg cggtcaagga ccatacggac caggtgcagc      60
cgccgcagca gcagccgctg gaggatatgg accaggagct ggacaacaag gcccagrtgg     120
agccggacaa caaggacccg gwtcccaagg accaggaggt gccggtcaac aaggacctgg     180
tggacaagga ccatacggac caggagcagc cgccgcagca gcagcagtag gaggataygg     240
accaggagct ggacaacaag gacctggaag tcaaggacca ggaagtggtg gacaacaagg     300
acctggtggt caaggacctt atggaccaag tgcagccgcc gcagcagcag ccgctggagg     360
ctatggacca ggagctggac aacaaggacc tggaagtcaa ggaccaggaa gtggtggaca     420
acaaggacct ggtggtctag gaccttatgg accaagtgca gccgcagcag cagcagccgc     480
tggaggctat ggaccaggag ctggacaaca aggacctgga agtcaaggac caggaagtgg     540
tggacaacaa agacctggtg gtctaggacc ttatggacca agtgcagccg cagcagcagc     600
agccgctgga ggctatggac caggagctgg acaacaagga cctggaagtc aaggaccagg     660
aagtggtgga caacaaagac ctggtggtct aggaccttat ggaccaagtg cagccgcagc     720
agcagcagcc gctggaggct atggaccagg agctggacaa caaggacctg gaagtcaggc     780
accagttgca tccgcagcag cctctcgtct ttcttctcct caagccagtt ctagagtttc     840
atctgctgtg tcaactttgg tgtcgagtgg tcctacgaat cctgccgcac tttctaatgc     900
tatcagtagc gttgtatcac aagttagtgc aagtaatcct ggtctttctg gttgtgacgt     960
tctcgttcaa gcattgctgg aacttgtatc cgcccttgta cacatccttg ggtcttccag    1020
cattgggcaa attaattacg ccgcgtctt                                      1049

<210> SEQ ID NO 9
<211> LENGTH: 1336
<212> TYPE: DNA
<213> ORGANISM: Argiope trifasciata

<400> SEQUENCE: 9
cgctggacca ggatacggac caggagccgg acaacaagga cctggaagtc aaggaccagg      60
aagtggtgga caacaaggac ctggtggaca aggaccatat ggaccaagcg ctgccgccgc     120
agcagctgcc gctggaccag gatatggacc aggagctgga caacaaggac caggaagtgg     180
cggacaacaa ggaggccaag gatctggaca gcaaggacca ggaggtgccg gtcaaggagg     240
tcctcgtggt caaggaccat acggaccagg tgcagccgcc gccgccgcag ctgctggagg     300
atacggacca ggagctggac aacaaggacc tggaagtcaa ggacccggaa gtggtggaca     360
acaaggtcct ggtagtcaag gaccatatgg accaagtgca gccgcagcag cagcagccgc     420
tggaccagga tacggaccag gagccggaca caaggacct ggaagtcaag gaccaggaag     480
tggtggacaa caaggacctg gtggacaagg accatatgga ccaagcgatg ccgccgcagc     540
agctgccgct ggaccaggat atggaccagg agctggacaa caaggaccag gaagtggcgg     600
acaacaagga ggccaaggat ctggacagca aggaccagga ggtgccggtc aaggaggtcc     660
tcgtggtcaa ggaccatacg gaccaggtgc agccgccgcc gccgcagctg ctggaggata     720
```

```
cggaccagga gctggacaac aaggacctgg aagtcaagga cccggaagtg gtggacaaca    780
aggtcctggt agtcaaggac catatgggcc aagtgcagcc gcagcagcag cagccgctgg    840
accaggatac ggaccaggag ccggacaaca aggacctgga agtcaaggac caggaagtgg    900
tggacaacaa ggtcctggta gtcaaggacc atatggacca agtgcagccg cagcagcagc    960
agccgctgga ccaggatacg gaccaggagc cggacaacaa ggacctggaa gtcaagcacc   1020
agttgcatcc gcagctgctt ctcgactttc ttctcctcaa gccagttctc gagtttcatc   1080
agctgtgtca actttggtgt cgagcggtcc tacgaatcct gcctcactct ctaatgctat   1140
cagtagcgtt gtatcacaag tcagttcaag taatcctggt ctttctggtt gcgatgtact   1200
cgtccaagca ttgctggaaa ttgtatccgc cctggtacat atccttggat cttctagcat   1260
tgggcaaatt aattacgccg cttcttctca gtatgcgcaa ttggttggtc aatctttaac   1320
tcaagccctt ggttga                                                   1336

<210> SEQ ID NO 10
<211> LENGTH: 360
<212> TYPE: DNA
<213> ORGANISM: Argiope trifasciata

<400> SEQUENCE: 10
ggacctggac aacaaggacc tggagggtat ggaacatccg gacctggagg tgcttctgcc     60
gccgccgctg ctgcagctgc aggtggacct ggaggacaag gaccatctgg accaggacca    120
ccaggaccag gaggatatgg accatccgga ccaggagcag ccgcagccgc cgctgcagca    180
gcaggtggac ccggaagtca aggacctgga caacaaggac ccggaggcta cggaccatct    240
ggacctggag gagcttctgc cgccgccgct gctgcagctg caggtggacc cggaggtcaa    300
ggatcatacg gaccaggaca acaaggacca ggtgcaggac aatacggacc cggacaacag    360

<210> SEQ ID NO 11
<211> LENGTH: 1026
<212> TYPE: DNA
<213> ORGANISM: Gasteracantha mammosa

<400> SEQUENCE: 11
ggccaacaag gacctggaag tcaaggacca tacggacctg gtgcagcagc tgccgcagca     60
gcagcagctg gaggataccg acctgtatct ggtcaacaag gacctggaca caaggacca    120 ggaagcggtg gccaacaagg acctggaggc caacgacctt acggaccagg tgcagccgca    180
gcagcagcag ccgcaggagg atacggacct ggatctggac aaggaggacc tggacaacaa    240
ggaccaggaa gtggcggaca caaggacctt ggaggtcaag gaccatacgg acctggtgca    300
gccgccgcag cagcagcagc cgcaggcgga tacggacctg gatctggaca aggaggacaa    360
caaggacctg gatcacaagg accaggaagt ggtggacaac aaggacctgg gggacaaggt    420
ccatacggac ctagtgccgc tgcagcagca gcagccgttg gaggatacgg accaggagct    480
ggacagcaag gacctggaca caaggacca ggaagtggtg gccaacgagg acctggaggt    540
caaggaccat atggaccagg agcagcagct gccgcagcag cagcagctgg tggatatgga    600
cctgcatctg gtcaacaagg acctggacaa caaggaccag gaagtggtgg ccaacgagga    660
cctggaggtc aaggaccata tggaccaggt gcagcagcag cagcatctgc aggaggatat    720
ggaccaggaa gtggtggaag ccctgcatca ggagcagctt ctcgactttc ttctcctcaa    780
gccggtgcca gagtttcttc agctgtatca gcccttgtcg caagtggccc aactagtcca    840
gctgctgttt ccagcgccat cagtaatgtt gcatcacaaa ttagtgcaag caatcctggt    900
```

```
ctttccggct gcgatgttct tgtacaagca ttacttgaga ttgtatcagc tcttgtatct    960
attctctcat ccgctagtat cggacaaatc aattatggcg catctggtca atatgccgcc   1020
atgatt                                                              1026
```

<210> SEQ ID NO 12
<211> LENGTH: 1118
<212> TYPE: DNA
<213> ORGANISM: Latrodectus geometricus

<400> SEQUENCE: 12

```
gcatctgcgt ctggtggagc aggacctgga agacaacaag gatatggacc aggaggatca     60
ggagcctcgg cagcagcagc cgccgccgct ggaggagctg cccaggagg atacggacaa    120 ggaccatctg gttacggccc atctggacct ggtgcacaac aaggttacgg accaggaggc    180
caaggaggat ctggagcagc agctgcagca gccgcagcag caggctctgg acctggagga    240
tatggaccag gagcagcagg accaggaagt tatggtccaa gtggacctgg aggatctggt    300
gcagctgccg cagccgctgc tgctagtgga ccaggaggac aacaaggata tggaccagga    360
ggaccaggag cctcagcagc agcagccgcc gccgctggag gatctggacc tggaggatac    420
ggacaaggac catctggtta cggcccatct ggacctggtg cacaacaagg ttacggacca    480
ggaggccaag gaggatctgg agcagcagct gcagcagccg cagcagcagg ctctggacgt    540
ggaggatatg gaccaggagc agcaggacca ggaaattatg gtccaagtgg acctggagga    600
tctggtgcag ctgcctcagc cgctgctgct agtggaccag gaggacaaca aggatacgga    660
ccaggtggat ctggagcagc tgctgcagcc gcgtctggtg gagcaggacc tggaagacaa    720
caaggatatg gaccaggagg atcaggagcc gcagcagcag cagccgccgc cgctggagga    780
tctggtccag gaggatacgg acaaggacca gccggttacg gaccaggagg ccaaggagga    840
tccggaggag cagctgcagc agccgcagca gcaagctctg gacccggagg atatggacca    900
ggagcagcag gaccaggcaa ttatggtcca agtggacctg ggggatctgg tgcagctgcg    960
gcagctgctg ctgctagtgg accaggagga caacaaggat acggaccagg tggatctggt   1020
gcatctgcag cagcagcggc tggtggtgca ggacctggaa gacaacaagc atatggacct   1080
ggaggatcag gagctgcagc agcagcagcg agtggatc                           1118
```

<210> SEQ ID NO 13
<211> LENGTH: 1196
<212> TYPE: DNA
<213> ORGANISM: Latrodectus geometricus
<220> FEATURE:
<221> NAME/KEY: misc_feature
<222> LOCATION: (198, 384)
<223> OTHER INFORMATION: w = a or t
<220> FEATURE:
<221> NAME/KEY: misc_feature
<222> LOCATION: (518, 556)
<223> OTHER INFORMATION: s = c or g
<220> FEATURE:
<221> NAME/KEY: misc_feature
<222> LOCATION: (632, 687)
<223> OTHER INFORMATION: r = a or g
<220> FEATURE:
<221> NAME/KEY: misc_feature
<222> LOCATION: (663, 1119)
<223> OTHER INFORMATION: m = c or a
<220> FEATURE:
<221> NAME/KEY: misc_feature
<222> LOCATION: (800, 876, 892)
<223> OTHER INFORMATION: y = c or t

```
<400> SEQUENCE: 13
gcaggaccag gaagttatgg tccaagtgga cctggaggat ctggtgcagc tgccgcagcc      60
gctgctgcta gtggaccagg aggacaacaa ggatatggac caggaggacc aggagcctca     120
gcagcagcag ccgccgccgc tggaggatct ggacctggag gatacggaca aggaccatct     180
ggttacggcc catctggwcc tggtgcacaa caaggttacg gaccaggagg ccaaggagga     240
tctggagcag cagctgcagc agccgcagca gcaggctctg gacctggagg atatggacca     300
ggagcagcag gaccaggaaa ttatggtcca agtggacctg gaggatctgg tgcagctgcc     360
tcagccgctg ctgctagtgg accwggagga caacaaggat acggaccagg tggatctgga     420
gcagctgctg cagccgcgtc tggtggagca ggacctggaa gacaacaagg atatggacca     480
ggaggatcag gagccgcagc agcagcagcc gccgccgstg gaggatctgg tccaggagga     540
tacggacaag gaccarscgg ttacggacca ggaggccaag gaggatccgg aggagcagct     600
gcagcagccg cagcagcaag ctctggaccc graggatatg gaccaggagc agcaggacca     660
ggmaattatg gtccaagtgg acctggrgga tctggtgcag ctgcggcagc tgctgctgct     720
agtggaccag gaggacaaca aggatacgga ccaggtggat ctggtgcatc tgcagcagca     780
gcggctggtg gtgcaggacy tggaagacaa caagcatatg gacctggagg atcaggagct     840
gcagcagcag cagcgagtgg atcgggaggt tacggycctg cgcaatatgg tyccagctcc     900
gttgcttcta gcgctgcgtc tgcggcctcg gcattatctt ctcctaccac gcatgctaga     960
atttcttccc atgcctcaac tttattatca agtggaccaa ctaactctgc agctatttct    1020
aatgtcatta gcaatgctgt tcccaagtc agtgcaagca atccaggatc ttcctcttgt     1080
gatgtccttg ttcaagcact tcttgaattg attactgcmt taattagcat agtggattct    1140
tctaacattg gacaagttaa ttacggttct tcaggccagt atgcgcaaat ggttgg        1196

<210> SEQ ID NO 14
<211> LENGTH: 5858
<212> TYPE: DNA
<213> ORGANISM: Nephila madagascariensis

<400> SEQUENCE: 14
gggagttatg gacaaggacc atcaggatat gctcaaggat catctgctgc cagtgcagcg      60
gcacctagtg gatacgtccc aagccaaaca ggccagtctg gactgggagc agcagcagca     120
gcagctgctg ttgcccctag tgggtacggc ccaagtcaac aaggaccatc tggaccagga     180
gctgctacag ccgccgcagc tggaagagga cccgaaggtt acggacccag acaacaagga     240
cctggtgcaa cagcagccgc agctggacct ggaggttacg gacccagaca caaggacct     300 ggaggctacg gacctggaca caaggacct ggtgcagctg cagccgccgc tgcaggacga     360
ggacctggag gttacggacc cggacagcaa ggaccaggag acccggtgc agcagcagcc     420 gcagctggat ctgaaggcta cggtcccgga caacaaggc caagaggacc tggtgcagcc     480
gcagctggac ctggaggcta cggacctgga caacaaggag ctagtgcagc tgcatccgcc     540
gctgcaggac gaggacctgg aggctacggt cccggacaac aaggaccagg aggacctagt     600
gcagccgcag ctggacctgg aggctacgga cccggacaac aaggaccaag tgcagctgca     660
gccgccgctg ctggaagtgg tcctggaggt tacggacccg acaacaagg tccaggagga     720 cccggtgcag cagcagccgc ggctggacct ggaggttacg gacctggaca acaaggacct     780
ggtgctgccg cagcagcagc aggacgagga cctggaggtt acggacctgg tcaacaagga     840
ccaggaggac ctggtgcagc cgccgcagca gcagcaggaa gaggaccagg aggttacgga     900
```

```
cccggacaac aaggaccagg aggacccggt gcagcagcag ccgccgctgg accaggagga    960
tacggacctg gaggttacgg acccggacaa caaggaccag gaggacctgg tgcagccgcc   1020
gcagcagcag caggaagagg accaggaggt tacggaccag acaacaagg accaggacaa   1080
caaggaccag ggggatctgg tgcagcagca gcggctgcag gacgagggcc tggaggttac   1140
ggacccggac aacaaggacc aggaggaccc ggtgcagcag cagccgccgc tggaccagga   1200
ggatacggac ctggacaaca aggacctggt gccgccgccg cagcagcagc agcaggacga   1260
ggacctggag gttacggacc cggacaacaa ggaccaggag acctggtgc agccgccgca   1320
gcagcagcag gaagaggacc aggaggttac ggaccaggac aacaaggacc aggacaacaa   1380
ggaccaggag gatctggtgc agcagcagcc gctgcaggac gaggacctgg aggttacgga   1440
cccggacaac aaggaccagg aggacccggt gcagcagcag ccgccgctgg accaggagga   1500
tacggacctg gacaacaagg acctggtgca gccgccgcag cagcagcagc aggaagagga   1560
ccaggaggtt acggaccagg acaacaagga ccaggaggat ctggtgcagc agcagccgct   1620
gcaggacgag gacctggagg ttacggacca ggacaacaag gaccaggagg accgggtgca   1680
gcagcagcag ccgctggacc tggaggttac ggacctggac aacaaggaac tggtgcagct   1740
gcagccgccg ctgctggaag tggtgccgga ggttatggac ccggacaaca aggaccagga   1800
ggacctggtg cagcagcagc gcagctggac ctggaggat acggacctgg acaacaagga   1860
cctggtgcag ctgcagccgc cgctgctgga agtggtcccg gaggttatgg acccggacaa   1920
caaggaccag gaggatccag tgcagcagca gccgccgctg accaggacg atacggacct   1980
ggacaacaag gacctggtgc agctgcagcc gcctctgctg gaagaggacc aggaggttac   2040
ggacccggac aacaaggacc aggaggacct ggtgcagcag cagccgcagc tggacctgga   2100
ggatacggac ctggacaaca aggacctggt gcagctgcag ccgccgctgc tggaagtggt   2160
cccggaggtt atggacctgg acaacaagga ccaggaggac tggtgccgc cgccgcagca   2220
gcagcaggaa gaggaccagg aggttacgga caaggacaac aaggaccagg aggacctggt   2280
gcagcagcag ccgcagctgg acctggagga tacggacctg gacaacaagg acctggagca   2340
gctgcagccg ccgctgctgg aagtggtccc ggaggttatg acccggaca caaggacca   2400
ggaagatctg gtgccgccgc cgcagcagca gcagcaggaa gaggaccagg aggttacgga   2460
cccggacaac aaggaccagg aggacccggt gcagcagcag ccgccgctgg accaggagga   2520
tacggacctg gacaacaagg acctggtgcc gccgccgcag catcagcagg aagaggacca   2580
ggaggttacg gaccaggaca acaaggacca ggaggatctg gtgcagcagc agccgctgca   2640
ggacgaggac ctggaggtta cggacccgga caacaaggac caggaggacc tggtgcagcc   2700
gccgcagcag cagcaggaag aggaccagga ggttacggac caggacaaca aggaccagga   2760
caacaaggac caggaggatc tggtgcagca gcagccgctg caggacgagg acctggaggt   2820
tacggacccg gacaacaagg accaggagga cccggtgccg cagcagccgc cgctggacca   2880
ggaggatacg gacctggaca acaaggacct ggtgcagctg cagccgccgc tgctggaagt   2940
ggtcccggag gttacggacc cggacaacaa ggaccaggag acctggtgc agcagcagcc   3000
gctgcaggac gaggacctgg aggttacgga cctggtcaac aaggaccagg aggacctggt   3060
gcagccgccg cagcagcagc aggaagagga ccaggaggtt acggaccagg acaacaagga   3120
ccaggacaac aaggaccagg gggatctggt gcagcagcag cggctgcagg acgagggcct   3180
ggaggttacg gacccggaca caaggacca ggaggacccg gtgcagcagc agccgccgct   3240
```

```
ggaccaggag gatacggacc tggacaacaa ggacctggtg ccgccgccgc agcagcagca    3300
gcaggacgag gacctggagg ttacggaccc ggacaacaag gaccaggagg acctggtgca    3360
gccgccgcag cagcagcagg aagaggacca ggaggttacg gaccaggaca caaggacca     3420 ggacaacaag gaccaggagg acccggtgca gcagcagcag ccgctggacc tggaggttac    3480
ggacctggac aacaaggaac tggtgcagct gcagccgccg ctgctggaag tggtgccgga    3540
ggttatggac ccggacaaca aggaccagga ggacctggtg cagcagcagc cgcagctgga    3600
cctggaggat acggacctgg acaacaagga cctggtgcag ctgcagccgc cgctgctgga    3660
agtggtcccg gaggttatgg acccggacaa caaggaccag gaggatccag tgcagcagca    3720
gccgccgctg gaccaggacg atacggacct ggacaacaag gacctggtgc agctgcagcc    3780
gccgctgctg gaagtggtcc cggaggttat ggacccggac aacaaggacc aggaggacct    3840
ggtgccgccg ccgcagcagc agcagcagga agaggaccag gaggttacga cccggacaa    3900 caaggaccag gaggacctgg tgcagcagca gccgcagctg gacctggagg atacggacct    3960
ggacaacaag gacctggtgc agctgcagcc gccgctgctg gaagtggtcc cggaggttat    4020
ggacctggac aacaaggacc aggaggacct ggtgccgccg ccgcagcagc agcaggaaga    4080
ggaccaggag gttacggaca aggacaacaa ggaccaggag gacctggtgc agcagcagcc    4140
gcagctggac ctggaggata cggacctgga caacaaggac ctggagcagc tgcagccgcc    4200
gctgctggaa gtggtcccgg aggttatgga cccggacaac aaggaccagg aagatctggt    4260
gccgccgccg cagcagcagc agcaggaaga ggaccaggag gttacggacc cggacaacaa    4320
ggaccaggag gacccggtgc agcagcagcc gcgctggac caggaggata cggacctgga     4380
caacaaggac ctggtgccgc cgccgcagca tcagcaggaa gaggaccagg aggttacgga    4440
ccaggacaac aaggaccagg aggatctggt gcagcagcag ccgctgcagg acgaggacct    4500
ggaggttacg gacccggaca caaggacca ggaggacctg gtgcagccgc cgcagcagca     4560
gcaggaacag gaccaggagg ttacggacca ggacaacaag gaccaggagg atctggtgca    4620
gcagcagccg ctgcaggacg aggacctgga ggttacggac ccggacaaca aggaccagga    4680
ggacccggtg ccgcagcagc cgccgctgga ccaggaggat acggacctgg acaacaagga    4740
cctggtgcag ctgcagccgc cgctgctgga agtggtcccg gaggttacgg acccggacaa    4800
caaggaccag gaggacctgg tgcagcagca gccgctgcag gacgaggacc tggaggttac    4860
ggacctggtc aacaaggacc aggaggacct ggtgcagccg ccgcagcagc agcaggaaga    4920
ggaccaggag gttacggacc aggacaacaa ggaccagggg atctggtgca gcagcagcg     4980 gcttcaggac gagggcctgg aggttacgga cccggacaac aaggaccagg aggacccggt    5040
gcagcagcag ccgccgctgg accaggagga tacggacctg gacaacaagg acctggtgcc    5100
gccgccgccg cagcagcagc aggacgagga cctggaggtt acggacccgg acaacaagga    5160
ccaggaggac ctggtgcagc cgccgcagca gcagcaggaa gaggaccagg aggttacgga    5220
ccaggacaac aaggaccagg aggatctggt gcagcagcag ccgctgcagg acgaggacct    5280
ggaggttacg gacccggaca caaggacca ggaggacctg gtgcagcagc agccgccgct     5340
ggaccaggag gatacggacc tggacaacaa ggacctggtg cagccgcagc agcagcagga    5400
agaggaccag gaggttacgg accaggacaa caaggaccag gaggatctgg tgcagcagca    5460
gccgctgcag gacgaggacc tggaggttac ggacccggac aacaaggacc aggaggaccc    5520
ggtgcagcag cagccgccgc tggacctgga ggttacggac ctggacaaca aggaactggt    5580
gcagctgcag ccgccgctgc tggaagtggt gccggaggtt atggacccgg acaacaagga    5640
```

```
ccaggaggac ctggtgcagc agcagccgcc gctggacctg gaggatacgg acctggacaa    5700
caaggacctg gtgcagctgc agccgccgct gctggaagtg gtcccggagg ttatggaccc    5760
ggacaacaag gaccaggagg acctggtgca gccgccgcag cagcagcagg aagaggacca    5820
ggaggttacg gaccaggaca caaggacca ggaggatc                              5858

<210> SEQ ID NO 15
<211> LENGTH: 1692
<212> TYPE: DNA
<213> ORGANISM: Nephila madagascariensis

<400> SEQUENCE: 15
aacagggacc atctggacct ggaagtgcag cggcagcggc agcagcagga cctggacaac      60
aaggaccagg aggatatgga ccaggacaac aaggtccagg aggatacggt ccaggacaac     120
aaggaccatc tggaccaggc agtgcagctg cagcagcagc agccgccgca gcaggacctg     180
gacaacaagg accaggagga tatggaccag gaccacaagg cccaggagga tatgtaccag     240
gacaacaagg tccatcagga tatggaccag gacaacaagg tccatctgga ccaggcagtg     300
cagcttcagc agccgcagca gcaggatctg gacaacaagg accaggagga tatggaccag     360
gacaacaagg accaggagga tatggaccag gacaacaagg accatctgga ccaggtagtg     420
cggcagcagc agccgcagca ggaccaggac aacaaggccc aggaggatat ggtccaggac     480
aacaaggtcc aggaggatat ggaccaggac aacaaggacc atctggacca ggtagtgcag     540
ctgcagcagc cgccgcagca ggacctggac aacaaggacc aggaggatat ggaccaggac     600
aacaaggtcc aggaggatat ggaccaggac aacaaggacc atctggacct ggaagtgcag     660
cggcagcggc agcagcagga cctggacaac aaggaccagg aggatatgga ccaggacaac     720
aaggtccagg aggatatggt ccaggacaac aaggaccatc tggaccaggc agtgcagctg     780
cagcagcagc cgccgcagca ggacctggac aacaaggacc aggaggatat gggccaggac     840
aacaaggacc aggacaacaa ggaccatctg gaccaggtag tgcagcagca gcagccgcag     900
caggaccagg accacaaggc ccaggaggat atggaccagg acaacaaggc ccaggaggat     960
atggaccatc tggaccaggt agtgcagctg cagcagccgc cgcagcagga cctggacaac    1020
aaggaccagg aggatatgga ccaggacaac aacgtccatc aggatatgga ccaggacaac    1080
aaggtccatc tggaccaggc agtgcagctg ccgctgcagc agcaggacct ggacaacaag    1140
gaccaggtgc ttacggacca tcaggacctg gaagtgcagc agccgcagca ggacttggag    1200
gatatggacc agcacaacaa ggaccatctg gagcaggcag tgcagcagct gcagctgcag    1260
caggacctgg tggatatgga ccagtgcaac agggaccatc tggtcctgga agcgcagccg    1320
gacctggagg ttatggacca gcgcaacaag gaccagctcg atatggacct ggaagcgcgg    1380
ccgcagctgc tgccgctgca ggatctgcag gttatgggcc aggtcctcaa gcatccgctg    1440
cagcttctcg acttgcttct ccagattcag gcgctagagt tgcatctgct gtttctaact    1500
tggtatccag tggtccaact agctctgctg ccttatcaag cgtcatcagt aacgctgtgt    1560
ctcaaattgg agccagtaat cctggtctct ctggttgcga tgtcctcatt caagctctct    1620
tggaaatcgt ttcggcttgt gtaaccattc tttcttcatc tagcattggt caagttaatt    1680
atggagcggc tt                                                         1692

<210> SEQ ID NO 16
<211> LENGTH: 693
<212> TYPE: DNA
```

```
<213> ORGANISM: Nephila senegalensis
<220> FEATURE:
<221> NAME/KEY: misc_feature
<222> LOCATION: (35, 479, 550, 613)
<223> OTHER INFORMATION: r = a or g
<220> FEATURE:
<221> NAME/KEY: misc_feature
<222> LOCATION: (142)
<223> OTHER INFORMATION: k = t or g
<220> FEATURE:
<221> NAME/KEY: misc_feature
<222> LOCATION: (248)
<223> OTHER INFORMATION: y = c or t

<400> SEQUENCE: 16
aacagggacc aggaggatat ggaccatctg gaccrggaag cgctgcagca gcttcagccg      60
cagcaggacc tggacaacaa ggaccaggtg cttacggacc atcaggacct ggaagtgcag     120
cagccgcagc gggacctgga gkatacggac caggacaaca aggtccatct ggaccaggag     180
ctgccgccgc cgcagcagga cctggacaac aaggtccagg aggatacgga ccaggagctg     240
ccgccgcygc agcagccgca caggacctg acaacaagg accagttgca tacggaccat      300
caggacccgg aagtgcagcc tctgcagctg gacctggagg ttatggacca gctcgatatg     360
gaccctcggg aagtgcagca gcagcagccg ctgctggtgc aggatctgca ggttatgggc     420
caggtcctca ggcatccgct gcagcttctc gtcttgcttc tccagactca ggtgctagrg     480
ttgcatctgc tgtttctaac ttggtatcca gtggtccaac tagctctgct gccttatcaa     540
gtgttatcar taacgctgtg tctcaaattg gcgcaagtaa tcctggtctc tctggttgcg     600
atgtcctcat tcragctctc ttggaaatcg tttctgcttg tgtaaccatc ctttcttcat     660
ctagcattgg tcaagttaat tatggagcgg ctt                                 693

<210> SEQ ID NO 17
<211> LENGTH: 1958
<212> TYPE: DNA
<213> ORGANISM: Argiope trifasciata

<400> SEQUENCE: 17
gtgcaggtgg accaggagca ggtggagcag gagctggtgg tgtcggacct ggaggatttg      60
gaggtccagg tggattcggt ggagcgggcg gtcctggagg accaggcggc ccaggaggag     120
caggcggtgg tgccggcggc gctggcggat tgtacggacc tggaggtgct ggaggattgt     180
acggtcctgg aggattatac ggacctggag gagctggagt tcccggagcg ccaggagctt     240
ctggtagagc aggaggtatc ggaggtgcag ctggaggagc aggagccggt ggtgtcggac     300
ctggaggagt ctctggaggc gctggcggtg ctggcggatc aggtgtaaca gttgtagagt     360
cagttagtgt tggtggagcc ggaggaccag gagctggtgg tgtcggtcct ggaggtgtcg     420
gacctggagg agttggaccg ggaggtattt acggaccagg aggagctgga ggactttatg     480
gaccgggtgc agtggagcc ttcgaccag gaggaggagc tggtgcacca ggaggacctg      540
gaggtccagg tggaccaggc ggcccaggtg gtcttggagg aggagtaggc ggagcaggaa     600
ccggcggtgg tgttggccca ggagctggag gtgttggacc gtctggaggt gcaggtggaa     660
ccggtccggt atctgtctct tcaactgtaa gtgtcggtgg tgctggcgga ccaggtgcag     720
gtggaccagg agcaggtgga gcaggagctg gtggtgtcgg acctggagga tttggaggtc     780
caggtggatt cggtggagcg ggcggtcctg gaggaccagg cggcccagga ggagcaggcg     840
gtggtgccgg cggcgctggc ggattgtacg gacctggagg tgctggagga ttgtacggtc     900
ctggaggatt atacggacct ggaggagctg gagttcccgg agcgccagga gcttctggta     960
```

-continued

```
gagcaggagg tatcggaggt gcagctggag ctggtggtgt cggacctggt ggagtctctg    1020
gaggtgctgg cggatcaggt gtatcagtta cagaatcagt tactgttggt ggagccggag    1080
gagcaggagc tggtggaatc ggtggaccat caggtctggg aggagccgga gcaactggtg    1140
gattcggtgg tcggggagga cctggtggac ctggaggacc cggtggacca ggaagatttg    1200
gaggtgcagc tggaggagca ggagccggtg gtgtcggacc tggaggagtc tctgaggcg     1260 ctggcggtgc tggcggatca ggtgtaacag ttgtagagtc agttagtgtt ggtggagccg    1320
gaggaccagg agctggtggt gtcggtcctg gaggtgtcgg acctgaggga gttggaccgg    1380
gaggtattta cggaccagga ggagctggag actttatgg accgggtgca ggggagcct      1440 tcggatcagg aggaggagct ggtgcaccag gagggcctgg aggtccaggt ggtccaggcg    1500
gcccaggagg tcttggagga ggagtaggcg gagcaggaac cggcggtggt gttggcccag    1560
gagttggagg tgttggaccg tctgaggggg caggtggcac cggtccggta tctgtctctt    1620
caactataac agtcggtgga ggccaatctt caggtggtgt tttaccttcg accagttatg    1680
ctccaacgac aagcggatat gaaagattac caaatttgat taatggtatt aagagctcca    1740
tgcaaggagg tggatttaat tatcagaatt ttggaaacat tctgtcgcaa tatgccacag    1800
gttctggaac atgcaactat tatgatatca atcttttgat ggatgccctt ttggccgcgc    1860
ttcacaccct caactaccag ggagcctctt atgttccatc ataccttcg ccctctgaaa     1920 tgttatcgta cacggaaaat gttcgaagat acttctga                             1958

<210> SEQ ID NO 18
<211> LENGTH: 3008
<212> TYPE: DNA
<213> ORGANISM: Argiope trifasciata

<400> SEQUENCE: 18
cggcgcacca ggaggaggcc ctggcggtgc tggaccaggt ggagcaggat ttggtcctgg      60
aggtggagct ggatttggtc ctggaggtgg agctggattt ggtcctggag gagcagcagg    120
aggtcccggt ggtccaggag gtccaggcgg cccaggagga gccggaggtt atggaccagg    180
tggagccggc ggttatggac aggaggagt cggaccaggt ggtgccggag gttatggacc     240
aggtggagcc ggaggttatg gacctggagg atccggacca ggtggtgcag gaccaggcgg    300
tgccggaggc gagggtcccg taacagtgga tgtggacgta actgttggac tgaaggagt     360 gggtggagga cctggcggtg ctggaccagg tggagcagga tttggtcctg gaggtggagc    420
tggatttggt ccgggaggag cacctggagc gccaggaggt cccggtggtc caggaggccc    480
aggaggtcca gcggacccg gaggagtcgg acctggagga gccggaggtt atggaccagg    540
tggagccgga ggtgttggac cagctggaac tggaggtttt ggaccaggtg gagccggagg    600
ttttggacca ggtggagccg gaggttttg accaggtgga gctggaggtt ttggaccagg    660
tggagctgga ggttatggac aggaggagt cggaccaggt ggagccggag gtttggacc     720 tggaggagtc ggaccggtg gttcaggacc tggcggtgca ggaggcgagg gtcccgtaac    780
agtggatgtc gacgtaagtg ttggcggcgc accaggagga ggccctggcg gtgctggacc   840
aggtggagca ggatttggtc ctggaggtgg agctggattt ggtcctggag gtggagctgg    900
atttggtcct ggaggagcag caggaggtcc cggtggtcca ggaggtccag gcggcccagg   960
aggagccgga ggttatggac caggtggagc cggcggttat ggaccaggag gagtcggacc   1020
aggtggtgcc ggaggttatg gaccaggtgg agccggaggt tatggacctg gaggatccgg   1080
```

```
accaggtggt gcaggaccag gcggtgccgg aggcgagggt cccgtaacag tggatgtgga    1140
cgtaactgtt ggacctgaag gagtgggtgg aggacctggc ggtgctggac caggtggagc    1200
aggatttggt cctggaggtg gagctggatt tggtccggga ggagcacctg agcgccagg     1260 aggtcccggt ggtccaggag gcccaggagg tccaggcgga cccggaggag tcggacctgg    1320
aggagccgga ggttatggac caggtggagc cggaggtgtt ggaccagctg gaactggagg    1380
ttttggacca ggtggagccg gaggttttgg accaggtgga gccggaggtt ttggaccagg    1440
tggagctgga ggttttggac cagctggagc tggaggttat ggaccaggag gagtcggacc    1500
aggtggagcc ggagggtttg gacctggagg agtcggaccc ggtggttcag gacctggcgg    1560
tgcaggaggc gagggtcccg taacagtgga tgtcgacgta agtgttggcg gcgcaccagg    1620
aggaggccct ggcggtgctg gaccaggtgg agcaggattt ggtcctggag gtggagctgg    1680
atttggtcct ggaggtggag ctggatttgg tcctggagga gcagcaggag gtcccggtgg    1740
tccaggaggt ccaggcggcc aggaggagc cggaggttat ggaccaggtg gagccggcgg    1800
ttatggacca ggaggagtcg gaccaggtgg tgccggaggt tatggaccag gtggagccgg    1860
aggttatgga cctggaggat ccggaccagg tggtgcagga ccaggcgtg ccggaggcga     1920 gggtcccgta acagtggatg tggacgtaac tgttggacct gaaggagtgg gtggaggacc    1980
tggcggtgct ggaccaggtg gagcaggatt tggtcctgga ggtggagctg gatttggtcc    2040
gggaggagca cctggagcac caggaggtcc cggtggtcca ggaggcccag gaggtccagg    2100
cggacccgga ggagtcggac ctggaggagc cggaggttat ggaccaggtg gagccggagg    2160
ttttggacca ggtggaactg gaggttttgg accaggtgga gccggaggtt ttggaccagg    2220
tggagccgga ggttttggac caggtggagc tggaggtttt ggaccaggtg gagccggagg    2280
ttatggacca ggaggagttg gaccaggtgg agccggaggg tttggacctg gaggagtcgg    2340
acccggtggt tcaggaccag gcggtgcagg aggcgaggt cccgtaacag tggatgtcga    2400
cgtaagtgtt ggcggcgcac caggaggagg ccctggcggt gctggaccag gtggagcagg    2460
atttggtcct ggaggtggag ctggatttgg tcctggaggt ggagctggat ttggtcctgg    2520
aggagcagca ggaggtccca gtggtccagg aggtccaggc ggcccaggag gagccggagg    2580
ttatggacca ggtggagccg gcggttatgg accaggagga gtcggaccag gtggtgccgg    2640
aggttatgga ccaggtggag ccggaggtta tggacctgga ggatccggac caggtggtgc    2700
aggaccaggc ggtgccggag gcgagggtcc cgtaacagtg gatgtggacg taactgttgg    2760
acctgaagga gtgggtggag gacctggcgg tgctggacca ggtggagcag gatttggtcc    2820
tggaggtgga gctggatttg gtccgggagg agcacctgga gcgccaggag gtcccggtgg    2880
tccaggaggc ccaggaggtc caggcggacc cggaggagtc ggacctggag gagccggagg    2940
ttatggacca ggtggagccg gaggtgttgg accagctgga actggaggtt ttggaccagg    3000
tggagccg                                                             3008

<210> SEQ ID NO 19
<211> LENGTH: 2565
<212> TYPE: DNA
<213> ORGANISM: Dolomedes tenebrosus

<400> SEQUENCE: 19
ctggttctgg acaaggcaga tacggtggtc aaggtagttc aggaggctat ggacaaggtg      60
ctggagctgg agctgccacc gccgcaactg ctagggctga tggatcggga caaggccgat    120
acgacggtca aagtagtcaa ggaggttatg gacaaggtgc tggtgctgga gctaccgcca    180
```

```
cggctgctgc tgggggagct ggttctggac aaggtggata tggtggccaa ggtggtcttg      240
gaggctatgg tcaaggagct ggtgctggag ctgcagccgc tactgcagct ggtggagctg      300
gatccggaca aggtgattac ggtgatcaag gtggtctagg aggatatggt caaggttctg      360
gagctggttc tgcaaccgct cctgctgctg gtggatctgg gtttggacaa ggggggtttcg     420 gtaatcgagg tggaaaagga gcttatggtc aaagtgctgg agctggagtt ggagctgccg      480
ccaccgctgc tgctggtgga gctggttccg gacaaggcgg atacggtgat caaggtggtc      540
taggaggata tggtcaaggt gctggagctg gtgctgcctc cgctgctgct ggaggtggag      600
atggatacga acaaggtgga tacggtaatc aaggtggttt aggaagtttt ggtcaaggag      660
ctggggctgg agctgccgcc gcagcttctg ctggtggagc tggttccgga cgaggcggat      720
acggtgatca aggtggtcta ggaggatatg gtcaaggtgc tggagctggt gctgcctccg      780
ctgctgctgg aggtggagat ggatacggac aaggttatta cggtgatcaa ggtggtcgag      840
gaggatatgg tcaaggttct ggagctggtt ctgcaaccgc tgctgctgct ggtggagctg      900
ggtttggaca aggcggatac ggacaaggtg gatacggtaa tcaaggtggt ttaggaagtt      960
ttggtcaagg agctgggggct ggagctgccg ccgccgcttc tgctggtgga gctggttccg     1020
gacgaggcgg atacggtgat caaggtggtc taggaggata tggtcaaggt gctggagctg     1080
gtgctgccgc cgctgctgct ggaggtggag atggatacgg acaaggtgga tacggtaatc     1140
aaggtggttt aggaagtttt ggtcaaggag ctggggctgg agctgccgcc gccgcttctg     1200
ctggtggagc tggttccgga cgaggcggat acggacaagg tggatacggt aatcaaggtg     1260
gtttaggaag ttttggtcaa ggagctgggg ctggagctgc cgccgccgct tctgctggtg     1320
gagctggttc cggacgaggc ggatacggtg atcaaggtgt ctaggagga tatggtcaag      1380 gtgctggatc tggtgctgcc gccgctgctg ctggaggtgg agatggatac ggacaaggtg     1440
gatacggtaa tcaaggtggt ttaggaagtt ttggtcaagg agctggggct ggagctgccg     1500
ccgccgcttc tgctggtgga gctggttccg gacgaggcgg atacggacaa ggtggatacg     1560
gtaatcaagg tggtttagga agttttggtc aaggagctgg ggctggagct gccgccgccg     1620
cttctgctgg tggagctggt tccggacgag gcggatacgg tgatcaaggt ggtctaggag     1680
gatatggtca aggtgctgga gctggtgctg cttccgctgc tgctggaggt ggagatggat     1740
acggacaagg tggatacggt aatcaacgtg gtgtaggaag ttatggtcaa ggagctgggg     1800
ctggagctgc cgccacctct gctgctggtg agctggttc cggacgaggc ggatacggtg      1860
aacaaggtgg tctaggagga tatggtcaag gtgctggagc tggtgctgcc tccactgctg     1920
ctggaggtgg agatggatac ggacaaggtg gatacggtaa tcaaggtggt cgaggaagtt     1980
atggtcaagg atctggggct ggagctggag ctgccgtagc cgctgctgct ggtggagctg     2040
tttcgggaca aggggggatac gatggtgaag tggtcaagg aggatatggt caaggttctg      2100
gagctggagc tgccgttgcc gctgcttctg gtggaaccgg agccggacaa ggcggatacg     2160
gaagccaagg tagtcaagct ggttatggtc aagtgctgg atttagagct gcagccgcca      2220
ccgccgctgc tggtgctggt ggcgccggag cggacaaggg ggatacgga ggtcaaggag      2280 gttatggtca aggaactggt gctggtggtg ctagttctgc tggactttct gttactgtgg     2340
gcaacatggt ttctcgtctt tcttctcccg aagctgcttc tagagtttct tcggcagttt     2400
ctagcttggt gtcaaatggt caagtaaatg ttgatgcatt gcctagtatt atttcaaatc     2460
tttcttcttc tatcagtgca tctgctacaa ctgcttccga ttgtgaggtc ttggttcaag     2520
```

```
ttcttctaga ggtggtgtca gctctcgtgc aaatcgtctg ctcgg              2565
```

<210> SEQ ID NO 20
<211> LENGTH: 2078
<212> TYPE: DNA
<213> ORGANISM: Dolomedes tenebrosus

<400> SEQUENCE: 20

```
gttatggtca aggttctgga gctggtgctg ccgctgctgc tgccgctgct ggtggtgctg    60
gacaaagtgg ttcaggtcct tatggtgcaa gttatctatc aagcacaaca tatacaacat   120
catcacaagg agcaggaggc ggagtaggcg gttacgggca aggtagtgga acgggatctg   180
cagctgcagc tgctggtgct gctggagcag acaaggcgg acaaggcggt tacggacaag    240
gtgctggaca aggtggtcta ggaggttatg gtcaaggtgg tggagctggt gctgccgctg   300
ccgcagccgc cgctgctggt ggagctggat ctggtcaagg tggatatggt ggtcaaggtg   360
gtctaggagg ttatggtcaa ggtgctggag ctggggctgc agccgccgct gctgctggtg   420
gagccggagc cggacaaggt ggtttcggtg gtcaaggagg gtatggccaa ggtggtggag   480
ctggtgctgc cgctgccgct gccgcagccg ccgctgctgg tggagctgga tccggtcaag   540
gtggatatgg tggtcaaggt ggtctaggag gttatggtca aggtgctgga gctggggctg   600
ccgccgccgc tgctgctggt ggagctggag ccggacaagg tagttacggt ggacaaggag   660
gttatggaca aggtggagct ggtgctgcca ctgccactgc cgccgccgct ggtggagctg   720
gatccggtca aggtggatat ggtggtcaag gtggactagg aggttatggt caaggtgctg   780
gagctggagc tgctgccgcc gctgccgctg ctgctggtgg agccggtgcc ggacaaggtg   840
gatacggagg tcaaggtggt caaggaggct atggccaagg tgctggagct ggagccgccg   900
ccgctgctgc tggtggagcc ggagccggac aaggtggtta cggtggtcaa ggaggttatg   960
gccaaggtgg tggagctggt gctgccgctg ccgcagccgc cgcttctggg ggatctggat  1020
ccggtcaagg tggatatggt ggtcaaggtg gtctaggagg ttatggtcaa ggtgctggag  1080
ctggggctgg agctgctgct ctgctgctg ctgctggagc tggatctgga caaggtggat   1140
atggtggaca aggtggtctt ggaggttacg gtcaaggagc tggagctgga gctgctgctg  1200
gtgcttctgg ttctggttct ggtggtgctg gacaaggtgg attaggagga tatggtcaag  1260
gtgcaggagc aggtgccgct gctgcagctg ctggtgctag tggggcagga caaggcggat  1320
ttggtcccta tggttctagt taccaatcaa gcacctcata ttcagtaaca tcacaaggtg  1380
ctgctggtgg attaggagga tatggacaag gtagtggagc tggtgctgca gctgcaggtc  1440
ccgcaggaca aggtggtcaa ggtggttacg gtcaaggtgc tggggcagga gccggggctg  1500
gtgctggaca aggtggatta ggaggatacg gtcaaggtgc tggttcttcc gccgcttctg  1560
ctgcggctgc tggtggagct ggagcaggac aaggtggata cggtggtcaa ggtggtctgg  1620
gtggttacgg tcaaggtgct ggagctggag cttccgccgc cgcatctgct agtggagccg  1680
gttctggaca aggtggatac ggaggtcaag gaggttacgg ccaaggaact ggtgctggtg  1740
ctgctagttc tgctggagtt gctgttactg tgggcaacac ggtttctcgt ctttcttctc  1800
cccaagctgc ttctagagtt tcctcagcag tttctagctt ggtgtcaaat ggtcaagtaa  1860
atgttgctgc attgcctagt attatttcaa gcctctcttc ttctatcagt gcatcttcta  1920
cagctgcttc cgattgtgag gtcttggtcc aagttctgct tgagatcgtg tcggctcttg  1980
tgcaaatcgt cagctcggcc aacgttggat atattaatcc tgaagcttcc ggttctctaa  2040
acgctgtcgg atctgccttg gcagccgcaa tgggttga                          2078
```

<210> SEQ ID NO 21
<211> LENGTH: 2207
<212> TYPE: DNA
<213> ORGANISM: Euagrus chisoseus

<400> SEQUENCE: 21

```
gtaacgctag tcagattgca gcaagcgtag catcagcggt cgcttcgagc gcatccgcgg        60
cggcagccgc tgcctcttcc tcagcagcag cagctgcagg cgccagttcg gctgccggtg       120
ctgcttcgag ctcttcaacg actactacta caagtacctc ctcgtctgca gcagccgcgg       180
ccgcagcagc ggcagcagct tcagcttcag gagcatcgag tgcctcggca gcagcctccg       240
catcggcagc agctagcgcc ttctcttcag ctctgatcag cgatcttttg ggaataggag       300
ttttcggtaa caccttttggt tccatcgggt cggcgtcagc tgccagttca attgcatcag       360
ccgctgctca ggcagcgctt tctggacttg gtttaagcta tctcgcttca gcgggagcta       420
gtgcagtagc cagcgcagtc gcaggggtcg gtgttggagc tggagcatac gcttacgcat       480
acgctattgc aaatgcattc gcatccatac tggcaaacac agggttactg agcgtgtctt       540
cagcagcttc ggttgcgagt agtgtggctt ccgctatcgc taccagcgtt tcctcttcgt       600
ccgccgcagc agcagcatca gccagtgcag cagcagcagc atcagccagt gcagcatcgt       660
cagcatcggc aagcagcagt gcatcagcag ctgccgcagc cggggcttcc gcggccgctg       720
gagctgcttc gtcggcatct gcttccgcag cagcgtctgc cttcagctcg gctttcatct       780
cagctttact tggattctca caatttaaca gcgtcttcgg ttccattacc tccgcgtcac       840
tcggacttgg catcgcagcg aacgctgttc agtcgggact tgcatcccctt ggtctaggag       900 ctgcggcttc ggcagcagca tctgcagtgg caaacgcagg gttaaacggc tctggtgcat       960
atgcttacgc gacagctatt gcctcggcga taggaaacgc acttcttggt gccggattct      1020
tgacagctgg taacgctagt cagattgcag caagcgtagc atcagcggtc gcttcgagcg      1080
catccgcggc ggcagccgct gcctcttcct cagcagcagc tgcaggcgcc agttcggctg      1140
ccggtgctgt tcgagctctc tcaacgacta ctactacaag tacctcctcg tctgcagcag      1200
ccgcggccgc agcagcggca gcagcttcag cttcaggagc atcgagtgcc tcggcagcag      1260
cctccgcatc ggcagcagct agcgccttct cttcagctct gatcggcgat cttttgggaa      1320 taggagttttt cggtaacacc tttggttcca tcgggtcggc gtcagctgcc agttcaattg      1380
catcagccgc tgctcaggca gcgctttctg gacttggttt aagctatctc gcttcagcgg      1440
gagctagtgc agtagccagt gcagtcgcag gggtcggtgt tggagctgga gcatacgctt      1500
acgcatacgc tattgcaaat gcattcgcat ccatactggc aaacacaggg ttactgagcg      1560
tgtcttccgc agcttcggtt gcgagtagtg tggcttccgc tatcgctacc agcgtttcct      1620
cttcgtccgc cgcagcagca gcatcagcca gtgcagcagc agcagcatca gccggtgcat      1680
cagcagcatc gtcagcatcg gcaagcagca gtgcatcagc agctgctgga gcaggtgctg      1740
gagcaggtgc tggagcttca ggtgccagtg gagctgcagg aggatcaggt ggcttcggtt      1800
tatcgtctgg tttcggtgct ggaataggag gtttaggtgg gtaccctct ggcgcgctgg      1860 gaggtcttgg tattccttct ggtttgctct catctggttt attgtctcca gctgcaaatc      1920
aaagaattgc ttctctgatc cctttgattt tgtctgcgat tcaccgaat ggcgtaaact      1980 ttggtgtgat tggaagtaat attgcatctt tagcttcgca aatatctcaa agtggtggag      2040
gtattgcagc gtctcaagct tttacccaag ctttgctgga attagtcgct gccttttattc      2100
```

-continued

| | |
|---|---|
| aagttctgtc ttctgctcaa atcggtgcag ttagtagctc ttcagcaagc gcaggcgcta | 2160 |
| ctgccaacgc atttgctcaa tcgctgtcgt cagcttttgc gggatag | 2207 |

<210> SEQ ID NO 22
<211> LENGTH: 2740
<212> TYPE: DNA
<213> ORGANISM: Plectreurys tristis

<400> SEQUENCE: 22

| | |
|---|---|
| cgccgccgcg gccgcagctg cagcagcagc cggtgccgga gcaggggctg gagcaggagc | 60 |
| aggtgctgga gcaggagcag gatctggagc ttccacatcg gtctctacca gttcatcgag | 120 |
| cggatccgga gcaggtgcag gagcaggttc tggagctgga tctggcgcag gagcaggttc | 180 |
| tggggcaggt gcaggagcag gcgctggtgg tgcaggagca ggtttcggca gtggcctcgg | 240 |
| attaggctat ggagtaggat tgtctagtgc acaagcgcag gcacaggccc aagctgccgc | 300 |
| gcaggcacaa gcacaggctc aggcccaggc atacgcagca gcacaagcac aggcacaagc | 360 |
| acaagcacaa gcacaagccg ccgccgcggc cgcagctgca gcagcagccg gtgccggagc | 420 |
| aggggctggt gcaggagcag gtgctggagc aggagcagga tctggagctt ccacatcggt | 480 |
| ctctaccagt tcatcgagcg gatccggagc aggtgcagga gcaggttctg gagctggatc | 540 |
| tggcgcagga gcaggttctg ggcaggcgc aggagcaggc gctggtggtg caggagcagg | 600 |
| tttcggcagt ggtctcggat taggctatgg agtaggattg tctagtgcac aagcgcaggc | 660 |
| acaggcccaa gctgccgcgc aggcacaagc acaggctcag gcccaggcat acgcagcagc | 720 |
| acaagcacag gcacaagcac aagcacaagc acaagccgcc gccgcggccg cagctgcagc | 780 |
| agcagccggt gccggagcag gggctggagc aggagcaggt gctggagcag gagcaggatc | 840 |
| tggagcttcc acatcggtct ctaccagttc atcgagcgga tccggagcag gtgcaggagc | 900 |
| aggttctgga gctggatctg gcgcaggagc agggtctggg gcaggcgcag gagcaggcgc | 960 |
| tggtggtgca ggagcagctt tcggcagtgg cctcggatta ggctatggag taggattgtc | 1020 |
| tagtgcacaa gcgcaggcac aggcccaagc tgccgcgcag gcacaagccg acgtcaggc | 1080 |
| ccaggcatac gcagcagcac aagcacaggc acaagcacaa gcacaagcac aagccgccgc | 1140 |
| cgcggccgca gctgcagcag cagccggtgc cggagcaggg gctggtgcag gatcaggtgc | 1200 |
| tggagcagga gcaggatctg gagcttccac atcggtctct accagttcat cgagcggatc | 1260 |
| cggagcaggt gcaggagcag gttctggagc tggatctggc gcaggagcag gttctggggc | 1320 |
| aggcgcagga gcaggcgctg gtggtgcagg agcaggtttc ggcagtggcc tcggattagg | 1380 |
| ctatggagta ggattgtcta gtgcacaagc gcaggcacag gcccaagctg ccgcgcaggc | 1440 |
| acaagccgac gctcaggccc aggcatacg agcagcacaa gcacaggcac aagcacaagc | 1500 |
| acaagcacaa gccgccgccg cggccgcagc tgcagcagca gccggtgccg gagcaggggc | 1560 |
| tggtgcagga tcaggtgctg gagcaggagc aggatctgga gcttccacat cggtctctac | 1620 |
| cagttcatcg agcggatccg gagcaggtgc aggagcaggt tctggagctg gatctggcgc | 1680 |
| aggagcaggt tctggggcag gcgcaggagc aggagctggt ggtgcaggag caggtttcgg | 1740 |
| cagtggcctc ggattaggct atggagtagg attgtctagt gcacaagcgc aggcacagtc | 1800 |
| agcagctgcc gcacgggcac aagctgacgc tcaggcccag gcatacgcag cagcacaagc | 1860 |
| acaggcacaa gcacaagcac aagcacaagc cgccgccgcg gccgcagctg cagcagcagc | 1920 |
| cggtgccgga gcaggggctg gtgcaggagc aggagctgga gcaggagcag gatctggagc | 1980 |
| ttccacatcg gtctctacca gttcatcgag cgcatccgga gcaggtgcag gagcaggttc | 2040 |

```
tggagctgga tctggcgcag gagcaggttc tggggcaggc gcaggagcag gcgctggtgg    2100
tgcaggagca ggtttcggca gtggcctcgg attaggctat ggagtaggat tgtctagtgc    2160
acaagcgcag gcacaggccc aagctgccgc gcaggcacaa gcacaggctc aggcccaggc    2220
attagcagca gcacaagcac aagcacaggc acaagcacaa gcacaagccg ccgcagcgac    2280
cgccgctgca gcagcagccg gtgccggagc aggggctggt tcaggcgcag gagctggagc    2340
aggagcagga gcagggtctg gagcttccac atcggtctct accagttcat cgagcgcagc    2400
cggagcaggt gcaggagcag gttctggagc cggagctgga tctgggacag gcgcaggtat    2460
tgctcttcct tcgatcgttc tctcccctgc agcatcatca cgaatttcgt ccgtttcgtc    2520
ctccgtccag tcagcaggtt ccggtctcag tttctcctcg ctgtcaaaca cattgtcgca    2580
gacagcatcg gctataagaa gcagcaatcc tcaactctct tccagcgatg ttctgatcca    2640
gagcttggtc gaaatcatcg tcggtttggt acaagcgttc actggttctt cagcgtcagc    2700
ccaaactttc gtgaactcat tgtctcaggt tgcgggttaa                          2740

<210> SEQ ID NO 23
<211> LENGTH: 2293
<212> TYPE: DNA
<213> ORGANISM: Plectreurys tristis

<400> SEQUENCE: 23
gtacagattc tgtcgcatcc tcagcctcta gctcggcgag tgcatcctca tcagcaacag      60
ggcctgacac gggttatcca gtagggtact acggagcagg acaagcagaa gcagcagcat     120
cagcagcggc ggcggcggca gcaagcgcag cagaagcagc aacaattgca ggtttgggct     180
acggaagaca aggtcaaggt actgattcta gtgcatcctc agtctctact tcgacaagtg     240
tatcctcatt agcaacaggg cctggctcga gatatccagt aagggactac ggagcagatc     300
aagcagaagc agcagcatca gcagcggcgg cagcaagcgc agcagaagaa atcgcaagct     360
tgggctacgg acgacaaggt caaggtacag attctgtcgc atcctcagcc tctagctcgg     420
cgagtgcatc ctcatcagca acagggcctg acacgggtta tccagtaggg tactacggag     480
caggacaagc agaagcagca gcatcagcag cggcggcggc agcaagc gcagcagaag        540 cagcaacaat tgcaggtttg gctacggaa gacaaggtca aggtactgat tctagtgcat     600
cctcagtctc tacttcgaca agtgtatcct catcagcaac agggcctgac acgggttatc     660
cagtagggta ctacggagca ggacaagcag aagcagcagc atcagcagcg gcggcggcgg     720
cagcaagcgc agcagaagca gcaacaattg caggtttggg ctacggaaga caaggtcaag     780
gtactgattc tagtgcatcc tcagtctcta cttcgacaag tgtatcctca tcagcaacag     840
ggcctgacat gggttatcca gtagggaact acggagcagg acaagcagaa gcagcagcat     900
cagcagcggc ggcggcggca gcaagcgcag cagaagcagc aacaattgca agtttgggct     960
acggaagaca aggtcaaggt actgattcta gtgcatcctc agtctctact tcgacaagtg    1020
tatcctcatc agcaacaggg cctggctcga gatatccagt aagggactac ggagcagatc    1080
aagcagaagc agcagcatca gcagcggcgg cggcggcggc agcaagc gcagcagaag       1140 aaatcgcaag cttgggctac ggacgacaag gtcaaggtac agattctgtc gcatcctcag    1200
cctctagctc ggcgagtgca tcctcatcag caacagggcc tgacacggg tatccagtag    1260 ggtactacgg agcaggacaa gcagaagcag cagcatcagc agcggcgcg gcggcagcaa     1320 gcgcagcaga agcagcaaca attgcaggtt tgggctacgg aagacaaggt caaggtactg    1380
```

```
attctagtgc atcctcagtc tctacttcga caagtgtatc ctcatcagca acagggcctg   1440
gctcgagata tccagtaagg gactacggag cagatcaagc agaagcagca gcatcagcaa   1500
cggcggcggc ggcggcggca gcaagcgcag cagaagaaat cgcaagcttg gctacggac    1560 gacaaggtca aggtacagat tctgtcgcat cctcagcctc tagctcggcg agtgcatcct   1620
catcagcaac agggcctgac acgggttatc cagtagggta ctacggagca ggacaagcag   1680
aagcagcagc atcagcagcg gcggcggcgg cagcaagcgc agcagaagca gcaacaattg   1740
caggtttggg ctacggaaga caaggtcaag gtactgattc tagtgcatcc tcagtctcta   1800
cttcgacaag tgtatcctca tcagcaacag ggcctggctc gagatatcca gtaatggact   1860
acggagcaga tcaagcagaa gcagcagcat cggcagcggc ggcggcggca gcagaagcag   1920
caacaattgc aggtttggac tacgaaggac aaggacaagg tactgattct ggtgcatcct   1980
cagtttctag ttcgacaagt gtatcctcat cagcaacagg tgttactcaa actacgatcg   2040
cccttccccc tgacgtatcc gcacgaatct cgttcctcac gtcatatttg cagtccgcag   2100
gttcaggtct cagcctctac acgctatcca acctactgtc gcagacagcg ttggccataa   2160
gcaagagccg tcctgaactc tctcccaacg aagtcctaat tcaaagttta gctgagatca   2220
tagtggcttt ggtacaagcg ctcactaaac aagccagctc ttcggcatcg gtgcaatatt   2280
tcgggcgttt cct                                                      2293

<210> SEQ ID NO 24
<211> LENGTH: 6052
<212> TYPE: DNA
<213> ORGANISM: Plectreurys tristis

<400> SEQUENCE: 24
cgcaatcagc tcgagtttgt acgctttcaa ttaccaggcg tcggcggcaa gttcagctgc     60
tgcacagagc tcggcccaaa ctgcgtctac ttcagcaaaa cagacagctg caagtacgtc    120
tgcatcaaca gcagcaactt ctacaacaca gacagctgca acaacgtctg catcgacggc    180
agcaagttca caaacggttc agaaagcaag cacgagttcc gccgcatcaa ctgctgcctc    240
caagtctcag agcagttccg cgggcagttc gagaacgacc tcaactgctg cagcatccgc    300
aagcagcagt tatgcattcg cacaaagttt atcgcagtat ctcctgtctt cgcagcaatt    360
cacgactgcc ttcgcaagtt ctaccgccgt agcgtcctct cagcagtacg cggaagccat    420
ggcccagtct gtcgccacgt ctcttggact cggctacaca tatgcgtctg cactttctgt    480
cgccatggca caagccatct ccggggttgg cggaggagct agcgcttaca gttacgcaac    540
ggccatttcg caagccattt ctagagctct acaagttcc ggcgtatctc tgtcctcttc    600
gcaagcgacg tctgttgctt ccgcaatcag ctcgagtttg tacgctttca attaccaggc    660
gtcggcggca agttcagctg ctgcacagag ctcggcccaa actgcgtcta cttcagcaaa    720
acagacagct gcaagtacgt ctgcatcaac agcagcaact tctacaacac agacagctgc    780
aactacttct gcatcgacgg cggcaagttc acaaacggtt cagaaagcaa gcacgagctc    840
cgccgcatca actgctgcct ccaagtctca gagcagttcc gtgggcagtt cgacgacctc    900
aactgctgca gcatccgcaa gcagcagtta tgcattcgca caaagtttat cgcagtatct    960
cctgtcttcg cagcaattca cgactgcctt cgcaagttc accgccgtag cgtcctctca    1020
gcagtacgcg gaagccatgg cccagtctgt cgccacgtct cttggactcg gctacacata    1080
tacgtctgca ctttcggtcg ccatggcaca agccatctcc ggggttggcg gaggagctag    1140
cgcttacagt tacgcaacgg ccatttcgca agccatttct agagttctta caagttccgg    1200
```

```
catatctctg tcctcttcgc aagcgacgtc tgttgcttcc gcaatcagct cgagtttgta   1260
cgctttcaat taccaggcgt cggcggcaag ttcagctgct gcacagagct cggcccaaac   1320
tgcgtctact tcagcaaaac agacagctgc aagtacgtct gcatcaacag cagcaacttc   1380
tacaacacag acagctgcaa ctacttctgc atcgacggcg gcaagttcac aaacggttca   1440
gaaagcaagc acgagctccg ccgcatcaac tgctgcctcc aagtctcaga gcagttccgt   1500
gggcagttcg acgacctcaa ctgctgcagc atccgcaagc agcagttatg cattcgcaca   1560
aagtttatcg cagtatctcc tgtcttcgca gcaattcacg actgccttcg caagttctac   1620
cgccgtagcg tcctctcagc agtacgcgga agccatggcc cagtctgtcg ccacgtctct   1680
tggactcggc tacacatata cgtctgcact ttctgtcgcc atggcacaag ccatctccgg   1740
ggttggcgga ggagctagcg cttacagtta cgcaacggcc atttcgcaag ccatttctag   1800
agttcttaca agtccggcg tatctctgtc ctcttcgcaa gcgacgtctg ttgcttccgc   1860
aatcagctcg agtttgtacg ctttcaatta ccgggcgtcg gcggcaagtt cagctgctgc   1920
acagagctcg gcccaaactg cgtctacttc agcaaaacag acagctgcaa gtacgtctgc   1980
atcaacagca gcaacgtcta caacacagac agctgcaact acttctgcat cgacggcagc   2040
aagttcacaa acggttcaga aagcaagcac gagctccgcc gcgtcaactg ctgctcagca   2100
gactgggcaa tcctcttctg tacagaatca aggaagctcc tctgccagct cgagttcagt   2160
cagcgtttct gatatctccg attctctcac aacatctttg ctgcagtctg aagaattcac   2220
atcggccttc ggaagcacag ttagcgaggc tgaggcccag tcgtacgcgg aggccgtggc   2280
tcagtctact gtcgcacaac tcgggataga ttattctcaa agctccgctc tcgctactgc   2340
tgtagcaaac gcagtatcac aagttaaaca aggctccagt tctcgcgctt atgcccgcgc   2400
catagcatat gcaatcacga cgtacctgaa aactactcga attattacta ctattactag   2460
aactcaagtg aaatcatttg cctctgcaat cagttcgagc ctgtctacag cgagggcgac   2520
atctagtgca aatgcatatc aggaacagac cactcagtct tctgcagcag caagtgcggc   2580
agcacagtcc agtgagtatc aaacgcagaa cactcagtct tctgcctctg cggcaagcag   2640
tgatgcaagc acttcctacc agacacagca gagttactcg gacgcgtcgg cagccagcgt   2700
tgcagcagaa agcacaagcg cgaatcaagc gcagagcacg cagtcatcgg ccgccgcaag   2760
cagctctaca aattctgcct accagagcca acaaagctac atagatgctt ctacggtcag   2820
ctctgcgtct gcaaatacag cgcagtcgac ttaccaagta acaattcctg ataatacgta   2880
ttttgctgaa tctctgtcat ccacactgat acaacatgag caattcaatt cgaaattcgg   2940
aagctacatt ccactagtaa ctgctcggga gtatgcttcg gcaatggctc gagcaacagc   3000
tcttatcatt ggttttgaca gcactggaac ttcagcactt gagtctgcgg tcgcagtagc   3060
ggtatccaat gtcgattatg ccagcgcata ttcctacgcc agagcaatag catttgcaat   3120
tagcaatgta cttaccaaca atggaatatt cgcgtcagcc tcagaagcac tatatcttgc   3180
ccctgccatg atagcaagtt tgcatgcatt tggtaagtcg agcttttctg aaagttcggc   3240
attcgcattg gctaacagca tctctccgtc aacagcaata acgtccgcgc aaagcagcag   3300
tgtatctgct ggcgcatctt caggacaaag ctcatatgac actagcagtg tcgtttcctc   3360
agccagcagc gcagaagcaa cggaatcttc aagcgtcttt gatacttatc aagctacgca   3420
aatcgaaagt tctgcagccg ccgcagccgc atcgtcatcg gcatatgact cgcaattttc   3480
tgaatcttct tctgctagca gtgcagcagc ttcagctttt tcggaacaga cctcctatga   3540
```

```
cataagcagt gacttatctt cagcaagcag cgctactgcc gcagctgctt cgtcctcagc    3600
ttatgaatcg caattttcgg acgcttcttc cggtagcagt gcagctgccg ctgcttcttc    3660
gcagcagaac tcatacgaca ccgatgcctt gtattcagca agcagcgctg cttccgctgc    3720
cgcatcggcc tcagcttacg aattggaatt ttcggacgct tcttctagca gcagcgcagt    3780
tgccgttgct tcttcgcagc agggctcata cgacacaagc agtgacttct cttcagcgag    3840
cagcgctgcg gccgcagctg catcggctta cgaatcgaaa tttttggacg cttcttctag    3900
cagcagcgca gctgccgctg cttcttcgca gcagagctca tacgaaacaa gcagtgactt    3960
agtttcagcg agcagcgctg cggctgcagc tgcatcggcc tcggcttacc aatcgcaatt    4020
tttggacgct tcttctagca gcaatgcagc tgccactact tcttcgcggc agagctcata    4080
tgacacaagc agtgacttct cttcagccag catcgctgcg gccgcagctg catcggcctc    4140
gtcttatgaa tcgcaatttt cggacgcttc ttctagcagc aatgcggctg ccgctgcttc    4200
ttcgcagcag agctcatacg atacaagcag tgacttagtt tcagctgcat cggcctcggc    4260
ttatgaatcg caattttggg acgcttcttc tagcagcaat gcagctgcca ctacttcttc    4320
gcagcagagc tcatatgaca caagcagtga cttctcttca gccagcatcg ctgcggccgc    4380
agctgcatca gcctcgtctt atgaatcgca attttcggac gcttcttcta gcagcaatgc    4440
ggctgccgct gcttcttcgc agcagagctc atacgataca agcagtgact tagtttcagc    4500
gagcagcgct gcggccgcag ctgcatcggc ctcgtcttat gaatcgcaat tttcggacgc    4560
ttcttctagc agcaatgcgg ctgccgctgc ttcttcgcag cagagctcat acgatacaag    4620
cagtgactta gtttcagcga gcagcgctgc ggctgcagct gcatcggcct cggcttatga    4680
atcgcaattt tcggacgctt cttctagcag aaatgcggct gccgctgctt cttcgcagca    4740
gagctcatac gatacaagca gtgacttagt ttcagcgagc agcgctgcgg ccgcagctgc    4800
atcggcctcg tcttatgaat cgcaattttt ggacgcttct tctagcagca atgcagctgc    4860
cactacttct tcgcagcaga gctcatatga cacaagcagt gacttctctt cagccagcat    4920
cgctgcggcc gtagctgcat cagcctcgtc ttatgaatcg caattttcgg acgcttcttc    4980
tagcagcaaa gcagctgccg ctgcttcttc gcagcagagc tcatacgata caagcagtga    5040
cttagtttca gcgagcagcg ctgcggccgc agctgcatcg gcctcgtctt atgaatcgca    5100
attttcggac gcttcttcta gcagcaatgc agccgccgct gcttcttcgc agcagagctc    5160
atacgataca agcagtgact tctcttcagc gaacagtgct gctctagcag aatcttcagc    5220
tgccactgaa atttaccaag agacacaaat cgcaagttcc attgcagccg cttcagcatt    5280
gtcggaagca catacgtcag aattggccga agcttcttcc agcagcagtg cagcttctgc    5340
agcagcagca gcagcttcgg aacaaagcct ttacgacacg agcagtgccg cttcttcagc    5400
aagcagcagc gacttcatag cttcttcgga tatccgtaat caacagagtt tgtccgttaa    5460
ctctgcagcg agcagcagtg cagcggaaga gagcgtttcg caagttgacg aagaaacgta    5520
ccaaaacttt gatcagtact cttcaatttc agcgtcagca tcggcagctc agagctcaga    5580
aatttaccaa gatgtatcct cctcttcggc agcagcctct acatcttcag cagcgtcttc    5640
cttggaaaca tctggaacag ttgcagaaag cggatctaca gcagcaagca gcagctatgc    5700
agcagcagca gcagcgtcct catcagcggg ctcgacgagc tcgccctcat tcctgtcagc    5760
ggacagcctg tcgtcctctt tggcttctct gagaatttgt tccttttcct ctaagctgat    5820
gtcttccttg tactcaggtg atggtctcga catcgcggag ttctccgatg cagtatcttc    5880
catggtttct agtatcaaaa gttcaaatcc aggtgtaagt gcttctcaga tactcacaga    5940
```

```
actgctcttc gaggtaatcg tagcttttgt tcaagctctc acaaaatcga agttttcaac    6000
tatggagacg gctgaatctc taatagcggc cttcgcacaa gctttcgtct aa            6052

<210> SEQ ID NO 25
<211> LENGTH: 5446
<212> TYPE: DNA
<213> ORGANISM: Plectreurys tristis

<400> SEQUENCE: 25
gtcccagcaa ggacctatcg gaggtgtcgg cgggtcgaac gcctttagta gttccttcgc      60
cagcgcactc agtttgaacc gaggatttac cgaagttatc agcagcgcct ccgcaaccgc     120
ggttgcttct gccttccaga aagggcttgc accttacggt acggcattcg ctttgtctgc     180
agcgagcgca gcagctgacg cttacaactc tattggttca ggagcaaatg cgttcgccta     240
tgctcaagct ttcgcaagag tactgtatcc gttggttcga caatatggtt tatcttcgag     300
cggtaaagct tctgctttcg ccagtgccat tgcaagctct tttagcagtg gtacctccgg     360
ccaaggaccg tcgattggac aacaacagcc tccggttacg atctcagcgg cgtcagcatc     420
agcaggtgct tcggctgctg ccgtaggagg cgggcaagta ggccaggggc catatggtgg     480
gcagcaacag agcactgcag cttcggcttc agcagcagca gctactgcta cttctggcgc     540
agcacagaag cagccttcag gcgagtcctc agtggcaact gcatcggcgg cagcaacttc     600
ggttacttct ggcggagcgc cggttggaaa accaggagtt ccagcaccaa tattttatcc     660
gcaaggtcca ttgcaacaag gaccagcccc cggaccttcc aacgtccagc caggaacgtc     720
ccagcaagga cctatcggag gtgtcggcgg gtcgaacgcc tttagtagtt ccttcgccag     780
cgcactcagt ttgaaccgag gatttaccga agttatcagc agcgcctccg caaccgcggt     840
tgcttctgcc ttccagaaag ggcttgcacc ttacggtacg gcattcgctt tgtctgcagc     900
gagcgcagca gctgacgctt acaactctat tggttcagga gcaaatgcgt tcgcctatgc     960
tcaagctttc gcaagagtac tgtatccgtt ggttcgacaa tatggtttat cttcgagcgg    1020
taaagcttct gctttcgcca gtgccattgc aagctctttt agcagtggta cctccggcca    1080
aggaccgtcg attggacaac aacagcctcc ggttacgatc tcagcggcgt cagcatcagc    1140
aggtgcttcg gctgctgccg taggaggcgg gcaagtaggc caggggccat atggtgggca    1200
gcaacagagc actgcagctt cggcttcagc agcagcagct actgctactt ctggcgcagc    1260
acagaagcag ccttcaggcg agtcctcagt ggcaactgca tcggcggcag caacttcggt    1320
tacttctggc ggagcgccgg ttggaaaacc aggagttcca gcaccaatat tttatccgca    1380
aggtccattg caacaaggac cagccccgg accttccaac gtccagccag gaacgtccca    1440
gcaaggacct atcggaggtg tcggcgggtc gaacgccttt agtagttcct tcgccagcgc    1500
actcagtttg aaccgaggat ttaccgaagt tatcagcagc gcctccgcaa ccgcggttgc    1560
ttctgccttc agaaagggc ttgcacctta cggtacggca ttcgctttgt ctgcagcgag    1620
cgcagcagct gacgcttaca actctattgg ttcaggagca aatgcgttcg cctatgctca    1680
agctttcgca agagtactgt atccgttggt tcaacaatat ggtttatctt cgagcgctaa    1740
agcttctgct ttcgccagtg ccattgcaag ctcttttagc agtggtacct ccggccaagg    1800
accgtcgatt ggacaacaac agcctccggt tacgatctca gcggcgtcag catcagcagg    1860
tgcttcggct gctgccgtgg gaggcgggca agtaggtcag gggccatatg gtgggcagca    1920
acagagcact gcagcttcgg cttcagcagc agcagctact gctacttctg gcggagcaca    1980
```

```
gaagcagcct tcaggcgagt cctcagtggc aactgcatcg gcggcagcaa cttcggttac      2040
ttctgccgga gcgccggttg gaaaaccagg agttccagcc ccaatatttt atccgcaagg      2100
tccattgcaa caaggaccag cccccggacc ttccaacgtc cagccaggaa cgtcccagca      2160
aggacctatc ggaggtgtcg gcgggtcgaa cgcctttagt agttccttcg ccagcgcact      2220
cagtttgaac cgaggattta ccgaagttat cagcagcgcc tccgcaaccg cggttgcttc      2280
tgccttccag aaagggcttg caccttacgg tacggcattc gctttgtctg cagcgagcgc      2340
agcagctgac gcttacaact ctattggttc aggagcaaat gcgttcgcct atgctcaagc      2400
tttcgcaaga gtactgtatc cgttggttca acaatatggt ttatcttcga gcgctaaagc      2460
ttctgctttc gccagtgcca ttgcaagctc ttttagcagt ggtacctccg gccaaggacc      2520
gtcgaatgga caacaacagc ctccggttac gatctcagcg gcgtcagcat cagcaggtgc      2580
ttcggctgct gccgtgggag gcgggcaagt aagtcagggg ccatatggtg gcagcaaca      2640 gagcactgca gcttcggctt cagcagcagc agctactgct acttctggcg gagcacagaa      2700
gcagccttca ggcgagtcct cagtggcaac tgcatcggcg gcagcaactt cggttacttc      2760
tgccggagcg ccgggtggaa accaggagt tccagcacca atattttatc cgcaaggtcc      2820
attgcaacaa ggaccagccc ccggaccttc aacgtccag ccaggaacgt cccagcaagg      2880
acctatcgga ggtgtcggcg gtcgaacgc ctttagtagt tccttcgcca gcgcactcag      2940
tttgaaccga ggatttaccg aagttatcag cagcgcctcc gcaaccgcgg ttgcttctgc      3000
cttccagaaa gggcttgcac cttacggtac ggcattcgct ttgtctgcag cgagcgcagc      3060
agctgacgct tacaactcta ttggttcagg agcaaatgcg ttcgcctatg ctcaagcttt      3120
cgcaagagta ctgtatccgt tggttcaaca atatggttta tcttcgagcg ctaaagcttc      3180
tgctttcgcc agtgccattg caagctcttt tagcagtggt acctccggcc aaggaccgtc      3240
gattggacaa caacagcctc cggttacgat ctcagcggcg tcagcatcag caggtgcttc      3300
ggctgctgcc gtgggaggcg ggcaagtagg tcaggggcca tatggtgggc agcaacagag      3360
cactgcagct tcggcttcag cagcagcagc tactgctact tctggcggag cacagaagca      3420
gccttcaggc gagtcctcag tggcaactgc atcggcggca gcaacttcgg ttacttctgc      3480
cggagcgccg gttggaaaac caggagttcc agcaccaata ttttatccgc aaggtccatt      3540
gcaacaagga ccagctcccg gaccttccta cgtccagcca gcaacgtcgc agcaaggacc      3600
tatcggaggt gccggccggt cgaacgcatt tagtagttcc ttcgccagcg cactcagtgg      3660
gaaccgagga tttagcgaag ttatcagcag cgcctccgca accgcggttg cttctgcctt      3720
ccagaaaggg cttgccccct acggtacggc atttgcttta tctgcagcga gcgctgcagc      3780
tgacgcttac aactctattg gttcaggagc aaatgcgttc gcctatgctc aagctttcgc      3840
aagagtactg tatccgttgg ttcaacaata tggtttatct tcgagcgcta agcttctgc      3900 tttcgccagt gccattgcaa gctctttcag cagtggcgcc gccggccaag acagtcgat      3960 accatacggt ggacaacaac aacctccaat gacgatctca gcggcgtcag catcagcagg      4020
tgcttcagct gctgccgtga aggcgggca agtaggtcag gggccatatg gtggccagca      4080
acagagcact gcagcttcgg cttcagcagc cgcaactact gctactgctg cggagcccaa      4140
gaagcaccct tcaggcgaat actcagtggc aactgcatcg gcggcagcaa cttcggttac      4200
ttctggcgga gcgccggttg gaaaaccagg agttccagcg ccaatatttt atccgcaagg      4260
tccattgcaa caaggaccag cccccggacc ttccaacgtc cagccaggaa cgtcgcagca      4320
aggacctatc ggaggtgtcg gcgagtcgaa caccttagt agttccttcg ccagcgcact      4380
```

-continued

```
cggtgggaac cgaggattta gcggagttat cagcagcgcc tccgcaaccg cggtcgcgtc    4440
tgccttccag aaagggcttg cccctacgg taccgcattc gctttatctg cagccagcgc    4500
tgcagctgac gcttacaact ctattggttc aggagcaagt gcgtctgcct atgctcaagc    4560
tttcgcaaga gtgctgtacc cattgctcca gcaatatggt ttatcttcga gcgctgacgc    4620
ttccgctttc gccagtgcta ttgcaagttc ttttagcact ggggtcgccg gccaaggacc    4680
gtcggtacca tacgttggac aacaacagcc ttcgattatg gtctcagcag cttcagcatc    4740
agcagctgct tcagccgctg ccgtgggagg cggcccagta gttcagggc catacgatgg    4800 aggacagcct cagcaaccga acattgctgc ttcggcggca gcagcagcta ctgctacttc    4860
tagtggacct aaagaggagc ctttgggcga gtcctctgtg atagctacat cggtgtcagc    4920
cgcctcgtcg gtttcttctg cggagcccc aggtgtacaa ggcggaggtc cagtgacagt    4980
gtcttatcgt gaaggtcctt ctcaaattcc ttctcaacaa cgctgctgc aggcggtacc    5040 ttctacgcag tctgttgggt ctggtgttcc tgttgggcct aatcagtatg aaatggttta    5100
tgctcctttg cagcaattcg gtggtgtttc ggcttctaat ttgctttcac cgtcggcaca    5160
tagcagaata gcatcgctga tgtcggacgt acttagtctt ttttcgccag gaaactctgg    5220
ttttaactat gggggtttg ctagagctct ctcgtctgtg gctcgcgcag ttagccagtc    5280
taatgccaag ttgtcgacca ctgacgttat cattcaagtt ttgatggaag ctctagttgc    5340
gctaattgag ctcttgtcgg gtgcgaaaat tggtgttgtt catcccgtgc gggctcaggc    5400
tggtgccagt gcttttgctc aacatttcgg cagtgcgttt gggtga               5446
```

<210> SEQ ID NO 26
<211> LENGTH: 1711
<212> TYPE: DNA
<213> ORGANISM: Phidippus audax
<220> FEATURE:
<221> NAME/KEY: misc_feature
<222> LOCATION: (1066)
<223> OTHER INFORMATION: s = c or g
<220> FEATURE:
<221> NAME/KEY: misc_feature
<222> LOCATION: (1078)
<223> OTHER INFORMATION: r = a or g
<220> FEATURE:
<221> NAME/KEY: misc_feature
<222> LOCATION: (1681)
<223> OTHER INFORMATION: n = a, c, g, or t

<400> SEQUENCE: 26

```
ggagctggag ctggcgctgg ctatggtgca ggtgctggtt caggagctgg tgcaggctct      60
ggtgcaggag ctggagcagg agctggagca ggagctggag caggctatgg agcaggagca     120
ggttcaggag ctggtgctgg cgcaggttac ggacgaggtg caggagcagg agcgggagct     180
ggagcaggtt acggccaagg tgctggagcg ggagctggtg ccggcgcagg ctatggcgct     240
ggagctggat ctggagctgg agccggctat ggtacaggtg ctggttcagg agctggttca     300
ggagctggtt caggagctgg atcaggagct ggagcaggag ctggagcagg tgcaggttat     360
ggagcaggag caggttcagg agctggtgct ggcgcaggct acggacgagg tgcaggagca     420
ggagcgggag ctggagcagg ttacggccaa ggtgctggag caggagctgg tgccggtgca     480
ggtgctggtt caggagctgg tgcaggttct ggtgcaggag ctggtgctgg tgcaggttac     540
ggacaaggtg caggagcagg agctggtgcc ggtgcagggt atggcgctgg agcaggttct     600
ggagctggag ctggcgctgg ctacggtgca ggtgctggtt caggagctgg tgcaggttct     660
```

| | |
|---|---|
| ggtgcaggag ctggtgctgg agcaggttac ggtcaaggtg ctggagctgg agctggcgcc | 720 |
| ggctatggtg caggtgctgg ttctggagct ggtgcaggct ctggtgcagg agctggatca | 780 |
| ggagctggag ctggttcagg ctatggcgca ggagctggtt caggagctgg cgctggcgca | 840 |
| ggttatggac aaggtgccgg agcaggtgct ggtgcaggtg caggctatgg tgcaggagca | 900 |
| ggttctggag ctggaactgg tgcaggctat ggtgctggtg caggtgcagg atatggtgct | 960 |
| ggtgcaggtg caggagctgg ttcaggagca ggtgccgggg caggttatgg tgctggtgct | 1020 |
| ggtgcaggcg ctggagcagg ctatggtgct ggagctggtt ccggascagg tgcaggarca | 1080 |
| ggttatggtg ctggtgcagg tgcaggttca ggtgtaggag caggtgctgg agctggtgct | 1140 |
| ggagcaggat atggagctgg agcaggtgca ggagcaggct atggtgctgg tgcaggtgca | 1200 |
| ggtgctggtg ctggtgcagg agcaggatat ggcgctggag caggtgcagg tgcttctgta | 1260 |
| agttccactg tatctaacac tgcttccaga atgtcttcag agaatacatc acgtcgtgtt | 1320 |
| tcttcagcca tttcaagcat tgtcggctct ggtggagtta acatgaattc tctttcaaac | 1380 |
| gtaatctcta atgtatcatc gagcgttgct gcatctaatc ctggactgtc tggatgtgaa | 1440 |
| gttcttgttc aaaccctgtt ggaagtagta tctgcattgg ttcacatttt gagctatgca | 1500 |
| agtgtgggta gtgttgatgc cagcgctgct ggtcagtcag cccagactgt agctacagcc | 1560 |
| atgagtagta taatgggttg aattactttg acctttcaat attttgaag acttatgtt | 1620 |
| gttacttttt gaattacgta atgtctgaaa ataagataa ataatagaa gtatatatgc | 1680 |
| naaaaaaaa aaaaaaaaa aaaaaaaaa a | 1711 |

<210> SEQ ID NO 27
<211> LENGTH: 845
<212> TYPE: DNA
<213> ORGANISM: Zorocrates sp.

<400> SEQUENCE: 27

| | |
|---|---|
| ggtgcagcag ccgcagcctc agcagcagca gcaggcggac gaggaagcca aggaggttac | 60 |
| ggagatgacg gtggtgcagc agcagcagca gcagcagcag cggcggcagc cgcggcagga | 120 |
| agtggtggaa ccggaggagg acaaggggg cgcggagatg gaggtgcggc agcagcagca | 180 |
| gcagcagccg cagaggccgc agcaggtgga aaaggaagac aaggaagtta cggagatgac | 240 |
| ggtggtgcag cagtagcagc agcagctgca gcggcagcag cggcaggaag aggtggttcc | 300 |
| ggaagaggac aaggacttcg tagagataaa ggaagttacg gagttgacgg tggtgcagaa | 360 |
| gcagcagcat ccgcagcggc cacagcaggc agacaaggaa gacaaggaag ttacggagat | 420 |
| gacggtggtg cagcagcagc agcagcagca gcggcttctg cttcacggtt agcctcctct | 480 |
| tctgctgttt ctcgagtctc atctgctgtt tctgcgctgt tgtcaaatgg cttttctgat | 540 |
| gtaaattccc tctccaacgt gatttctgga cttctgctt ctgtatcttc ttccacacct | 600 |
| gagctgactg gttgcgaagt tctcgtggaa gtccttttgg aagtagtatc agctttggtt | 660 |
| catattttga actttgctga cattggaaac gttaatatta gtgcttcagg tgattccaca | 720 |
| tcccttgtag gccgaactgt tttagaagcc tttggctgaa atattactct attccttttt | 780 |
| tttttttgaa tattgtttca gcttttaact gtgacataaa aatgttata taaggaataa | 840 |
| atata | 845 |

<210> SEQ ID NO 28
<211> LENGTH: 709
<212> TYPE: DNA
<213> ORGANISM: Argiope trifasciata -continued

<400> SEQUENCE: 28

```
ggcatcaatg tagatagcgg cagtgtacaa agtgacatta gttccagtag cagcttcctc     60
tcaacaagct cgtcttcggc cagttactct caggcatcag cttcttcgag cagcggtgcc    120
ggatacacag gaccttctgg accttccact ggaccgtctg gctaccctgg gcctttgagt    180
ggcggagcgt cgttcggctc tggccaatct tctttcggtc aaacttcagc cttttccgca    240
tctggtgctg acaatcggc tggagtatct gttatatctt ctcttaattc acccgttgga    300
ttgaggtctc cttctgctgc ttctagactt agtcaattaa catcatccat aacgaatgca    360
gttggtgcca atggtgttga tgctaattct cttgcccgta gtcttcaatc tagtttctcg    420
gcactcagaa gctccggcat gtcttcaagc gatgctaaaa ttgaagtatt gttggaaacc    480
attgttggtc tgcttcagct tttgagcaac actcaagtcc gaggagtaaa cccggcaacg    540
gcttcttcag tagcaaattc tgctgcgaga tcttttgaat tagttttggc ttaagagata    600
ttgattgtta gacctggaga taatgtaac ttttctgata tgcaatttgc atacgaaatt    660
tcttattaaa taaagcatt ttgaaacatt aaaaaaaaaa aaaaaaaaa                709
```

```
<210> SEQ ID NO 29
<211> LENGTH: 447
<212> TYPE: PRT
<213> ORGANISM: Argiope aurantia
<220> FEATURE:
<221> NAME/KEY: misc_feature
<222> LOCATION: (340)
<223> OTHER INFORMATION: Xaa = Pro or Ser
<220> FEATURE:
<221> NAME/KEY: misc_feature
<222> LOCATION: (440)
<223> OTHER INFORMATION: Xaa = Asn or Ser
```

<400> SEQUENCE: 29

```
Ala Gly Gln Gly Gly Ala Gly Ala Ala Ala Ala Ala Ala Ala Gly
 1               5                  10                  15

Gly Ala Gly Gly Ala Gly Arg Gly Gly Leu Gly Ala Gly Gly Ala Gly
            20                  25                  30

Gln Gly Tyr Gly Ser Gly Leu Gly Gly Gln Gly Gly Ala Gly Gly Gly
        35                  40                  45

Ala Ala Ala Ala Ala Ala Ala Ala Gly Gly Gln Gly Gly Gln Gly
    50                  55                  60

Gly Tyr Gly Gly Leu Gly Ser Gln Gly Ala Gly Gln Gly Gly Tyr Gly
65                  70                  75                  80

Ala Gly Gln Gly Gly Ala Gly Ala Ala Ala Ala Ala Ala Ala Gly
                85                  90                  95

Gly Ala Gly Gly Ala Gly Arg Gly Gly Leu Gly Ala Gly Gly Ala Gly
            100                 105                 110

Gln Gly Tyr Gly Ser Gly Leu Gly Gly Gln Gly Gly Ala Gly Gln Gly
        115                 120                 125

Gly Ala Ala Ala Ala Ala Ala Ala Gly Gly Gln Gly Gly Gln Gly
    130                 135                 140

Gly Tyr Gly Gly Leu Gly Ser Gln Gly Ala Gly Gln Gly Gly Ala Gly
145                 150                 155                 160

Arg Gly Ala Ala Ala Ala Ala Ala Ala Ala Gly Gly Gln Gly Gly Arg
                165                 170                 175

Gly Gly Tyr Gly Gly Leu Gly Ser Gln Gly Ala Gly Gln Gly Gly Tyr
            180                 185                 190
```

Gly Ala Gly Gln Gly Gly Ala Gly Ala Ala Ala Ala Ala Ala
        195                 200                 205

Gly Gly Ala Gly Glu Gly Gly Leu Gly Ala Gly Ala Gly Gln Gly
        210                 215                 220

Tyr Gly Ser Gly Leu Gly Gly Gln Gly Gly Ala Gly Gln Gly Ala
225                 230                 235                 240

Ala Ala Ala Ala Ala Ala Ala Gly Gly Gln Gly Gly His Gly Tyr
                245                 250                 255

Gly Gly Leu Gly Ser Gln Gly Ala Gln Gly Gly Ala Gly Arg Gly
            260                 265                 270

Ala Ala Ala Ala Ala Ala Ala Gly Gly Gln Gly Gly Gln Gly Gly
        275                 280                 285

Tyr Gly Gly Leu Gly Ser Gln Gly Ala Gly Gln Gly Gly Tyr Gly Ala
        290                 295                 300

Gly Gln Gly Gly Ala Ala Ala Ala Ala Ala Ala Ala Gly Gly
305                 310                 315                 320

Ala Gly Gly Ala Gly Arg Gly Glu Leu Gly Ala Gly Ala Gly Gln
                325                 330                 335

Gly Tyr Gly Xaa Gly Leu Gly Gln Gly Gly Ala Gly Gln Arg Gly
            340                 345                 350

Ala Ala Ser Val Ala Ala Leu Ala Gly Gln Gly Gly Gln Gly Gly
        355                 360                 365

Phe Gly Gly Phe Ser Ser Gln Gly Ala Gly Gln Gly Ala Tyr Gly Gly
        370                 375                 380

Gly Ala Tyr Ser Gly Gln Gly Ala Ala Ser Val Ser Ala Ala Ser
385                 390                 395                 400

Ala Ala Ala Ser Arg Leu Ser Ser Pro Gly Ala Ala Ser Arg Val Ser
                405                 410                 415

Ser Ala Val Thr Ser Leu Val Ser Ser Gly Pro Thr Asn Pro Ala
            420                 425                 430

Ala Leu Ser Asn Thr Ile Ser Xaa Val Val Ser Gln Ile Ser Glu
        435                 440                 445

<210> SEQ ID NO 30
<211> LENGTH: 648
<212> TYPE: PRT
<213> ORGANISM: Argiope trifasciata

<400> SEQUENCE: 30

Ala Ala Ala Ala Ala Ala Ala Ala Gly Gly Gln Gly Gly Gln Gly
 1               5                  10                  15

Gly Tyr Asp Gly Leu Gly Ser Gln Gly Ala Gly Gln Gly Gly Tyr Gly
            20                  25                  30

Gln Gly Gly Ala Ala Ala Ala Ala Ala Ala Ser Gly Ala Gly Ser
        35                  40                  45

Ala Gln Arg Gly Gly Leu Gly Ala Gly Ala Gly Gln Gly Tyr Gly
    50                  55                  60

Ala Gly Ser Gly Gly Gln Gly Gly Ala Gly Gln Gly Gly Ala Ala Ala
65                  70                  75                  80

Ala Thr Ala Ala Ala Gly Gly Gln Gly Gly Gln Gly Gly Tyr Gly
            85                  90                  95

Gly Leu Gly Ser Gln Gly Ser Gly Gln Gly Gly Tyr Gly Gln Gly Gly
            100                 105                 110

Ala Ala Ala Ala Ala Ala Ala Ala Ser Gly Asp Gly Gly Ala Gly Gln
        115                 120                 125

-continued

```
Glu Gly Leu Gly Ala Gly Ala Gly Gln Gly Tyr Gly Ala Gly Leu
    130                 135                 140
Gly Gly Gln Gly Gly Ala Gly Gln Gly Gly Ala Ala Ala Ala Ala
145                 150                 155                 160
Ala Ala Ala Gly Gly Gln Gly Gln Gly Gly Tyr Gly Gly Leu Gly
                165                 170                 175
Ser Gln Gly Ala Gly Gln Gly Tyr Gly Gln Gly Gly Ala Ala Ala
            180                 185                 190
Ala Ala Ala Ala Ala Ser Gly Ala Gly Ala Gly Gln Gly Gly Leu
            195                 200                 205
Gly Ala Ala Gly Ala Gly Gln Gly Tyr Gly Ala Gly Ser Gly Gly Gln
    210                 215                 220
Gly Gly Ala Gly Gln Gly Gly Ala Ala Ala Ala Ala Ala Ala Ala
225                 230                 235                 240
Gly Gly Gln Gly Gly Gln Gly Gly Tyr Gly Gly Leu Gly Ser Gln Gly
                245                 250                 255
Ala Gly Gln Gly Gly Tyr Gly Gln Gly Gly Val Ala Ala Ala Ala
            260                 265                 270
Ala Ala Ser Gly Ala Gly Gly Ala Gly Arg Gly Gly Leu Gly Ala Gly
        275                 280                 285
Gly Ala Gly Gln Glu Tyr Gly Ala Val Ser Gly Gln Gly Gly Ala
    290                 295                 300
Gly Gln Gly Gly Glu Ala Ala Ala Ala Ala Ala Ala Gly Gly Gln
305                 310                 315                 320
Gly Gly Gln Gly Gly Tyr Gly Gly Leu Gly Ser Gln Gly Ala Gly Gln
                325                 330                 335
Gly Gly Tyr Gly Gln Gly Gly Ala Ala Ala Ala Ala Ala Ala Ser
            340                 345                 350
Gly Ala Gly Gly Ala Arg Arg Gly Gly Leu Gly Ala Gly Gly Ala Gly
        355                 360                 365
Gln Gly Tyr Gly Ala Gly Leu Gly Gly Gln Gly Gly Ala Gly Gln Gly
    370                 375                 380
Ser Ala Ser Ala Ala Ala Ala Ala Ala Gly Gly Gln Gly Gly Gln
385                 390                 395                 400
Gly Gly Tyr Gly Gly Leu Gly Ser Gln Gly Ser Gly Gln Gly Gly Tyr
                405                 410                 415
Gly Gln Gly Gly Ala Ala Ala Ala Ala Ala Ala Ser Gly Ala Gly
            420                 425                 430
Gly Ala Gly Arg Gly Ser Leu Gly Ala Gly Gly Ala Gly Gln Gly Tyr
        435                 440                 445
Gly Ala Gly Leu Gly Gly Gln Gly Gly Ala Gly Gln Gly Gly Ala Ala
    450                 455                 460
Ala Ala Ala Ser Ala Ala Ala Gly Gly Gln Gly Gly Gln Gly Gly Tyr
465                 470                 475                 480
Gly Gly Leu Gly Ser Gln Gly Ala Gly Gln Gly Gly Tyr Gly Gln Gly
                485                 490                 495
Gly Ala Ala Ala Ala Ala Ala Ser Ala Gly Gly Gln Gly Gly Gln Gly
            500                 505                 510
Gly Tyr Gly Gly Leu Gly Ser Gln Gly Ala Gly Gln Gly Gly Tyr Gly
        515                 520                 525
Gly Gly Ala Phe Ser Gly Gln Gln Gly Gly Ala Ala Ser Val Ala Thr
    530                 535                 540
```

```
Ala Ser Ala Ala Ala Ser Arg Leu Ser Ser Pro Gly Ala Ala Ser Arg
545                 550                 555                 560

Val Ser Ser Ala Val Thr Ser Leu Val Ser Ser Gly Gly Pro Thr Asn
            565                 570                 575

Ser Ala Ala Leu Ser Asn Thr Ile Ser Asn Val Val Ser Gln Ile Ser
            580                 585                 590

Ser Ser Asn Pro Gly Leu Ser Gly Cys Asp Val Leu Val Gln Ala Leu
        595                 600                 605

Leu Glu Ile Val Ser Ala Leu Val His Ile Leu Gly Ser Ala Asn Ile
    610                 615                 620

Gly Gln Val Asn Ser Ser Gly Val Gly Arg Ser Ala Ser Ile Val Gly
625                 630                 635                 640

Gln Ser Ile Asn Gln Ala Phe Ser
                645

<210> SEQ ID NO 31
<211> LENGTH: 360
<212> TYPE: PRT
<213> ORGANISM: Latrodectus geometricus

<400> SEQUENCE: 31

Ala Gly Ser Gly Gln Gly Gly Tyr Gly Gln Gly Tyr Gly Glu Gly Gly
1               5                   10                  15

Ala Gly Gln Gly Gly Ala Gly Ala Ala Ala Ala Ala Ala Ala Ala Ala
                20                  25                  30

Gly Gly Ala Gly Gln Gly Gly Gln Gly Gly Tyr Gly Gln Gly Tyr Gly
            35                  40                  45

Gln Gly Gly Ala Gly Gln Gly Gly Ala Gly Ala Ala Ala Ala Ala Ala
        50                  55                  60

Ala Gly Gly Ala Gly Gln Gly Gly Tyr Gly Arg Gly Gly Ala Gly Gln
65                  70                  75                  80

Gly Ala Ala Ala Ala Ala Ala Ala Gly Ser Gly Gln Gly Gly Tyr Gln
                85                  90                  95

Gly Gly Tyr Gly Gln Gly Tyr Gly Gln Gly Gly Ala Gly Gln Gly Gly
            100                 105                 110

Ala Gly Ala Ala Ala Ala Ala Ala Ala Gly Gly Ala Gly Gln Gly Gly
        115                 120                 125

Gly Tyr Gly Arg Gly Gly Ala Gly Gln Gly Gly Ala Ala Ala Ala Ala
    130                 135                 140

Ala Ala Ala Gly Gly Ala Gly Gln Gly Gly Gly Gly Tyr Gly Gln Gly
145                 150                 155                 160

Gly Tyr Gly Gln Gly Gly Ala Gly Gln Gly Gly Ala Gly Ala Ala Ala
                165                 170                 175

Ala Ala Ala Ala Gly Gly Ala Gly Gln Gly Gly Tyr Gly Arg Gly Gly
            180                 185                 190

Gly Ala Gly Gln Gly Gly Ser Ala Ala Ala Ala Ala Ala Ala Gly Gly
        195                 200                 205

Ala Gly Gln Gly Gly Tyr Gly Arg Gly Gly Ala Gly Gln Gly Gly Ala
    210                 215                 220

Gly Ser Ala Ala Ala Ala Ala Ala Gly Gly Ser Gly Gln Gly Gly Gly
225                 230                 235                 240

Gln Gly Gly Tyr Gly Gln Gly Tyr Gly Gln Gly Gly Ala Gly Gln Gly
                245                 250                 255

Gly Ala Ala Ala Ala Ala Ser Ala Leu Ala Ala Pro Ala Thr Ser Ala
            260                 265                 270
```

```
Arg Ile Ser Ser His Ala Ser Thr Leu Leu Ser Asn Gly Pro Thr Asn
        275                 280                 285

Pro Ala Ser Ile Ser Asn Val Ile Ser Asn Ala Val Ser Gln Ile Ser
        290                 295                 300

Ser Ser Asn Pro Gly Ala Ser Ser Cys Asp Val Leu Val Gln Ala Leu
305                 310                 315                 320

Leu Glu Leu Val Thr Ala Leu Leu Thr Ile Ile Gly Ser Ser Asn Val
                325                 330                 335

Gly Asn Val Asn Tyr Asp Ser Ser Gly Gln Tyr Ala Gln Val Val Ser
                340                 345                 350

Gln Ser Val Gln Asn Ala Phe Val
        355                 360

<210> SEQ ID NO 32
<211> LENGTH: 233
<212> TYPE: PRT
<213> ORGANISM: Nephila madagascariensis

<400> SEQUENCE: 32

Gly Leu Gly Gly Gln Gly Ala Gly Gln Gly Ala Gly Ala Ala Ala Ala
1               5                   10                  15

Ala Ala Gly Gly Ala Gly Gln Gly Gly Tyr Gly Gly Leu Gly Ser Gln
                20                  25                  30

Gly Ala Gly Arg Gly Gly Tyr Gly Gly Gln Gly Ala Gly Ala Ala Ala
            35                  40                  45

Ala Ala Ala Ala Gly Gly Ala Gly Gln Gly Gly Tyr Gly Gly Leu Gly
        50                  55                  60

Ser Gln Gly Ala Gly Gln Gly Gly Tyr Gly Gly Leu Gly Gly Gln Gly
65                  70                  75                  80

Ala Gly Gln Gly Ala Ala Ala Ala Ala Ala Gly Gly Ala Gly Ala Gln
                85                  90                  95

Gly Gly Tyr Gly Gly Leu Gly Ser Gln Gly Ala Gly Arg Gly Gly Tyr
            100                 105                 110

Gly Gly Gln Gly Ala Gly Ala Ala Ala Ala Thr Gly Gly Ala Gly Gln
        115                 120                 125

Gly Gly Tyr Gly Gly Val Gly Ser Gly Ala Ser Ala Ala Ser Ala
        130                 135                 140

Ala Ala Ser Arg Leu Ser Ser Pro Gln Ala Ser Ser Arg Val Ser Ser
145                 150                 155                 160

Ala Val Ser Asn Leu Val Ala Ser Gly Pro Thr Asn Ser Ala Ala Leu
                165                 170                 175

Ser Ser Thr Ile Ser Asn Ala Val Ser Gln Ile Gly Ala Ser Asn Pro
                180                 185                 190

Gly Leu Ser Gly Cys Asp Val Leu Ile Gln Ala Leu Leu Glu Val Val
            195                 200                 205

Ser Ala Leu Ile His Ile Leu Gly Ser Ser Ser Ile Gly Gln Val Asn
        210                 215                 220

Tyr Gly Ser Ala Gly Gln Ala Thr Gln
225                 230

<210> SEQ ID NO 33
<211> LENGTH: 253
<212> TYPE: PRT
<213> ORGANISM: Nephila senegalensis

<400> SEQUENCE: 33
```

Gly Leu Gly Gly Gln Gly Ala Gly Arg Gly Ala Gly Ala Ala Ala
1               5                   10                  15

Ala Ala Gly Gly Ala Gly Gln Gly Gly Tyr Gly Gly Leu Gly Gly Gln
            20                  25                  30

Gly Ala Gly Ala Ala Ala Ala Ala Gly Gly Ala Gly Gln Gly Gly
        35                  40                  45

Gln Gly Leu Gly Gly Arg Gly Ala Ala Ala Gly Gly Ala Gly Gln
    50                  55                  60

Gly Gly Tyr Gly Gly Leu Gly Gly Gln Gly Ala Gly Arg Gly Ala Gly
65                  70                  75                  80

Ala Ala Ala Ala Ala Ala Gly Gly Ala Gly Gln Gly Gly Tyr Gly Gly
                85                  90                  95

Leu Gly Gly Gln Gly Ala Gly Ala Ala Ala Ala Ala Ala Ala Gly
            100                 105                 110

Gly Ala Gly Gln Gly Gly Tyr Gly Gly Leu Gly Ser Gln Gly Ala Gly
        115                 120                 125

Arg Gly Gly Tyr Gly Gly Gln Gly Ala Gly Ala Ala Val Ala Ala Ile
    130                 135                 140

Gly Gly Val Gly Gln Gly Gly Tyr Gly Gly Val Gly Ser Gly Ala Ser
145                 150                 155                 160

Ala Ala Ser Ala Ala Ala Ser Arg Leu Ser Ser Pro Glu Ala Ser Ser
                165                 170                 175

Arg Val Ser Ser Ala Val Ser Asn Leu Val Ser Ser Gly Pro Thr Asn
            180                 185                 190

Ser Ala Ala Leu Ser Ser Thr Ile Ser Asn Val Val Ser Gln Ile Gly
        195                 200                 205

Ala Ser Asn Pro Gly Leu Ser Gly Cys Asp Val Leu Ile Gln Ala Leu
    210                 215                 220

Leu Glu Val Val Ser Ala Leu Val His Ile Leu Gly Ser Ser Ser Ile
225                 230                 235                 240

Gly Gln Val Asn Tyr Gly Ser Ala Gly Gln Ala Thr Gln
                245                 250

<210> SEQ ID NO 34
<211> LENGTH: 284
<212> TYPE: PRT
<213> ORGANISM: Tetragnatha kauaiensis
<220> FEATURE:
<221> NAME/KEY: misc_feature
<222> LOCATION: (23)
<223> OTHER INFORMATION: Xaa = Ala or Gly

<400> SEQUENCE: 34

Ser Gly Leu Gly Gly Ala Gly Gln Gly Ala Gly Gln Gly Ala Ser Ala
1               5                   10                  15

Ala Ala Ala Ala Ala Ala Xaa Gly Gly Leu Gly Gly Gln Gly Ala
            20                  25                  30

Gly Gln Gly Gly Gln Gln Gly Ala Gly Gln Gly Gly Tyr Gly Ser Gly
        35                  40                  45

Leu Gly Gly Ala Gly Gln Gly Ala Ser Ala Ala Ala Ala Ala Ala
    50                  55                  60

Ala Gly Gly Leu Gly Gly Gly Gln Gly Ala Gln Gly Gly Gln Gln
65                  70                  75                  80

Gly Ala Gly Gln Gly Gly Tyr Gly Ser Gly Leu Gly Gly Ala Gly Gln
                85                  90                  95

```
Gly Ala Ser Ala Ala Ala Ala Ala Ala Ala Gly Gly Leu Gly Gly
            100                 105                 110

Gly Gln Gly Ala Gly Gln Gly Gln Gln Gly Ala Gly Gln Gly Gly
            115                 120                 125

Tyr Gly Ser Gly Leu Gly Gly Ala Gly Gln Gly Ala Gln Gly Ala
            130                 135                 140

Ser Ala Ala Ala Ala Ala Ala Gly Gly Leu Gly Gly Gly Gln Gly
145                 150                 155                 160

Gly Tyr Gly Ser Gly Leu Gly Gly Val Gly Gln Gly Gln Gly Ala
                165                 170                 175

Leu Gly Gly Ser Arg Asn Ser Ala Thr Asn Ala Ile Ser Asn Ser Ala
            180                 185                 190

Ser Asn Ala Val Ser Leu Leu Ser Ser Pro Ala Ser Asn Ala Arg Ile
            195                 200                 205

Ser Ser Ala Val Ser Ala Leu Ala Ser Gly Ala Ala Ser Gly Pro Gly
        210                 215                 220

Tyr Leu Ser Ser Val Ile Ser Asn Val Val Ser Gln Val Ser Ser Asn
225                 230                 235                 240

Ser Gly Gly Leu Val Gly Cys Asp Thr Leu Val Gln Ala Leu Leu Glu
            245                 250                 255

Ala Ala Ala Ala Leu Val His Val Leu Ala Ser Ser Ser Gly Gly Gln
            260                 265                 270

Val Asn Leu Asn Thr Ala Gly Tyr Thr Ser Gln Leu
            275                 280

<210> SEQ ID NO 35
<211> LENGTH: 178
<212> TYPE: PRT
<213> ORGANISM: Tetragnatha versicolor

<400> SEQUENCE: 35

Ser Gly Gln Gly Ala Ser Ala Ala Ala Ala Gly Gly Leu Gly
 1                  5                  10                 15

Gly Gly Gln Gly Gly Tyr Gly Ser Gly Leu Gly Gly Ala Gly Gln Gly
                20                 25                  30

Gly Gln Gln Gly Ala Gly Gln Gly Ala Ala Ala Ala Ala Ser Ala
            35                  40                  45

Ala Ala Gly Gly Leu Gly Gly Gly Gln Gly Gly Gln Gln Gly Ala Gly
        50                  55                  60

Arg Gly Gly Leu Gln Gly Ala Gly Gln Gly Gly Gln Gly Ala Leu Gly
65                  70                  75                  80

Gly Ser Arg Asn Ser Ala Ala Asn Ala Val Ser Arg Leu Ser Ser Pro
                85                  90                  95

Ala Ser Asn Ala Arg Ile Ser Ser Ala Val Ser Ala Leu Ala Ser Gly
            100                 105                 110

Gly Ala Ser Ser Pro Gly Tyr Leu Ser Ser Ile Ile Ser Asn Val Val
        115                 120                 125

Ser Gln Val Ser Ser Asn Asn Asp Gly Leu Ser Gly Cys Asp Thr Val
    130                 135                 140

Val Gln Ala Leu Leu Glu Val Ala Ala Ala Leu Val His Val Leu Ala
145                 150                 155                 160

Ser Ser Asn Ile Gly Gln Val Asn Leu Asn Thr Ala Gly Tyr Thr Ser
                165                 170                 175

Gln Leu
```

<210> SEQ ID NO 36
<211> LENGTH: 349
<212> TYPE: PRT
<213> ORGANISM: Argiope aurantia
<220> FEATURE:
<221> NAME/KEY: misc_feature
<222> LOCATION: (39)
<223> OTHER INFORMATION: Xaa = Asp or Gly

<400> SEQUENCE: 36

Pro Gly Gly Ala Gly Gln Gly Pro Gly Gln Gly Pro Tyr Gly
1               5                   10                  15

Pro Gly Ala Ala Ala Ala Ala Ala Gly Gly Tyr Gly Pro Gly
                20                  25                  30

Ala Gly Gln Gln Gly Pro Xaa Gly Ala Gly Gln Gly Pro Gly Ser
                35                  40                  45

Gln Gly Pro Gly Gly Ala Gly Gln Gln Gly Pro Gly Gly Gln Gly Pro
    50                  55                  60

Tyr Gly Pro Gly Ala Ala Ala Ala Ala Val Gly Gly Tyr Gly
65                  70                  75                  80

Pro Gly Ala Gly Gln Gln Gly Pro Gly Ser Gln Gly Pro Gly Ser Gly
                85                  90                  95

Gly Gln Gln Gly Pro Gly Gly Gln Gly Pro Tyr Gly Pro Ser Ala Ala
                100                 105                 110

Ala Ala Ala Ala Ala Gly Gly Tyr Gly Pro Gly Ala Gly Gln Gln
                115                 120                 125

Gly Pro Gly Ser Gln Gly Pro Gly Ser Gly Gly Gln Gln Gly Pro Gly
    130                 135                 140

Gly Leu Gly Pro Tyr Gly Pro Ser Ala Ala Ala Ala Ala Ala
145                 150                 155                 160

Gly Gly Tyr Gly Pro Gly Ala Gly Gln Gln Gly Pro Gly Ser Gln Gly
                165                 170                 175

Pro Gly Ser Gly Gly Gln Gln Arg Pro Gly Gly Leu Gly Pro Tyr Gly
    180                 185                 190

Pro Ser Ala Ala Ala Ala Ala Ala Ala Gly Gly Tyr Gly Pro Gly
                195                 200                 205

Ala Gly Gln Gln Gly Pro Gly Ser Gln Gly Pro Gly Ser Gly Gly Gln
    210                 215                 220

Gln Arg Pro Gly Gly Leu Gly Pro Tyr Gly Pro Ser Ala Ala Ala Ala
225                 230                 235                 240

Ala Ala Ala Ala Gly Gly Tyr Gly Pro Gly Ala Gly Gln Gln Gly Pro
                245                 250                 255

Gly Ser Gln Ala Pro Val Ala Ser Ala Ala Ser Arg Leu Ser Ser
                260                 265                 270

Pro Gln Ala Ser Ser Arg Val Ser Ser Ala Val Ser Thr Leu Val Ser
    275                 280                 285

Ser Gly Pro Thr Asn Pro Ala Ala Leu Ser Asn Ala Ile Ser Ser Val
    290                 295                 300

Val Ser Gln Val Ser Ala Ser Asn Pro Gly Leu Ser Gly Cys Asp Val
305                 310                 315                 320

Leu Val Gln Ala Leu Leu Glu Leu Val Ser Ala Leu Val His Ile Leu
                325                 330                 335

Gly Ser Ser Ser Ile Gly Gln Ile Asn Tyr Ala Ala Ser
                340                 345

```
<210> SEQ ID NO 37
<211> LENGTH: 444
<212> TYPE: PRT
<213> ORGANISM: Argiope trifasciata

<400> SEQUENCE: 37

Ala Gly Pro Gly Tyr Gly Pro Gly Ala Gly Gln Gln Gly Pro Gly Ser
 1               5                  10                  15

Gln Gly Pro Gly Ser Gly Gln Gln Gly Pro Gly Gly Gln Gly Pro
            20                  25                  30

Tyr Gly Pro Ser Ala Ala Ala Ala Ala Ala Gly Pro Gly Tyr
            35                  40                  45

Gly Pro Gly Ala Gly Gln Gln Gly Pro Gly Ser Gly Gln Gln Gly
        50                  55                  60

Gly Gln Gly Ser Gly Gln Gln Gly Pro Gly Gly Ala Gln Gly Gly
 65                  70                  75                  80

Pro Arg Gly Gln Gly Pro Tyr Gly Pro Gly Ala Ala Ala Ala
                85                  90                  95

Ala Ala Gly Gly Tyr Gly Pro Gly Ala Gly Gln Gln Gly Pro Gly Ser
            100                 105                 110

Gln Gly Pro Gly Ser Gly Gly Gln Gln Gly Pro Gly Ser Gln Gly Pro
            115                 120                 125

Tyr Gly Pro Ser Ala Ala Ala Ala Ala Ala Ala Gly Pro Gly Tyr
            130                 135                 140

Gly Pro Gly Ala Gly Gln Gln Gly Pro Gly Ser Gln Gly Pro Gly Ser
145                 150                 155                 160

Gly Gly Gln Gln Gly Pro Gly Gly Gln Gly Pro Tyr Gly Pro Ser Asp
                165                 170                 175

Ala Ala Ala Ala Ala Ala Gly Pro Gly Tyr Gly Pro Gly Ala Gly
            180                 185                 190

Gln Gln Gly Pro Gly Ser Gly Gln Gln Gly Gly Gln Gly Ser Gly
            195                 200                 205

Gln Gln Gly Pro Gly Gly Ala Gly Gln Gly Gly Pro Arg Gly Gln Gly
            210                 215                 220

Pro Tyr Gly Pro Gly Ala Ala Ala Ala Ala Ala Ala Gly Gly Tyr
225                 230                 235                 240

Gly Pro Gly Ala Gly Gln Gln Gly Pro Gly Ser Gln Gly Pro Gly Ser
                245                 250                 255

Gly Gly Gln Gln Gly Pro Gly Ser Gln Gly Pro Tyr Gly Pro Ser Ala
            260                 265                 270

Ala Ala Ala Ala Ala Ala Gly Pro Gly Tyr Gly Pro Gly Ala Gly
            275                 280                 285

Gln Gln Gly Pro Gly Ser Gln Gly Pro Gly Ser Gly Gly Gln Gln Gly
            290                 295                 300

Pro Gly Ser Gln Gly Pro Tyr Gly Pro Ser Ala Ala Ala Ala Ala
305                 310                 315                 320

Ala Ala Gly Pro Gly Tyr Gly Pro Gly Ala Gly Gln Gln Gly Pro Gly
                325                 330                 335

Ser Gln Ala Pro Val Ala Ser Ala Ala Ala Ser Arg Leu Ser Ser Pro
            340                 345                 350

Gln Ala Ser Ser Arg Val Ser Ser Ala Val Ser Thr Leu Val Ser Ser
            355                 360                 365

Gly Pro Thr Asn Pro Ala Ser Leu Ser Asn Ala Ile Ser Ser Val Val
            370                 375                 380
```

```
Ser Gln Val Ser Ser Asn Pro Gly Leu Ser Gly Cys Asp Val Leu
385                 390                 395                 400

Val Gln Ala Leu Leu Glu Ile Val Ser Ala Leu Val His Ile Leu Gly
                405                 410                 415

Ser Ser Ser Ile Gly Gln Ile Asn Tyr Ala Ala Ser Ser Gln Tyr Ala
            420                 425                 430

Gln Leu Val Gly Gln Ser Leu Thr Gln Ala Leu Gly
            435                 440
```

<210> SEQ ID NO 38
<211> LENGTH: 120
<212> TYPE: PRT
<213> ORGANISM: Argiope trifasciata

<400> SEQUENCE: 38

```
Gly Pro Gly Gln Gln Gly Pro Gly Gly Tyr Gly Thr Ser Gly Pro Gly
1               5                   10                  15

Gly Ala Ser Ala Ala Ala Ala Ala Ala Gly Gly Pro Gly Gly
            20                  25                  30

Gln Gly Pro Ser Gly Pro Gly Pro Gly Pro Gly Gly Tyr Gly Pro
            35                  40                  45

Ser Gly Pro Gly Ala Ala Ala Ala Ala Ala Ala Ala Gly Gly Pro
            50                  55                  60

Gly Ser Gln Gly Pro Gly Gln Gln Pro Gly Gly Tyr Gly Pro Ser
65                  70                  75                  80

Gly Pro Gly Gly Ala Ser Ala Ala Ala Ala Ala Ala Gly Gly
                85                  90                  95

Pro Gly Gly Gln Gly Ser Tyr Gly Pro Gly Gln Gln Gly Pro Gly Ala
                100                 105                 110

Gly Gln Tyr Gly Pro Gly Gln Gln
            115                 120
```

<210> SEQ ID NO 39
<211> LENGTH: 342
<212> TYPE: PRT
<213> ORGANISM: Gasteracantha mammosa

<400> SEQUENCE: 39

```
Gly Gln Gln Gly Pro Gly Ser Gln Gly Pro Tyr Gly Pro Gly Ala Ala
1               5                   10                  15

Ala Ala Ala Ala Ala Ala Gly Gly Tyr Arg Pro Val Ser Gly Gln
            20                  25                  30

Gln Gly Pro Gly Gln Gln Gly Pro Ser Gly Gly Gln Gln Gly Pro
            35                  40                  45

Gly Gly Gln Arg Pro Tyr Gly Pro Gly Ala Ala Ala Ala Ala Ala
            50                  55                  60

Ala Gly Gly Tyr Gly Pro Gly Ser Gly Gln Gly Gly Pro Gly Gln Gln
65                  70                  75                  80

Gly Pro Gly Ser Gly Gln Gln Gly Pro Gly Gln Gly Pro Tyr
                85                  90                  95

Gly Pro Gly Ala Ala Ala Ala Ala Ala Ala Ala Gly Gly Tyr Gly
                100                 105                 110

Pro Gly Ser Gly Gln Gly Gln Gln Gly Pro Gly Ser Gln Gly Pro
            115                 120                 125

Gly Ser Gly Gly Gln Gln Gly Gly Gln Gly Pro Tyr Gly Pro
            130                 135                 140
```

-continued

```
Ser Ala Ala Ala Ala Ala Ala Val Gly Gly Tyr Gly Pro Gly Ala
145                 150                 155                 160

Gly Gln Gln Gly Pro Gly Gln Gly Pro Gly Ser Gly Gly Gln Arg
                165                 170                 175

Gly Pro Gly Gly Gln Gly Pro Tyr Gly Pro Gly Ala Ala Ala Ala
            180                 185                 190

Ala Ala Ala Ala Gly Gly Tyr Gly Pro Ala Ser Gly Gln Gln Gly Pro
        195                 200                 205

Gly Gln Gln Gly Pro Gly Ser Gly Gly Gln Arg Gly Pro Gly Gly Gln
    210                 215                 220

Gly Pro Tyr Gly Pro Gly Ala Ala Ala Ala Ser Ala Gly Gly Tyr
225                 230                 235                 240

Gly Pro Gly Ser Gly Ser Pro Ala Ser Gly Ala Ala Ser Arg Leu
                245                 250                 255

Ser Ser Pro Gln Ala Gly Ala Arg Val Ser Ser Ala Val Ser Ala Leu
                260                 265                 270

Val Ala Ser Gly Pro Thr Ser Pro Ala Ala Val Ser Ser Ala Ile Ser
    275                 280                 285

Asn Val Ala Ser Gln Ile Ser Ala Ser Asn Pro Gly Leu Ser Gly Cys
    290                 295                 300

Asp Val Leu Val Gln Ala Leu Leu Glu Ile Val Ser Ala Leu Val Ser
305                 310                 315                 320

Ile Leu Ser Ser Ala Ser Ile Gly Gln Ile Asn Tyr Gly Ala Ser Gly
                325                 330                 335

Gln Tyr Ala Ala Met Ile
            340

<210> SEQ ID NO 40
<211> LENGTH: 373
<212> TYPE: PRT
<213> ORGANISM: Latrodectus geometricus

<400> SEQUENCE: 40

Ala Ser Ala Ser Gly Gly Ala Gly Pro Gly Arg Gln Gln Gly Tyr Gly
  1               5                  10                  15

Pro Gly Gly Ser Gly Ala Ser Ala Ala Ala Ala Ala Ala Gly Gly
                20                  25                  30

Ala Gly Pro Gly Gly Tyr Gly Gln Gly Pro Ser Gly Tyr Gly Pro Ser
            35                  40                  45

Gly Pro Gly Ala Gln Gln Gly Tyr Gly Pro Gly Gly Gly Gly Ser
    50                  55                  60

Gly Ala Ala Ala Ala Ala Ala Ala Gly Ser Gly Pro Gly Gly
65                  70                  75                  80

Tyr Gly Pro Gly Ala Ala Gly Pro Gly Ser Tyr Gly Pro Ser Gly Pro
                85                  90                  95

Gly Gly Ser Gly Ala Ala Ala Ala Ala Ala Ser Gly Pro Gly
                100                 105                 110

Gly Gln Gln Gly Tyr Gly Pro Gly Pro Gly Ala Ser Ala Ala Ala
            115                 120                 125

Ala Ala Ala Ala Gly Gly Ser Gly Pro Gly Tyr Gly Gln Gly Pro
        130                 135                 140

Ser Gly Tyr Gly Pro Ser Gly Pro Gly Ala Gln Gln Gly Tyr Gly Pro
145                 150                 155                 160

Gly Gly Gln Gly Gly Ser Gly Ala Ala Ala Ala Ala Ala Ala Ala
                165                 170                 175
```

-continued

Gly Ser Gly Arg Gly Gly Tyr Gly Pro Gly Ala Ala Gly Pro Gly Asn
            180                 185                 190

Tyr Gly Pro Ser Gly Pro Gly Gly Ser Gly Ala Ala Ser Ala Ala
            195                 200                 205

Ala Ala Ser Gly Pro Gly Gly Gln Gln Gly Tyr Gly Pro Gly Gly Ser
    210                 215                 220

Gly Ala Ala Ala Ala Ala Ser Gly Gly Ala Gly Pro Gly Arg Gln
225                 230                 235                 240

Gln Gly Tyr Gly Pro Gly Gly Ser Gly Ala Ala Ala Ala Ala
            245                 250                 255

Ala Ala Gly Gly Ser Gly Pro Gly Gly Tyr Gly Gln Gly Pro Ala Gly
            260                 265                 270

Tyr Gly Pro Gly Gly Gln Gly Gly Ser Gly Gly Ala Ala Ala Ala Ala
            275                 280                 285

Ala Ala Ala Ser Ser Gly Pro Gly Gly Tyr Gly Pro Gly Ala Ala Gly
    290                 295                 300

Pro Gly Asn Tyr Gly Pro Ser Gly Pro Gly Gly Ser Gly Ala Ala Ala
305                 310                 315                 320

Ala Ala Ala Ala Ala Ser Gly Pro Gly Gly Gln Gln Gly Tyr Gly Pro
            325                 330                 335

Gly Gly Ser Gly Ala Ser Ala Ala Ala Ala Gly Gly Ala Gly Pro
            340                 345                 350

Gly Arg Gln Gln Ala Tyr Gly Pro Gly Gly Ser Gly Ala Ala Ala Ala
            355                 360                 365

Ala Ala Ser Gly Ser
    370

<210> SEQ ID NO 41
<211> LENGTH: 399
<212> TYPE: PRT
<213> ORGANISM: Latrodectus geometricus
<220> FEATURE:
<221> NAME/KEY: misc_feature
<222> LOCATION: (173)
<223> OTHER INFORMATION: Xaa = Ala ot Gly
<220> FEATURE:
<221> NAME/KEY: misc_feature
<222> LOCATION: (186)
<223> OTHER INFORMATION: Xaa = Thr, Ala, Ser, or Gly
<220> FEATURE:
<221> NAME/KEY: misc_feature
<222> LOCATION: (211)
<223> OTHER INFORMATION: Xaa = Glu or Gly
<220> FEATURE:
<221> NAME/KEY: misc_feature
<222> LOCATION: (267)
<223> OTHER INFORMATION: Xaa = Pro or Leu
<220> FEATURE:
<221> NAME/KEY: misc_feature
<222> LOCATION: (298)
<223> OTHER INFORMATION: Xaa = Pro or Ser

<400> SEQUENCE: 41

Ala Gly Pro Gly Ser Tyr Gly Pro Ser Gly Pro Gly Gly Ser Gly Ala
 1               5                  10                  15

Ala Ala Ala Ala Ala Ala Ser Gly Pro Gly Gly Gln Gln Gly Tyr
            20                  25                  30

Gly Pro Gly Gly Pro Gly Ala Ser Ala Ala Ala Ala Ala Ala Gly
        35                  40                  45

Gly Ser Gly Pro Gly Gly Tyr Gly Gln Gly Pro Ser Gly Tyr Gly Pro
    50                  55                  60

Ser Gly Pro Gly Ala Gln Gln Gly Tyr Gly Pro Gly Gln Gly Gly
65                  70                  75                  80

Ser Gly Ala Ala Ala Ala Ala Ala Ala Gly Ser Gly Pro Gly
            85                  90                  95

Gly Tyr Gly Pro Gly Ala Gly Pro Gly Asn Tyr Gly Pro Ser Gly
            100                 105                 110

Pro Gly Gly Ser Gly Ala Ala Ser Ala Ala Ala Ser Gly Pro
            115                 120                 125

Gly Gly Gln Gln Gly Tyr Gly Pro Gly Ser Gly Ala Ala Ala
    130                 135                 140

Ala Ala Ser Gly Gly Ala Gly Pro Gly Arg Gln Gln Gly Tyr Gly Pro
145                 150                 155                 160

Gly Gly Ser Gly Ala Ala Ala Ala Ala Ala Xaa Gly Gly Ser
            165                 170                 175

Gly Pro Gly Gly Tyr Gly Gln Gly Pro Xaa Gly Tyr Gly Pro Gly Gly
            180                 185                 190

Gln Gly Gly Ser Gly Gly Ala Ala Ala Ala Ala Ala Ser Ser
    195                 200                 205

Gly Pro Xaa Gly Tyr Gly Pro Gly Ala Ala Gly Pro Gly Asn Tyr Gly
    210                 215                 220

Pro Ser Gly Pro Gly Gly Ser Gly Ala Ala Ala Ala Ala Ala
225                 230                 235                 240

Ser Gly Pro Gly Gly Gln Gln Gly Tyr Gly Pro Gly Gly Ser Gly Ala
            245                 250                 255

Ser Ala Ala Ala Ala Gly Gly Ala Gly Xaa Gly Arg Gln Gln Ala
            260                 265                 270

Tyr Gly Pro Gly Gly Ser Gly Ala Ala Ala Ala Ala Ser Gly Ser
            275                 280                 285

Gly Gly Tyr Gly Pro Ala Gln Tyr Gly Xaa Ser Ser Val Ala Ser Ser
    290                 295                 300

Ala Ala Ser Ala Ala Ser Ala Leu Ser Ser Pro Thr Thr His Ala Arg
305                 310                 315                 320

Ile Ser Ser His Ala Ser Thr Leu Leu Ser Ser Gly Pro Thr Asn Ser
            325                 330                 335

Ala Ala Ile Ser Asn Val Ile Ser Asn Ala Val Ser Gln Val Ser Ala
            340                 345                 350

Ser Asn Pro Gly Ser Ser Cys Asp Val Leu Val Gln Ala Leu Leu
            355                 360                 365

Glu Leu Ile Thr Ala Leu Ile Ser Ile Val Asp Ser Ser Asn Ile Gly
            370                 375                 380

Gln Val Asn Tyr Gly Ser Ser Gly Gln Tyr Ala Gln Met Val Gly
385                 390                 395

<210> SEQ ID NO 42
<211> LENGTH: 1953
<212> TYPE: PRT
<213> ORGANISM: Nephila madagascariensis

<400> SEQUENCE: 42

Gly Ser Tyr Gly Gln Gly Pro Ser Gly Tyr Ala Gln Gly Ser Ser Ala
1               5                   10                  15

Ala Ser Ala Ala Ala Pro Ser Gly Tyr Val Pro Ser Gln Thr Gly Gln
            20                  25                  30

Ser Gly Leu Gly Ala Ala Ala Ala Ala Ala Val Ala Pro Ser Gly

-continued

```
                35                  40                  45
Tyr Gly Pro Ser Gln Gln Gly Pro Ser Gly Pro Gly Ala Ala Thr Ala
 50                  55                  60
Ala Ala Ala Gly Arg Gly Pro Glu Gly Tyr Gly Pro Arg Gln Gln Gly
 65                  70                  75                  80
Pro Gly Ala Thr Ala Ala Ala Gly Pro Gly Gly Tyr Gly Pro Arg
                 85                  90                  95
Gln Gln Gly Pro Gly Gly Tyr Gly Pro Gly Gln Gln Gly Pro Gly Ala
                100                 105                 110
Ala Ala Ala Ala Ala Ala Gly Arg Gly Pro Gly Gly Tyr Gly Pro Gly
                115                 120                 125
Gln Gln Gly Pro Gly Gly Pro Gly Ala Ala Ala Ala Ala Gly Ser
                130                 135                 140
Glu Gly Tyr Gly Pro Gly Gln Gln Gly Pro Arg Gly Pro Gly Ala Ala
145                 150                 155                 160
Ala Ala Gly Pro Gly Gly Tyr Gly Pro Gly Gln Gln Gly Ala Ser Ala
                165                 170                 175
Ala Ala Ser Ala Ala Ala Gly Arg Gly Pro Gly Gly Tyr Gly Pro Gly
                180                 185                 190
Gln Gln Gly Pro Gly Gly Pro Ser Ala Ala Ala Ala Gly Pro Gly Gly
                195                 200                 205
Tyr Gly Pro Gly Gln Gln Gly Pro Ser Ala Ala Ala Ala Ala Ala
210                 215                 220
Gly Ser Gly Pro Gly Gly Tyr Gly Pro Gly Gln Gln Gly Pro Gly Gly
225                 230                 235                 240
Pro Gly Ala Ala Ala Ala Ala Ala Gly Pro Gly Gly Tyr Gly Pro Gly
                245                 250                 255
Gln Gln Gly Pro Gly Ala Ala Ala Ala Ala Gly Arg Gly Pro Gly
                260                 265                 270
Gly Tyr Gly Pro Gly Gln Gln Gly Pro Gly Pro Gly Ala Ala Ala
                275                 280                 285
Ala Ala Ala Ala Gly Arg Gly Pro Gly Gly Tyr Gly Pro Gly Gln Gln
290                 295                 300
Gly Pro Gly Gly Pro Gly Ala Ala Ala Ala Ala Gly Pro Gly Gly
305                 310                 315                 320
Tyr Gly Pro Gly Gly Tyr Gly Pro Gly Gln Gln Gly Pro Gly Pro
                325                 330                 335
Gly Ala Ala Ala Ala Ala Ala Gly Arg Gly Pro Gly Gly Tyr Gly
                340                 345                 350
Pro Gly Gln Gln Gly Pro Gly Gln Gln Gly Pro Gly Gly Ser Gly Ala
                355                 360                 365
Ala Ala Ala Ala Gly Arg Gly Pro Gly Gly Tyr Gly Pro Gly Gln
                370                 375                 380
Gln Gly Pro Gly Gly Pro Gly Ala Ala Ala Ala Ala Gly Pro Gly
385                 390                 395                 400
Gly Tyr Gly Pro Gly Gln Gln Gly Pro Gly Ala Ala Ala Ala Ala
                405                 410                 415
Ala Ala Gly Arg Gly Pro Gly Gly Tyr Gly Pro Gly Gln Gln Gly Pro
                420                 425                 430
Gly Gly Pro Gly Ala Ala Ala Ala Ala Ala Gly Arg Gly Pro Gly
                435                 440                 445
Gly Tyr Gly Pro Gly Gln Gln Gly Pro Gly Gln Gln Gly Pro Gly Gly
                450                 455                 460
```

-continued

Ser Gly Ala Ala Ala Ala Ala Gly Arg Gly Pro Gly Gly Tyr Gly
465                 470                 475                 480

Pro Gly Gln Gln Gly Pro Gly Gly Pro Gly Ala Ala Ala Ala Ala
                485                 490                 495

Gly Pro Gly Gly Tyr Gly Pro Gly Gln Gln Gly Pro Gly Ala Ala
                500                 505                 510

Ala Ala Ala Ala Ala Gly Arg Gly Pro Gly Gly Tyr Gly Pro Gly Gln
            515                 520                 525

Gln Gly Pro Gly Gly Ser Gly Ala Ala Ala Ala Ala Gly Arg Gly
530                 535                 540

Pro Gly Gly Tyr Gly Pro Gly Gln Gln Gly Pro Gly Gly Pro Gly Ala
545                 550                 555                 560

Ala Ala Ala Ala Gly Pro Gly Gly Tyr Gly Pro Gly Gln Gln Gly
                565                 570                 575

Thr Gly Ala Ala Ala Ala Ala Ala Gly Ser Gly Ala Gly Gly Tyr
            580                 585                 590

Gly Pro Gly Gln Gln Gly Pro Gly Gly Pro Gly Ala Ala Ala Ala
        595                 600                 605

Ala Gly Pro Gly Gly Tyr Gly Pro Gly Gln Gln Gly Pro Gly Ala Ala
        610                 615                 620

Ala Ala Ala Ala Ala Gly Ser Gly Pro Gly Gly Tyr Gly Pro Gly Gln
625                 630                 635                 640

Gln Gly Pro Gly Gly Ser Ser Ala Ala Ala Ala Ala Gly Pro Gly
                645                 650                 655

Arg Tyr Gly Pro Gly Gln Gln Gly Pro Gly Ala Ala Ala Ala Ala Ser
            660                 665                 670

Ala Gly Arg Gly Pro Gly Gly Tyr Gly Pro Gly Gln Gln Gly Pro Gly
            675                 680                 685

Gly Pro Gly Ala Ala Ala Ala Ala Gly Pro Gly Gly Tyr Gly Pro
690                 695                 700

Gly Gln Gln Gly Pro Gly Ala Ala Ala Ala Ala Ala Gly Ser Gly
705                 710                 715                 720

Pro Gly Gly Tyr Gly Pro Gly Gln Gln Gly Pro Gly Pro Gly Ala
                725                 730                 735

Ala Ala Ala Ala Ala Gly Arg Gly Pro Gly Gly Tyr Gly Gln Gly
            740                 745                 750

Gln Gln Gly Pro Gly Gly Pro Gly Ala Ala Ala Ala Ala Gly Pro
            755                 760                 765

Gly Gly Tyr Gly Pro Gly Gln Gln Gly Pro Gly Ala Ala Ala Ala
            770                 775                 780

Ala Ala Gly Ser Gly Pro Gly Gly Tyr Gly Pro Gly Gln Gln Gly Pro
785                 790                 795                 800

Gly Arg Ser Gly Ala Ala Ala Ala Ala Ala Gly Arg Gly Pro
            805                 810                 815

Gly Gly Tyr Gly Pro Gly Gln Gln Gly Pro Gly Gly Pro Gly Ala Ala
            820                 825                 830

Ala Ala Ala Ala Gly Pro Gly Gly Tyr Gly Pro Gly Gln Gln Gly Pro
            835                 840                 845

Gly Ala Ala Ala Ala Ala Ser Ala Gly Arg Gly Pro Gly Gly Tyr Gly
            850                 855                 860

Pro Gly Gln Gln Gly Pro Gly Gly Ser Gly Ala Ala Ala Ala Ala Ala
865                 870                 875                 880

-continued

```
Gly Arg Gly Pro Gly Gly Tyr Gly Pro Gly Gln Gln Gly Pro Gly Gly
            885                 890                 895

Pro Gly Ala Ala Ala Ala Ala Ala Gly Arg Gly Pro Gly Gly Tyr
        900                 905                 910

Gly Pro Gly Gln Gln Gly Pro Gly Gln Gln Gly Pro Gly Gly Ser Gly
            915                 920                 925

Ala Ala Ala Ala Ala Ala Gly Arg Gly Pro Gly Gly Tyr Gly Pro Gly
        930                 935                 940

Gln Gln Gly Pro Gly Gly Pro Gly Ala Ala Ala Ala Ala Ala Gly Pro
945                 950                 955                 960

Gly Gly Tyr Gly Pro Gly Gln Gln Gly Pro Gly Ala Ala Ala Ala Ala
            965                 970                 975

Ala Ala Gly Ser Gly Pro Gly Gly Tyr Gly Pro Gly Gln Gln Gly Pro
            980                 985                 990

Gly Gly Pro Gly Ala Ala Ala Ala Ala Ala Gly Arg Gly Pro Gly Gly
            995                1000                1005

Tyr Gly Pro Gly Gln Gln Gly Pro Gly Gly Pro Gly Ala Ala Ala Ala
           1010                1015                1020

Ala Ala Ala Gly Arg Gly Pro Gly Gly Tyr Gly Pro Gly Gln Gln Gly
1025                1030                1035                1040

Pro Gly Gln Gln Gly Pro Gly Gly Ser Gly Ala Ala Ala Ala Ala Ala
           1045                1050                1055

Gly Arg Gly Pro Gly Gly Tyr Gly Pro Gly Gln Gln Gly Pro Gly Gly
           1060                1065                1070

Pro Gly Ala Ala Ala Ala Ala Ala Gly Pro Gly Gly Tyr Gly Pro Gly
           1075                1080                1085

Gln Gln Gly Pro Gly Ala Ala Ala Ala Ala Ala Gly Arg Gly
           1090                1095                1100

Pro Gly Gly Tyr Gly Pro Gly Gln Gln Gly Pro Gly Gly Pro Gly Ala
1105                1110                1115                1120

Ala Ala Ala Ala Ala Gly Arg Gly Pro Gly Gly Tyr Gly Pro Gly
           1125                1130                1135

Gln Gln Gly Pro Gly Gln Gln Gly Pro Gly Gly Pro Gly Ala Ala Ala
           1140                1145                1150

Ala Ala Ala Gly Pro Gly Gly Tyr Gly Pro Gly Gln Gln Gly Thr Gly
           1155                1160                1165

Ala Ala Ala Ala Ala Ala Gly Ser Gly Ala Gly Gly Tyr Gly Pro
           1170                1175                1180

Gly Gln Gln Gly Pro Gly Gly Pro Gly Ala Ala Ala Ala Ala Gly
1185                1190                1195                1200

Pro Gly Gly Tyr Gly Pro Gly Gln Gln Gly Pro Gly Ala Ala Ala Ala
           1205                1210                1215

Ala Ala Ala Gly Ser Gly Pro Gly Gly Tyr Gly Pro Gly Gln Gln Gly
           1220                1225                1230

Pro Gly Gly Ser Ser Ala Ala Ala Ala Ala Gly Pro Gly Arg Tyr
           1235                1240                1245

Gly Pro Gly Gln Gln Gly Pro Gly Ala Ala Ala Ala Ala Ala Gly
        1250                1255                1260

Ser Gly Pro Gly Gly Tyr Gly Pro Gly Gln Gln Gly Pro Gly Gly Pro
1265                1270                1275                1280

Gly Ala Ala Ala Ala Ala Ala Ala Gly Arg Gly Pro Gly Gly Tyr
           1285                1290                1295

Gly Pro Gly Gln Gln Gly Pro Gly Gly Pro Gly Ala Ala Ala Ala Ala
```

```
                1300            1305            1310
Ala Gly Pro Gly Gly Tyr Gly Pro Gly Gln Gln Gly Pro Gly Ala Ala
        1315            1320            1325
Ala Ala Ala Ala Ala Gly Ser Gly Pro Gly Gly Tyr Gly Pro Gly Gln
        1330            1335            1340
Gln Gly Pro Gly Gly Pro Gly Ala Ala Ala Ala Ala Ala Gly Arg
1345            1350            1355            1360
Gly Pro Gly Gly Tyr Gly Gln Gln Gln Gly Pro Gly Gly Pro Gly
            1365            1370            1375
Ala Ala Ala Ala Ala Gly Pro Gly Gly Tyr Gly Pro Gly Gln Gln
        1380            1385            1390
Gly Pro Gly Ala Ala Ala Ala Ala Ala Gly Ser Gly Pro Gly Gly
        1395            1400            1405
Tyr Gly Pro Gly Gln Gln Gly Pro Gly Arg Ser Gly Ala Ala Ala
        1410            1415            1420
Ala Ala Ala Ala Gly Arg Gly Pro Gly Gly Tyr Gly Pro Gly Gln Gln
1425            1430            1435            1440
Gly Pro Gly Gly Pro Gly Ala Ala Ala Ala Ala Gly Pro Gly Gly
            1445            1450            1455
Tyr Gly Pro Gly Gln Gln Gly Pro Gly Ala Ala Ala Ala Ala Ser Ala
        1460            1465            1470
Gly Arg Gly Pro Gly Gly Tyr Gly Pro Gly Gln Gln Gly Pro Gly Gly
        1475            1480            1485
Ser Gly Ala Ala Ala Ala Ala Ala Gly Arg Gly Pro Gly Gly Tyr Gly
        1490            1495            1500
Pro Gly Gln Gln Gly Pro Gly Gly Pro Gly Ala Ala Ala Ala Ala Ala
1505            1510            1515            1520
Ala Gly Thr Gly Pro Gly Gly Tyr Gly Pro Gly Gln Gln Gly Pro Gly
            1525            1530            1535
Gly Ser Gly Ala Ala Ala Ala Ala Ala Gly Arg Gly Pro Gly Gly Tyr
        1540            1545            1550
Gly Pro Gly Gln Gln Gly Pro Gly Gly Pro Gly Ala Ala Ala Ala Ala
        1555            1560            1565
Ala Gly Pro Gly Gly Tyr Gly Pro Gly Gln Gln Gly Pro Gly Ala Ala
        1570            1575            1580
Ala Ala Ala Ala Ala Gly Ser Gly Pro Gly Gly Tyr Gly Pro Gly Gln
1585            1590            1595            1600
Gln Gly Pro Gly Gly Pro Gly Ala Ala Ala Ala Ala Ala Gly Arg Gly
            1605            1610            1615
Pro Gly Gly Tyr Gly Pro Gly Gln Gln Gly Pro Gly Gly Pro Gly Ala
            1620            1625            1630
Ala Ala Ala Ala Ala Ala Gly Arg Gly Pro Gly Gly Tyr Gly Pro Gly
        1635            1640            1645
Gln Gln Gly Pro Gly Gly Ser Gly Ala Ala Ala Ala Ala Ser Gly Arg
        1650            1655            1660
Gly Pro Gly Gly Tyr Gly Pro Gly Gln Gln Gly Pro Gly Gly Pro Gly
1665            1670            1675            1680
Ala Ala Ala Ala Ala Ala Gly Pro Gly Gly Tyr Gly Pro Gly Gln Gln
            1685            1690            1695
Gly Pro Gly Ala Ala Ala Ala Ala Ala Ala Gly Arg Gly Pro Gly
            1700            1705            1710
Gly Tyr Gly Pro Gly Gln Gln Gly Pro Gly Gly Pro Gly Ala Ala Ala
        1715            1720            1725
```

```
Ala Ala Ala Ala Gly Arg Gly Pro Gly Gly Tyr Gly Pro Gly Gln Gln
        1730                1735                1740

Gly Pro Gly Gly Ser Gly Ala Ala Ala Ala Ala Gly Arg Gly Pro
1745                1750                1755                1760

Gly Gly Tyr Gly Pro Gly Gln Gln Gly Pro Gly Pro Gly Ala Ala
            1765                1770                1775

Ala Ala Ala Ala Gly Pro Gly Gly Tyr Gly Pro Gly Gln Gln Gly Pro
        1780                1785                1790

Gly Ala Ala Ala Ala Ala Gly Arg Gly Pro Gly Gly Tyr Gly Pro
        1795                1800                1805

Gly Gln Gln Gly Pro Gly Gly Ser Gly Ala Ala Ala Ala Ala Gly
        1810                1815                1820

Arg Gly Pro Gly Gly Tyr Gly Pro Gly Gln Gln Gly Pro Gly Gly Pro
1825                1830                1835                1840

Gly Ala Ala Ala Ala Ala Ala Gly Pro Gly Gly Tyr Gly Pro Gly Gln
            1845                1850                1855

Gln Gly Thr Gly Ala Ala Ala Ala Ala Ala Gly Ser Gly Ala Gly
        1860                1865                1870

Gly Tyr Gly Pro Gly Gln Gln Gly Pro Gly Gly Pro Gly Ala Ala Ala
        1875                1880                1885

Ala Ala Ala Gly Pro Gly Gly Tyr Gly Pro Gly Gln Gln Gly Pro Gly
        1890                1895                1900

Ala Ala Ala Ala Ala Ala Gly Ser Gly Pro Gly Gly Tyr Gly Pro
1905                1910                1915                1920

Gly Gln Gln Gly Pro Gly Gly Pro Gly Ala Ala Ala Ala Ala Ala
            1925                1930                1935

Gly Arg Gly Pro Gly Gly Tyr Gly Pro Gly Gln Gln Gly Pro Gly Gly
            1940                1945                1950

Ser

<210> SEQ ID NO 43
<211> LENGTH: 563
<212> TYPE: PRT
<213> ORGANISM: Nephila madagascariensis

<400> SEQUENCE: 43

Gln Gly Pro Ser Gly Pro Gly Ser Ala Ala Ala Ala Ala Ala Gly
 1               5                  10                  15

Pro Gly Gln Gln Gly Pro Gly Gly Tyr Gly Pro Gly Gln Gln Gly Pro
            20                  25                  30

Gly Gly Tyr Gly Pro Gly Gln Gln Gly Pro Ser Gly Pro Gly Ser Ala
        35                  40                  45

Ala Ala Ala Ala Ala Ala Ala Gly Pro Gly Gln Gln Gly Pro
 50                  55                  60

Gly Gly Tyr Gly Pro Gly Pro Gln Gly Pro Gly Tyr Gly Pro Gly
65                  70                  75                  80

Gln Gln Gly Pro Ser Gly Tyr Gly Pro Gly Gln Gln Gly Pro Ser Gly
            85                  90                  95

Pro Gly Ser Ala Ala Ser Ala Ala Ala Ala Gly Ser Gly Gln Gln
            100                 105                 110

Gly Pro Gly Gly Tyr Gly Pro Gly Gln Gln Gly Pro Gly Gly Tyr Gly
        115                 120                 125

Pro Gly Gln Gln Gly Pro Ser Gly Pro Gly Ser Ala Ala Ala Ala Ala
        130                 135                 140
```

-continued

```
Ala Ala Gly Pro Gly Gln Gln Gly Pro Gly Tyr Gly Pro Gly Gln
145                 150                 155                 160

Gln Gly Pro Gly Gly Tyr Gly Pro Gly Gln Gln Gly Pro Ser Gly Pro
                165                 170                 175

Gly Ser Ala Ala Ala Ala Ala Ala Ala Gly Pro Gly Gln Gln Gly
            180                 185                 190

Pro Gly Gly Tyr Gly Pro Gly Gln Gln Gly Pro Gly Tyr Gly Pro
            195                 200                 205

Gly Gln Gln Gly Pro Ser Gly Pro Gly Ser Ala Ala Ala Ala Ala
    210                 215                 220

Ala Gly Pro Gly Gln Gln Gly Pro Gly Gly Tyr Gly Pro Gly Gln Gln
225                 230                 235                 240

Gly Pro Gly Gly Tyr Gly Pro Gly Gln Gln Gly Pro Ser Gly Pro Gly
                245                 250                 255

Ser Ala Ala Ala Ala Ala Ala Ala Gly Pro Gly Gln Gln Gly
            260                 265                 270

Pro Gly Gly Tyr Gly Pro Gly Gln Gln Gly Pro Gly Gln Gln Gly Pro
            275                 280                 285

Ser Gly Pro Gly Ser Ala Ala Ala Ala Ala Ala Gly Pro Gly Pro
    290                 295                 300

Gln Gly Pro Gly Gly Tyr Gly Pro Gly Gln Gln Gly Pro Gly Tyr
305                 310                 315                 320

Gly Pro Ser Gly Pro Gly Ser Ala Ala Ala Ala Ala Ala Ala Gly
                325                 330                 335

Pro Gly Gln Gln Gly Pro Gly Gly Tyr Gly Pro Gly Gln Gln Arg Pro
            340                 345                 350

Ser Gly Tyr Gly Pro Gly Gln Gln Gly Pro Ser Gly Pro Gly Ser Ala
                355                 360                 365

Ala Ala Ala Ala Ala Gly Pro Gly Gln Gln Gly Pro Gly Ala Tyr
    370                 375                 380

Gly Pro Ser Gly Pro Gly Ser Ala Ala Ala Ala Gly Leu Gly Gly
385                 390                 395                 400

Tyr Gly Pro Ala Gln Gln Gly Pro Ser Gly Ala Gly Ser Ala Ala Ala
                405                 410                 415

Ala Ala Ala Ala Gly Pro Gly Gly Tyr Gly Pro Val Gln Gln Gly Pro
            420                 425                 430

Ser Gly Pro Gly Ser Ala Ala Gly Pro Gly Tyr Gly Pro Ala Gln
    435                 440                 445

Gln Gly Pro Ala Arg Tyr Gly Pro Gly Ser Ala Ala Ala Ala Ala
    450                 455                 460

Ala Ala Gly Ser Ala Gly Tyr Gly Pro Gly Pro Gln Ala Ser Ala Ala
465                 470                 475                 480

Ala Ser Arg Leu Ala Ser Pro Asp Ser Gly Ala Arg Val Ala Ser Ala
                485                 490                 495

Val Ser Asn Leu Val Ser Ser Gly Pro Thr Ser Ser Ala Ala Leu Ser
            500                 505                 510

Ser Val Ile Ser Asn Ala Val Ser Gln Ile Gly Ala Ser Asn Pro Gly
        515                 520                 525

Leu Ser Gly Cys Asp Val Leu Ile Gln Ala Leu Leu Glu Ile Val Ser
        530                 535                 540

Ala Cys Val Thr Ile Leu Ser Ser Ser Ser Ile Gly Gln Val Asn Tyr
545                 550                 555                 560
```

Gly Ala Ala

<210> SEQ ID NO 44
<211> LENGTH: 230
<212> TYPE: PRT
<213> ORGANISM: Nephila senegalensis
<220> FEATURE:
<221> NAME/KEY: misc_feature
<222> LOCATION: (47)
<223> OTHER INFORMATION: Xaa = Val or Gly
<220> FEATURE:
<221> NAME/KEY: misc_feature
<222> LOCATION: (183)
<223> OTHER INFORMATION: Xaa = Asn or Ser
<220> FEATURE:
<221> NAME/KEY: misc_feature
<222> LOCATION: (204)
<223> OTHER INFORMATION: Xaa = Gln or Arg

<400> SEQUENCE: 44

Gln Gly Pro Gly Gly Tyr Gly Pro Ser Gly Pro Gly Ser Ala Ala Ala
 1               5                  10                  15

Ala Ser Ala Ala Ala Gly Pro Gly Gln Gln Gly Pro Gly Ala Tyr Gly
             20                  25                  30

Pro Ser Gly Pro Gly Ser Ala Ala Ala Ala Gly Pro Gly Xaa Tyr
         35                  40                  45

Gly Pro Gly Gln Gln Gly Pro Ser Gly Pro Gly Ala Ala Ala Ala
 50                  55                  60

Ala Gly Pro Gly Gln Gln Gly Pro Gly Tyr Gly Pro Gly Ala Ala
65                   70                  75                  80

Ala Ala Ala Ala Ala Ala Gly Pro Gly Gln Gln Gly Pro Val Ala
                 85                  90                  95

Tyr Gly Pro Ser Gly Pro Gly Ser Ala Ala Ser Ala Ala Gly Pro Gly
                100                 105                 110

Gly Tyr Gly Pro Ala Arg Tyr Gly Pro Ser Gly Ser Ala Ala Ala Ala
            115                 120                 125

Ala Ala Ala Gly Ala Gly Ser Ala Gly Tyr Gly Pro Gly Pro Gln Ala
        130                 135                 140

Ser Ala Ala Ser Arg Leu Ala Ser Pro Asp Ser Gly Ala Arg Val
145                 150                 155                 160

Ala Ser Ala Val Ser Asn Leu Val Ser Ser Gly Pro Thr Ser Ser Ala
                165                 170                 175

Ala Leu Ser Ser Val Ile Xaa Asn Ala Val Ser Gln Ile Gly Ala Ser
            180                 185                 190

Asn Pro Gly Leu Ser Gly Cys Asp Val Leu Ile Xaa Ala Leu Leu Glu
        195                 200                 205

Ile Val Ser Ala Cys Val Thr Ile Leu Ser Ser Ser Ser Ile Gly Gln
    210                 215                 220

Val Asn Tyr Gly Ala Ala
225                 230

<210> SEQ ID NO 45
<211> LENGTH: 651
<212> TYPE: PRT
<213> ORGANISM: Argiope trifasciata

<400> SEQUENCE: 45

Ala Gly Gly Pro Gly Ala Gly Gly Ala Gly Ala Gly Val Gly Pro
 1               5                  10                  15

Gly Gly Phe Gly Gly Pro Gly Gly Phe Gly Gly Ala Gly Gly Pro Gly

-continued

```
                20                  25                  30
Gly Pro Gly Gly Pro Gly Gly Ala Gly Gly Ala Gly Gly Ala Gly
             35                  40                  45
Gly Leu Tyr Gly Pro Gly Gly Ala Gly Gly Leu Tyr Gly Pro Gly Gly
         50                  55                  60
Leu Tyr Gly Pro Gly Gly Ala Gly Val Pro Gly Ala Pro Gly Ala Ser
 65                  70                  75                  80
Gly Arg Ala Gly Gly Ile Gly Gly Ala Ala Gly Ala Gly Ala Gly
                 85                  90                  95
Gly Val Gly Pro Gly Gly Val Ser Gly Gly Ala Gly Gly Ala Gly Gly
                100                 105                 110
Ser Gly Val Thr Val Val Glu Ser Val Ser Val Gly Gly Ala Gly Gly
                115                 120                 125
Pro Gly Ala Gly Gly Val Gly Pro Gly Gly Val Gly Pro Gly Gly Val
            130                 135                 140
Gly Pro Gly Gly Ile Tyr Gly Pro Gly Gly Ala Gly Gly Leu Tyr Gly
145                 150                 155                 160
Pro Gly Ala Gly Gly Ala Phe Gly Pro Gly Gly Ala Gly Ala Pro
                165                 170                 175
Gly Gly Pro Gly Gly Pro Gly Gly Pro Gly Gly Pro Gly Gly Leu Gly
                180                 185                 190
Gly Gly Val Gly Gly Ala Gly Thr Gly Gly Val Gly Pro Gly Ala
            195                 200                 205
Gly Gly Val Gly Pro Ser Gly Ala Gly Gly Thr Gly Pro Val Ser
            210                 215                 220
Val Ser Ser Thr Val Ser Val Gly Gly Ala Gly Gly Pro Gly Ala Gly
225                 230                 235                 240
Gly Pro Gly Ala Gly Gly Ala Gly Ala Gly Val Gly Pro Gly Gly
            245                 250                 255
Phe Gly Gly Pro Gly Gly Phe Gly Gly Ala Gly Gly Pro Gly Gly Pro
                260                 265                 270
Gly Gly Pro Gly Gly Ala Gly Gly Ala Gly Ala Gly Gly Leu
            275                 280                 285
Tyr Gly Pro Gly Gly Ala Gly Gly Leu Tyr Gly Pro Gly Gly Leu Tyr
            290                 295                 300
Gly Pro Gly Gly Ala Gly Val Pro Gly Ala Pro Gly Ala Ser Gly Arg
305                 310                 315                 320
Ala Gly Gly Ile Gly Gly Ala Ala Gly Ala Gly Val Gly Pro Gly
                325                 330                 335
Gly Val Ser Gly Gly Ala Gly Ser Gly Val Ser Val Thr Glu Ser
            340                 345                 350
Val Thr Val Gly Gly Ala Gly Gly Ala Gly Ala Gly Ile Gly Gly
            355                 360                 365
Pro Ser Gly Leu Gly Gly Ala Gly Ala Thr Gly Gly Phe Gly Gly Arg
            370                 375                 380
Gly Gly Pro Gly Gly Pro Gly Gly Pro Gly Gly Pro Gly Arg Phe Gly
385                 390                 395                 400
Gly Ala Ala Gly Gly Ala Gly Ala Gly Gly Val Gly Pro Gly Gly Val
                405                 410                 415
Ser Gly Gly Ala Gly Gly Ala Gly Gly Ser Gly Val Thr Val Glu
            420                 425                 430
Ser Val Ser Val Gly Gly Ala Gly Gly Pro Gly Ala Gly Gly Val Gly
            435                 440                 445
```

```
Pro Gly Gly Val Gly Pro Gly Val Gly Pro Gly Gly Ile Tyr Gly
            450                 455                 460

Pro Gly Gly Ala Gly Gly Leu Tyr Gly Pro Gly Ala Gly Gly Ala Phe
465                 470                 475                 480

Gly Ser Gly Gly Gly Ala Gly Ala Pro Gly Gly Pro Gly Gly Pro Gly
                485                 490                 495

Gly Pro Gly Gly Pro Gly Gly Leu Gly Gly Val Gly Gly Ala Gly
            500                 505                 510

Thr Gly Gly Gly Val Gly Pro Gly Val Gly Val Gly Pro Ser Gly
            515                 520                 525

Gly Ala Gly Gly Thr Gly Pro Val Ser Val Ser Ser Thr Ile Thr Val
530                 535                 540

Gly Gly Gly Gln Ser Ser Gly Gly Val Leu Pro Ser Thr Ser Tyr Ala
545                 550                 555                 560

Pro Thr Thr Ser Gly Tyr Glu Arg Leu Pro Asn Leu Ile Asn Gly Ile
                565                 570                 575

Lys Ser Ser Met Gln Gly Gly Phe Asn Tyr Gln Asn Phe Gly Asn
                580                 585                 590

Ile Leu Ser Gln Tyr Ala Thr Gly Ser Gly Thr Cys Asn Tyr Tyr Asp
            595                 600                 605

Ile Asn Leu Leu Met Asp Ala Leu Leu Ala Ala Leu His Thr Leu Asn
            610                 615                 620

Tyr Gln Gly Ala Ser Tyr Val Pro Ser Tyr Pro Ser Pro Ser Glu Met
625                 630                 635                 640

Leu Ser Tyr Thr Glu Asn Val Arg Arg Tyr Phe
                645                 650

<210> SEQ ID NO 46
<211> LENGTH: 1002
<212> TYPE: PRT
<213> ORGANISM: Argiope trifasciata

<400> SEQUENCE: 46

Gly Ala Pro Gly Gly Pro Gly Gly Ala Gly Pro Gly Gly Ala Gly
1               5                   10                  15

Phe Gly Pro Gly Gly Ala Gly Phe Gly Pro Gly Gly Ala Gly
            20                  25                  30

Phe Gly Pro Gly Gly Ala Ala Gly Pro Gly Gly Pro Gly Pro
            35                  40                  45

Gly Gly Pro Gly Gly Ala Gly Gly Tyr Gly Pro Gly Gly Ala Gly Gly
            50                  55                  60

Tyr Gly Pro Gly Gly Val Gly Pro Gly Gly Ala Gly Tyr Gly Pro
65                  70                  75                  80

Gly Gly Ala Gly Gly Tyr Gly Pro Gly Gly Ser Gly Pro Gly Gly Ala
                85                  90                  95

Gly Pro Gly Gly Ala Gly Gly Glu Gly Pro Val Thr Val Asp Val Asp
            100                 105                 110

Val Thr Val Gly Pro Glu Gly Val Gly Gly Pro Gly Gly Ala Gly
            115                 120                 125

Pro Gly Gly Ala Gly Phe Gly Pro Gly Gly Ala Gly Phe Gly Pro
            130                 135                 140

Gly Gly Ala Pro Gly Ala Pro Gly Gly Pro Gly Gly Pro Gly Gly Pro
145                 150                 155                 160

Gly Gly Pro Gly Gly Pro Gly Gly Val Gly Pro Gly Gly Ala Gly Gly
```

-continued

```
                165                 170                 175
Tyr Gly Pro Gly Gly Ala Gly Val Gly Pro Ala Gly Thr Gly Gly
            180                 185                 190
Phe Gly Pro Gly Gly Ala Gly Phe Gly Pro Gly Gly Ala Gly Gly
            195                 200                 205
Phe Gly Pro Gly Gly Ala Gly Phe Gly Pro Gly Gly Ala Gly Gly
            210                 215                 220
Tyr Gly Pro Gly Gly Val Gly Pro Gly Gly Ala Gly Phe Gly Pro
225                 230                 235                 240
Gly Gly Val Gly Pro Gly Ser Gly Pro Gly Gly Ala Gly Gly Glu
            245                 250                 255
Gly Pro Val Thr Val Asp Val Asp Val Ser Val Gly Gly Ala Pro Gly
            260                 265                 270
Gly Gly Pro Gly Gly Ala Gly Pro Gly Gly Ala Gly Phe Gly Pro Gly
            275                 280                 285
Gly Gly Ala Gly Phe Gly Pro Gly Gly Ala Gly Phe Gly Pro Gly
            290                 295                 300
Gly Ala Ala Gly Pro Gly Gly Pro Gly Gly Pro Gly Gly Pro Gly
305                 310                 315                 320
Gly Ala Gly Gly Tyr Gly Pro Gly Gly Ala Gly Gly Tyr Gly Pro Gly
            325                 330                 335
Gly Val Gly Pro Gly Gly Ala Gly Tyr Gly Pro Gly Gly Ala Gly
            340                 345                 350
Gly Tyr Gly Pro Gly Gly Ser Gly Pro Gly Gly Ala Gly Pro Gly Gly
            355                 360                 365
Ala Gly Gly Glu Gly Pro Val Thr Val Asp Val Asp Val Thr Val Gly
            370                 375                 380
Pro Glu Gly Val Gly Gly Pro Gly Gly Ala Gly Pro Gly Gly Ala
385                 390                 395                 400
Gly Phe Gly Pro Gly Gly Ala Gly Phe Gly Pro Gly Gly Ala Pro
            405                 410                 415
Gly Ala Pro Gly Gly Pro Gly Gly Pro Gly Gly Pro Gly Gly Pro Gly
            420                 425                 430
Gly Pro Gly Gly Val Gly Pro Gly Gly Ala Gly Gly Tyr Gly Pro Gly
            435                 440                 445
Gly Ala Gly Gly Val Gly Pro Ala Gly Thr Gly Gly Phe Gly Pro Gly
            450                 455                 460
Gly Ala Gly Gly Phe Gly Pro Gly Gly Ala Gly Gly Phe Gly Pro Gly
465                 470                 475                 480
Gly Ala Gly Gly Phe Gly Pro Ala Gly Ala Gly Gly Tyr Gly Pro Gly
            485                 490                 495
Gly Val Gly Pro Gly Gly Ala Gly Gly Phe Gly Pro Gly Gly Val Gly
            500                 505                 510
Pro Gly Gly Ser Gly Pro Gly Gly Ala Gly Gly Glu Gly Pro Val Thr
            515                 520                 525
Val Asp Val Asp Val Ser Val Gly Gly Ala Pro Gly Gly Gly Pro Gly
            530                 535                 540
Gly Ala Gly Pro Gly Gly Ala Gly Phe Gly Pro Gly Gly Gly Ala Gly
545                 550                 555                 560
Phe Gly Pro Gly Gly Ala Gly Phe Gly Pro Gly Gly Ala Ala Gly
            565                 570                 575
Gly Pro Gly Gly Pro Gly Gly Pro Gly Gly Pro Gly Gly Ala Gly Gly
            580                 585                 590
```

```
Tyr Gly Pro Gly Gly Ala Gly Gly Tyr Gly Pro Gly Gly Val Gly Pro
            595                 600                 605
Gly Gly Ala Gly Gly Tyr Gly Pro Gly Gly Ala Gly Gly Tyr Gly Pro
        610                 615                 620
Gly Gly Ser Gly Pro Gly Gly Ala Gly Pro Gly Gly Ala Gly Gly Glu
625                 630                 635                 640
Gly Pro Val Thr Val Asp Val Asp Val Thr Val Gly Pro Glu Gly Val
                645                 650                 655
Gly Gly Gly Pro Gly Gly Ala Gly Pro Gly Gly Ala Gly Phe Gly Pro
            660                 665                 670
Gly Gly Gly Ala Gly Phe Gly Pro Gly Gly Ala Pro Gly Ala Pro Gly
            675                 680                 685
Gly Pro Gly Gly Pro Gly Gly Pro Gly Gly Pro Gly Pro Gly Gly Gly
        690                 695                 700
Val Gly Pro Gly Gly Ala Gly Gly Tyr Gly Pro Gly Gly Ala Gly Gly
705                 710                 715                 720
Phe Gly Pro Gly Gly Thr Gly Gly Phe Gly Pro Gly Gly Ala Gly Gly
                725                 730                 735
Phe Gly Pro Gly Gly Ala Gly Gly Phe Gly Pro Gly Gly Ala Gly Gly
            740                 745                 750
Phe Gly Pro Gly Gly Ala Gly Gly Tyr Gly Pro Gly Gly Val Gly Pro
            755                 760                 765
Gly Gly Ala Gly Gly Phe Gly Pro Gly Gly Val Gly Pro Gly Gly Ser
        770                 775                 780
Gly Pro Gly Gly Ala Gly Gly Glu Gly Pro Val Thr Val Asp Val Asp
785                 790                 795                 800
Val Ser Val Gly Gly Ala Pro Gly Gly Pro Gly Gly Ala Gly Ala Pro
                805                 810                 815
Gly Gly Ala Gly Phe Gly Pro Gly Gly Ala Gly Phe Gly Pro Gly
            820                 825                 830
Gly Gly Ala Gly Phe Gly Pro Gly Gly Ala Ala Gly Pro Ser Gly
            835                 840                 845
Pro Gly Gly Pro Gly Gly Pro Gly Ala Gly Gly Tyr Gly Pro Gly
        850                 855                 860
Gly Ala Gly Gly Tyr Gly Pro Gly Gly Val Gly Pro Gly Gly Ala Gly
865                 870                 875                 880
Gly Tyr Gly Pro Gly Gly Ala Gly Gly Tyr Gly Pro Gly Gly Ser Gly
                885                 890                 895
Pro Gly Gly Ala Gly Pro Gly Gly Ala Gly Gly Glu Gly Pro Val Thr
            900                 905                 910
Val Asp Val Asp Val Thr Val Gly Pro Glu Gly Val Gly Gly Gly Pro
            915                 920                 925
Gly Gly Ala Gly Pro Gly Gly Ala Gly Phe Gly Pro Gly Gly Gly Ala
            930                 935                 940
Gly Phe Gly Pro Gly Gly Ala Pro Gly Ala Pro Gly Gly Pro Gly Gly
945                 950                 955                 960
Pro Gly Gly Pro Gly Gly Pro Gly Gly Pro Gly Gly Val Gly Pro Gly
                965                 970                 975
Gly Ala Gly Gly Tyr Gly Pro Gly Gly Ala Gly Gly Val Gly Pro Ala
            980                 985                 990
Gly Thr Gly Gly Phe Gly Pro Gly Gly Ala
            995                 1000
```

<210> SEQ ID NO 47
<211> LENGTH: 854
<212> TYPE: PRT
<213> ORGANISM: Dolomedes tenebrosus

<400> SEQUENCE: 47

```
Gly Ser Gly Gln Gly Arg Tyr Gly Gly Gln Gly Ser Ser Gly Gly Tyr
 1               5                  10                  15

Gly Gln Gly Ala Gly Ala Gly Ala Ala Thr Ala Ala Thr Ala Arg Ala
            20                  25                  30

Asp Gly Ser Gly Gln Gly Arg Tyr Asp Gly Gln Ser Ser Gln Gly Gly
        35                  40                  45

Tyr Gly Gln Gly Ala Gly Ala Gly Ala Thr Ala Thr Ala Ala Ala Gly
    50                  55                  60

Gly Ala Gly Ser Gly Gln Gly Gly Tyr Gly Gly Gln Gly Gly Leu Gly
65                  70                  75                  80

Gly Tyr Gly Gln Gly Ala Gly Ala Gly Ala Ala Ala Thr Ala Ala
                85                  90                  95

Gly Gly Ala Gly Ser Gly Gln Gly Asp Tyr Gly Asp Gln Gly Gly Leu
            100                 105                 110

Gly Gly Tyr Gly Gln Gly Ser Gly Ala Gly Ser Ala Thr Ala Pro Ala
        115                 120                 125

Ala Gly Gly Ser Gly Phe Gly Gln Gly Gly Phe Gly Asn Arg Gly Gly
    130                 135                 140

Lys Gly Ala Tyr Gly Gln Ser Ala Gly Ala Gly Val Gly Ala Ala Ala
145                 150                 155                 160

Thr Ala Ala Ala Gly Gly Ala Gly Ser Gly Gln Gly Gly Tyr Gly Asp
                165                 170                 175

Gln Gly Gly Leu Gly Gly Tyr Gly Gln Gly Ala Gly Ala Gly Ala Ala
            180                 185                 190

Ser Ala Ala Ala Gly Gly Gly Asp Gly Tyr Glu Gln Gly Gly Tyr Gly
        195                 200                 205

Asn Gln Gly Gly Leu Gly Ser Phe Gly Gln Ala Gly Ala Gly Ala
    210                 215                 220

Ala Ala Ala Ala Ser Ala Gly Gly Ala Gly Ser Gly Arg Gly Gly Tyr
225                 230                 235                 240

Gly Asp Gln Gly Gly Leu Gly Gly Tyr Gly Gln Gly Ala Gly Ala Gly
                245                 250                 255

Ala Ala Ser Ala Ala Ala Gly Gly Asp Gly Tyr Gly Gln Gly Tyr
            260                 265                 270

Tyr Gly Asp Gln Gly Gly Arg Gly Gly Tyr Gly Gln Gly Ser Gly Ala
        275                 280                 285

Gly Ser Ala Thr Ala Ala Ala Gly Gly Ala Gly Phe Gly Gln Gly
    290                 295                 300

Gly Tyr Gly Gln Gly Gly Tyr Gly Asn Gln Gly Gly Leu Gly Ser Phe
305                 310                 315                 320

Gly Gln Gly Ala Gly Ala Gly Ala Ala Ala Ala Ser Ala Gly Gly
                325                 330                 335

Ala Gly Ser Gly Arg Gly Gly Tyr Gly Asp Gln Gly Gly Leu Gly Gly
            340                 345                 350

Tyr Gly Gln Gly Ala Gly Ala Gly Ala Ala Ala Ala Ala Gly Gly
        355                 360                 365

Gly Asp Gly Tyr Gly Gln Gly Gly Tyr Gly Asn Gln Gly Gly Leu Gly
    370                 375                 380
```

```
Ser Phe Gly Gln Gly Ala Gly Ala Gly Ala Ala Ala Ala Ser Ala
385                 390                 395                 400

Gly Gly Ala Gly Ser Gly Arg Gly Gly Tyr Gly Gln Gly Gly Tyr Gly
            405                 410                 415

Asn Gln Gly Gly Leu Gly Ser Phe Gly Gln Gly Ala Gly Ala Gly Ala
            420                 425                 430

Ala Ala Ala Ala Ser Ala Gly Gly Ala Gly Ser Gly Arg Gly Gly Tyr
            435                 440                 445

Gly Asp Gln Gly Gly Leu Gly Gly Tyr Gly Gln Gly Ala Gly Ser Gly
            450                 455                 460

Ala Ala Ala Ala Ala Gly Gly Asp Gly Tyr Gly Gln Gly Gly
465                 470                 475                 480

Tyr Gly Asn Gln Gly Gly Leu Gly Ser Phe Gly Gln Gly Ala Gly Ala
            485                 490                 495

Gly Ala Ala Ala Ala Ser Ala Gly Gly Ala Gly Ser Gly Arg Gly
            500                 505                 510

Gly Tyr Gly Gln Gly Gly Tyr Gly Asn Gln Gly Gly Leu Gly Ser Phe
            515                 520                 525

Gly Gln Gly Ala Gly Ala Gly Ala Ala Ala Ala Ser Ala Gly Gly
            530                 535                 540

Ala Gly Ser Gly Arg Gly Gly Tyr Gly Asp Gln Gly Gly Leu Gly Gly
545                 550                 555                 560

Tyr Gly Gln Gly Ala Gly Ala Gly Ala Ala Ser Ala Ala Ala Gly Gly
                565                 570                 575

Gly Asp Gly Tyr Gly Gln Gly Gly Tyr Gly Asn Gln Arg Gly Val Gly
            580                 585                 590

Ser Tyr Gly Gln Gly Ala Gly Ala Gly Ala Ala Ala Thr Ser Ala Ala
            595                 600                 605

Gly Gly Ala Gly Ser Gly Arg Gly Gly Tyr Gly Glu Gln Gly Gly Leu
            610                 615                 620

Gly Gly Tyr Gly Gln Gly Ala Gly Ala Gly Ala Ala Ser Thr Ala Ala
625                 630                 635                 640

Gly Gly Gly Asp Gly Tyr Gly Gln Gly Gly Tyr Gly Asn Gln Gly Gly
            645                 650                 655

Arg Gly Ser Tyr Gly Gln Gly Ser Gly Ala Gly Ala Gly Ala Ala Val
            660                 665                 670

Ala Ala Ala Ala Gly Gly Ala Val Ser Gly Gln Gly Gly Tyr Asp Gly
            675                 680                 685

Glu Gly Gly Gln Gly Gly Tyr Gly Gln Gly Ser Gly Ala Gly Ala Ala
            690                 695                 700

Val Ala Ala Ala Ser Gly Gly Thr Gly Ala Gly Gln Gly Gly Tyr Gly
705                 710                 715                 720

Ser Gln Gly Ser Gln Ala Gly Tyr Gly Gln Gly Ala Gly Phe Arg Ala
            725                 730                 735

Ala Ala Ala Thr Ala Ala Ala Gly Ala Gly Ala Gly Gly Gln
            740                 745                 750

Gly Gly Tyr Gly Gly Gln Gly Gly Tyr Gly Gln Gly Thr Gly Ala Gly
            755                 760                 765

Gly Ala Ser Ser Ala Gly Leu Ser Val Thr Val Gly Asn Met Val Ser
            770                 775                 780

Arg Leu Ser Ser Pro Glu Ala Ala Ser Arg Val Ser Ser Ala Val Ser
785                 790                 795                 800
```

Ser Leu Val Ser Asn Gly Gln Val Asn Val Asp Ala Leu Pro Ser Ile
            805                 810                 815

Ile Ser Asn Leu Ser Ser Ser Ile Ser Ala Ser Ala Thr Thr Ala Ser
            820                 825                 830

Asp Cys Glu Val Leu Val Gln Val Leu Leu Glu Val Val Ser Ala Leu
            835                 840                 845

Val Gln Ile Val Cys Ser
    850

<210> SEQ ID NO 48
<211> LENGTH: 691
<212> TYPE: PRT
<213> ORGANISM: Dolomedes tenebrosus

<400> SEQUENCE: 48

Tyr Gly Gln Gly Ser Gly Ala Gly Ala Ala Ala Ala Ala Ala Ala Ala
1               5                   10                  15

Gly Gly Ala Gly Gln Ser Gly Ser Gly Pro Tyr Gly Ala Ser Tyr Leu
            20                  25                  30

Ser Ser Thr Thr Tyr Thr Thr Ser Ser Gln Gly Ala Gly Gly Gly Val
            35                  40                  45

Gly Gly Tyr Gly Gln Gly Ser Gly Thr Gly Ser Ala Ala Ala Ala Ala
        50                  55                  60

Gly Ala Gly Ala Gly Gln Gly Gly Gln Gly Gly Tyr Gly Gln Gly
65              70                  75                  80

Ala Gly Gln Gly Gly Leu Gly Gly Tyr Gly Gln Gly Gly Ala Gly
            85                  90                  95

Ala Ala Ala Ala Ala Ala Ala Ala Gly Gly Ala Gly Ser Gly Gln
            100                 105                 110

Gly Gly Tyr Gly Gly Gln Gly Gly Leu Gly Gly Tyr Gly Gln Gly Ala
            115                 120                 125

Gly Ala Gly Ala Ala Ala Ala Ala Ala Ala Gly Gly Ala Gly Ala Gly
        130                 135                 140

Gln Gly Gly Phe Gly Gly Gln Gly Gly Tyr Gly Gln Gly Gly Gly Ala
145                 150                 155                 160

Gly Ala Ala Ala Ala Ala Ala Ala Ala Ala Ala Gly Gly Ala Gly
            165                 170                 175

Ser Gly Gln Gly Gly Tyr Gly Gly Gln Gly Gly Leu Gly Gly Tyr Gly
            180                 185                 190

Gln Gly Ala Gly Ala Gly Ala Ala Ala Ala Ala Ala Gly Gly Ala
            195                 200                 205

Gly Ala Gly Gln Gly Ser Tyr Gly Gly Gln Gly Gly Tyr Gly Gln Gly
        210                 215                 220

Gly Ala Gly Ala Ala Thr Ala Thr Ala Ala Ala Gly Gly Ala Gly
225                 230                 235                 240

Ser Gly Gln Gly Gly Tyr Gly Gly Gln Gly Gly Leu Gly Gly Tyr Gly
            245                 250                 255

Gln Gly Ala Gly Ala Gly Ala Ala Ala Ala Ala Ala Ala Ala Ala Gly
            260                 265                 270

Gly Ala Gly Ala Gly Gln Gly Gly Tyr Gly Gly Gln Gly Gly Gln Gly
        275                 280                 285

Gly Tyr Gly Gln Gly Ala Gly Ala Gly Ala Ala Ala Ala Ala Ala Gly
        290                 295                 300

Gly Ala Gly Ala Gly Gln Gly Gly Tyr Gly Gly Gln Gly Gly Tyr Gly
305                 310                 315                 320

```
Gln Gly Gly Gly Ala Gly Ala Ala Ala Ala Ala Ala Ser Gly
            325                 330                 335
Gly Ser Gly Ser Gly Gln Gly Gly Tyr Gly Gly Gln Gly Leu Gly
            340                 345                 350
Gly Tyr Gly Gln Gly Ala Gly Ala Gly Ala Gly Ala Ala Ser Ala
            355                 360                 365
Ala Ala Ala Gly Ala Gly Ser Gly Gln Gly Gly Tyr Gly Gly Gln Gly
370                 375                 380
Gly Leu Gly Gly Tyr Gly Gln Gly Ala Gly Ala Gly Ala Ala Ala Gly
385                 390                 395                 400
Ala Ser Gly Ser Gly Ser Gly Ala Gly Gln Gly Gly Leu Gly Gly
            405                 410                 415
Tyr Gly Gln Gly Ala Gly Ala Gly Ala Ala Ala Ala Ala Gly Ala
            420                 425                 430
Ser Gly Ala Gly Gln Gly Phe Gly Pro Tyr Gly Ser Ser Tyr Gln
            435                 440                 445
Ser Ser Thr Ser Tyr Ser Val Thr Ser Gln Gly Ala Ala Gly Gly Leu
450                 455                 460
Gly Gly Tyr Gly Gln Gly Ser Gly Ala Gly Ala Ala Ala Ala Gly Ala
465                 470                 475                 480
Ala Gly Gln Gly Gly Gln Gly Gly Tyr Gly Gln Gly Ala Gly Ala Gly
            485                 490                 495
Ala Gly Ala Gly Ala Gly Gln Gly Gly Leu Gly Gly Tyr Gly Gln Gly
            500                 505                 510
Ala Gly Ser Ser Ala Ala Ser Ala Ala Ala Gly Gly Ala Gly Ala
            515                 520                 525
Gly Gln Gly Gly Tyr Gly Gly Gln Gly Gly Leu Gly Gly Tyr Gly Gln
            530                 535                 540
Gly Ala Gly Ala Gly Ala Ser Ala Ala Ser Ala Ser Gly Ala Gly
545                 550                 555                 560
Ser Gly Gln Gly Gly Tyr Gly Gly Gln Gly Gly Tyr Gly Gln Gly Thr
            565                 570                 575
Gly Ala Gly Ala Ala Ser Ser Ala Gly Val Ala Val Thr Val Gly Asn
            580                 585                 590
Thr Val Ser Arg Leu Ser Ser Pro Gln Ala Ala Ser Arg Val Ser Ser
            595                 600                 605
Ala Val Ser Ser Leu Val Ser Asn Gly Gln Val Asn Val Ala Ala Leu
            610                 615                 620
Pro Ser Ile Ile Ser Ser Leu Ser Ser Ile Ser Ala Ser Ser Thr
625                 630                 635                 640
Ala Ala Ser Asp Cys Glu Val Leu Val Gln Val Leu Leu Glu Ile Val
                645                 650                 655
Ser Ala Leu Val Gln Ile Val Ser Ala Asn Val Gly Tyr Ile Asn
            660                 665                 670
Pro Glu Ala Ser Gly Ser Leu Asn Ala Val Gly Ser Ala Leu Ala Ala
            675                 680                 685
Ala Met Gly
690

<210> SEQ ID NO 49
<211> LENGTH: 734
<212> TYPE: PRT
<213> ORGANISM: Euagrus chisoseus
```

-continued

```
<400> SEQUENCE: 49

Asn Ala Ser Gln Ile Ala Ala Ser Val Ala Ser Val Ala Ser Ser
 1               5                  10                  15

Ala Ser Ala Ala Ala Ala Ala Ala Ser Ser Ser Ala Ala Ala Ala
             20                  25                  30

Gly Ala Ser Ser Ala Ala Gly Ala Ala Ser Ser Ser Thr Thr Thr
             35                  40                  45

Thr Thr Ser Thr Ser Ser Ser Ala Ala Ala Ala Ala Ala Ala Ala
         50                  55                  60

Ala Ala Ser Ala Ser Gly Ala Ser Ser Ala Ser Ala Ala Ser Ala
 65                  70                  75                  80

Ser Ala Ala Ala Ser Ala Phe Ser Ser Ala Leu Ile Ser Asp Leu Leu
                 85                  90                  95

Gly Ile Gly Val Phe Gly Asn Thr Phe Gly Ser Ile Gly Ser Ala Ser
                100                 105                 110

Ala Ala Ser Ser Ile Ala Ser Ala Ala Ala Gln Ala Ala Leu Ser Gly
                115                 120                 125

Leu Gly Leu Ser Tyr Leu Ala Ser Ala Gly Ala Ser Ala Val Ala Ser
130                 135                 140

Ala Val Ala Gly Val Gly Val Gly Ala Gly Ala Tyr Ala Tyr Ala Tyr
145                 150                 155                 160

Ala Ile Ala Asn Ala Phe Ala Ser Ile Leu Ala Asn Thr Gly Leu Leu
                165                 170                 175

Ser Val Ser Ser Ala Ala Ser Val Ala Ser Ser Val Ala Ser Ala Ile
                180                 185                 190

Ala Thr Ser Val Ser Ser Ser Ala Ala Ala Ala Ser Ala Ser
                195                 200                 205

Ala Ala Ala Ala Ala Ser Ala Ser Ala Ala Ser Ser Ala Ser Ala Ser
210                 215                 220

Ser Ser Ala Ser Ala Ala Ala Ala Gly Ala Ser Ala Ala Ala Gly
225                 230                 235                 240

Ala Ala Ser Ser Ala Ser Ala Ser Ala Ala Ser Ala Phe Ser Ser
                245                 250                 255

Ala Phe Ile Ser Ala Leu Leu Gly Phe Ser Gln Phe Asn Ser Val Phe
                260                 265                 270

Gly Ser Ile Thr Ser Ala Ser Leu Gly Leu Gly Ile Ala Ala Asn Ala
                275                 280                 285

Val Gln Ser Gly Leu Ala Ser Leu Gly Leu Gly Ala Ala Ala Ser Ala
                290                 295                 300

Ala Ala Ser Ala Val Ala Asn Ala Gly Leu Asn Gly Ser Gly Ala Tyr
305                 310                 315                 320

Ala Tyr Ala Thr Ala Ile Ala Ser Ala Ile Gly Asn Ala Leu Leu Gly
                325                 330                 335

Ala Gly Phe Leu Thr Ala Gly Asn Ala Ser Gln Ile Ala Ala Ser Val
                340                 345                 350

Ala Ser Ala Val Ala Ser Ser Ala Ser Ala Ala Ala Ala Ala Ser
                355                 360                 365

Ser Ser Ala Ala Ala Ala Gly Ala Ser Ser Ala Ala Gly Ala Ala Ser
                370                 375                 380

Ser Ser Ser Thr Thr Thr Thr Ser Thr Ser Ser Ala Ala Ala
385                 390                 395                 400

Ala Ala Ala Ala Ala Ala Ala Ala Ser Ala Ser Gly Ala Ser Ser Ala
                405                 410                 415
```

Ser Ala Ala Ala Ser Ala Ser Ala Ala Ala Ser Ala Phe Ser Ser Ala
                420                 425                 430

Leu Ile Gly Asp Leu Leu Gly Ile Gly Val Phe Gly Asn Thr Phe Gly
            435                 440                 445

Ser Ile Gly Ser Ala Ser Ala Ala Ser Ser Ile Ala Ser Ala Ala Ala
        450                 455                 460

Gln Ala Ala Leu Ser Gly Leu Gly Leu Ser Tyr Leu Ala Ser Ala Gly
465                 470                 475                 480

Ala Ser Ala Val Ala Ser Ala Val Ala Gly Val Gly Val Gly Ala Gly
                485                 490                 495

Ala Tyr Ala Tyr Ala Tyr Ala Ile Ala Asn Ala Phe Ala Ser Ile Leu
                500                 505                 510

Ala Asn Thr Gly Leu Leu Ser Val Ser Ser Ala Ala Ser Val Ala Ser
            515                 520                 525

Ser Val Ala Ser Ala Ile Ala Thr Ser Val Ser Ser Ser Ala Ala
            530                 535                 540

Ala Ala Ala Ser Ala Ser Ala Ala Ala Ala Ser Ala Gly Ala Ser
545                 550                 555                 560

Ala Ala Ser Ser Ala Ser Ala Ser Ser Ala Ser Ala Ala Ala Gly
                565                 570                 575

Ala Gly Ala Gly Ala Gly Ala Gly Ala Ser Gly Ala Ser Gly Ala Ala
            580                 585                 590

Gly Gly Ser Gly Gly Phe Gly Leu Ser Ser Gly Phe Gly Ala Gly Ile
            595                 600                 605

Gly Gly Leu Gly Gly Tyr Pro Ser Gly Ala Leu Gly Gly Leu Gly Ile
            610                 615                 620

Pro Ser Gly Leu Leu Ser Ser Gly Leu Leu Ser Pro Ala Ala Asn Gln
625                 630                 635                 640

Arg Ile Ala Ser Leu Ile Pro Leu Ile Leu Ser Ala Ile Ser Pro Asn
                645                 650                 655

Gly Val Asn Phe Gly Val Ile Gly Ser Asn Ile Ala Ser Leu Ala Ser
            660                 665                 670

Gln Ile Ser Gln Ser Gly Gly Ile Ala Ala Ser Gln Ala Phe Thr
            675                 680                 685

Gln Ala Leu Leu Glu Leu Val Ala Ala Phe Ile Gln Val Leu Ser Ser
            690                 695                 700

Ala Gln Ile Gly Ala Val Ser Ser Ser Ala Ser Ala Gly Ala Thr
705                 710                 715                 720

Ala Asn Ala Phe Ala Gln Ser Leu Ser Ser Ala Phe Ala Gly
                725                 730

<210> SEQ ID NO 50
<211> LENGTH: 912
<212> TYPE: PRT
<213> ORGANISM: Plectreurys tristis

<400> SEQUENCE: 50

Ala Ala Ala Ala Ala Ala Ala Ala Ala Gly Ala Gly Ala Gly Ala
 1               5                  10                  15

Gly Ala Gly Ala Gly Ala Gly Ala Gly Ala Ser Gly Ala Ser Thr
            20                  25                  30

Ser Val Ser Thr Ser Ser Ser Ser Gly Ser Gly Ala Gly Ala Gly Ala
            35                  40                  45

Gly Ser Gly Ala Gly Ser Gly Ala Gly Ala Gly Ser Gly Ala Gly Ala

-continued

```
            50                  55                  60
Gly Ala Gly Ala Gly Ala Gly Ala Gly Phe Gly Ser Gly Leu Gly
 65                  70                  75                  80
Leu Gly Tyr Gly Val Gly Leu Ser Ser Ala Gln Ala Gln Ala Gln Ala
                     85                  90                  95
Gln Ala Ala Gln Ala Gln Ala Gln Ala Gln Ala Tyr Ala
                100                 105                 110
Ala Ala Gln Ala Gln Ala Gln Ala Gln Ala Gln Ala Ala Ala
                115                 120                 125
Ala Ala Ala Ala Ala Ala Ala Gly Ala Gly Ala Gly Ala
                130                 135                 140
Gly Ala Gly Ala Gly Ala Gly Ala Gly Ser Gly Ala Ser Thr Ser Val
145                 150                 155                 160
Ser Thr Ser Ser Ser Ser Gly Ser Gly Ala Gly Ala Gly Ala Gly Ser
                165                 170                 175
Gly Ala Gly Ser Gly Ala Gly Ala Gly Ser Gly Ala Gly Ala Gly Ala
                180                 185                 190
Gly Ala Gly Gly Ala Gly Ala Gly Phe Gly Ser Gly Leu Gly Leu Gly
                195                 200                 205
Tyr Gly Val Gly Leu Ser Ser Ala Gln Ala Gln Ala Gln Ala Gln Ala
                210                 215                 220
Ala Ala Gln Ala Gln Ala Gln Ala Gln Ala Gln Ala Tyr Ala Ala Ala
225                 230                 235                 240
Gln Ala Gln Ala Gln Ala Gln Ala Gln Ala Ala Ala Ala Ala
                245                 250                 255
Ala Ala Ala Ala Ala Gly Ala Gly Ala Gly Ala Gly Ala
                260                 265                 270
Gly Ala Gly Ala Gly Ala Gly Ser Gly Ala Ser Thr Ser Val Ser Thr
                275                 280                 285
Ser Ser Ser Ser Gly Ser Gly Ala Gly Ala Gly Ala Gly Ser Gly Ala
                290                 295                 300
Gly Ser Gly Ala Gly Ala Gly Ser Gly Ala Gly Ala Gly Ala Gly Ala
305                 310                 315                 320
Gly Gly Ala Gly Ala Ala Phe Gly Ser Gly Leu Gly Leu Gly Tyr Gly
                325                 330                 335
Val Gly Leu Ser Ser Ala Gln Ala Gln Ala Gln Ala Gln Ala Ala Ala
                340                 345                 350
Gln Ala Gln Ala Asp Ala Gln Ala Gln Ala Tyr Ala Ala Ala Gln Ala
                355                 360                 365
Gln Ala Gln Ala Gln Ala Gln Ala Ala Ala Ala Ala Ala Ala
                370                 375                 380
Ala Ala Ala Ala Gly Ala Gly Ala Gly Ala Gly Ala Gly Ser Gly Ala
385                 390                 395                 400
Gly Ala Gly Ala Gly Ser Gly Ala Ser Thr Ser Val Ser Thr Ser Ser
                405                 410                 415
Ser Ser Gly Ser Gly Ala Gly Ala Gly Ala Gly Ser Gly Ala Gly Ser
                420                 425                 430
Gly Ala Gly Ala Gly Ser Gly Ala Gly Ala Gly Ala Gly Ala Gly Gly
                435                 440                 445
Ala Gly Ala Gly Phe Gly Ser Gly Leu Gly Leu Gly Tyr Gly Val Gly
                450                 455                 460
Leu Ser Ser Ala Gln Ala Gln Ala Gln Ala Gln Ala Ala Ala Gln Ala
465                 470                 475                 480
```

-continued

```
Gln Ala Asp Ala Gln Ala Gln Ala Tyr Ala Ala Gln Ala Gln Ala
                485                 490                 495
Gln Ala Gln Ala Gln Ala Gln Ala Ala Ala Ala Ala Ala Ala
            500                 505                 510
Ala Ala Gly Ala Gly Ala Gly Ala Gly Ala Ser Gly Ala Gly Ala
            515                 520                 525
Gly Ala Gly Ser Gly Ala Ser Thr Ser Val Ser Thr Ser Ser Ser Ser
        530                 535                 540
Gly Ser Gly Ala Gly Ala Gly Ala Gly Ser Gly Ala Gly Ser Gly Ala
545                 550                 555                 560
Gly Ala Gly Ser Gly Ala Gly Ala Gly Ala Gly Ala Gly Gly Ala Gly
                565                 570                 575
Ala Gly Phe Gly Ser Gly Leu Gly Leu Gly Tyr Gly Val Gly Leu Ser
            580                 585                 590
Ser Ala Gln Ala Gln Ala Gln Ser Ala Ala Ala Arg Ala Gln Ala
            595                 600                 605
Asp Ala Gln Ala Gln Ala Tyr Ala Ala Ala Gln Ala Gln Ala Gln Ala
        610                 615                 620
Gln Ala Gln Ala Gln Ala Ala Ala Ala Ala Ala Ala Ala Ala Ala
625                 630                 635                 640
Gly Ala Gly Ala Gly Ala Gly Ala Gly Ala Gly Ala Gly Ala Gly Ala
                645                 650                 655
Gly Ser Gly Ala Ser Thr Ser Val Ser Thr Ser Ser Ser Ser Ala Ser
            660                 665                 670
Gly Ala Gly Ala Gly Ala Gly Ser Gly Ala Gly Ser Gly Ala Gly Ala
            675                 680                 685
Gly Ser Gly Ala Gly Ala Gly Ala Gly Ala Gly Gly Ala Gly Ala Gly
        690                 695                 700
Phe Gly Ser Gly Leu Gly Leu Gly Tyr Gly Val Gly Leu Ser Ser Ala
705                 710                 715                 720
Gln Ala Gln Ala Gln Ala Gln Ala Ala Ala Gln Ala Gln Ala Gln Ala
                725                 730                 735
Gln Ala Gln Ala Leu Ala Ala Ala Gln Ala Gln Ala Gln Ala Gln Ala
            740                 745                 750
Gln Ala Gln Ala Ala Ala Ala Thr Ala Ala Ala Ala Ala Gly Ala
            755                 760                 765
Gly Ala Gly Ala Gly Ser Gly Ala Gly Ala Gly Ala Gly Ala Gly Ala
        770                 775                 780
Gly Ser Gly Ala Ser Thr Ser Val Ser Thr Ser Ser Ser Ala Ala
785                 790                 795                 800
Gly Ala Gly Ala Gly Ala Gly Ser Gly Ala Gly Ala Gly Ser Gly Thr
                805                 810                 815
Gly Ala Gly Ile Ala Leu Pro Ser Ile Val Leu Ser Pro Ala Ala Ser
            820                 825                 830
Ser Arg Ile Ser Ser Val Ser Ser Val Gln Ser Ala Gly Ser Gly
            835                 840                 845
Leu Ser Phe Ser Ser Leu Ser Asn Thr Leu Ser Gln Thr Ala Ser Ala
        850                 855                 860
Ile Arg Ser Ser Asn Pro Gln Leu Ser Ser Asp Val Leu Ile Gln
865                 870                 875                 880
Ser Leu Val Glu Ile Val Gly Leu Val Gln Ala Phe Thr Gly Ser
                885                 890                 895
```

```
Ser Ala Ser Ala Gln Thr Phe Val Asn Ser Leu Ser Gln Val Ala Gly
            900                 905                 910
```

<210> SEQ ID NO 51
<211> LENGTH: 764
<212> TYPE: PRT
<213> ORGANISM: Plectreurys tristis

<400> SEQUENCE: 51

```
Thr Asp Ser Val Ala Ser Ser Ala Ser Ser Ala Ser Ala Ser Ser
 1               5                  10                  15

Ser Ala Thr Gly Pro Asp Thr Gly Tyr Pro Val Gly Tyr Tyr Gly Ala
            20                  25                  30

Gly Gln Ala Glu Ala Ala Ser Ala Ala Ala Ala Ala Ser
        35                  40                  45

Ala Ala Glu Ala Ala Thr Ile Ala Gly Leu Gly Tyr Gly Arg Gln Gly
    50                  55                  60

Gln Gly Thr Asp Ser Ser Ala Ser Ser Val Ser Thr Ser Thr Ser Val
65                  70                  75                  80

Ser Ser Leu Ala Thr Gly Pro Gly Ser Arg Tyr Pro Val Arg Asp Tyr
                85                  90                  95

Gly Ala Asp Gln Ala Glu Ala Ala Ser Ala Ala Ala Ala Ala Ser
            100                 105                 110

Ala Ala Glu Glu Ile Ala Ser Leu Gly Tyr Gly Arg Gln Gly Gln Gly
        115                 120                 125

Thr Asp Ser Val Ala Ser Ser Ala Ser Ser Ala Ser Ala Ser Ser
    130                 135                 140

Ser Ala Thr Gly Pro Asp Thr Gly Tyr Pro Val Gly Tyr Tyr Gly Ala
145                 150                 155                 160

Gly Gln Ala Glu Ala Ala Ala Ser Ala Ala Ala Ala Ala Ala Ser
                165                 170                 175

Ala Ala Glu Ala Ala Thr Ile Ala Gly Leu Gly Tyr Gly Arg Gln Gly
            180                 185                 190

Gln Gly Thr Asp Ser Ser Ala Ser Ser Val Ser Thr Ser Thr Ser Val
        195                 200                 205

Ser Ser Ser Ala Thr Gly Pro Asp Thr Gly Tyr Pro Val Gly Tyr Tyr
    210                 215                 220

Gly Ala Gly Gln Ala Glu Ala Ala Ser Ala Ala Ala Ala Ala
225                 230                 235                 240

Ala Ser Ala Ala Glu Ala Ala Thr Ile Ala Gly Leu Gly Tyr Gly Arg
                245                 250                 255

Gln Gly Gln Gly Thr Asp Ser Ser Ala Ser Ser Val Ser Thr Ser Thr
            260                 265                 270

Ser Val Ser Ser Ser Ala Thr Gly Pro Asp Met Gly Tyr Pro Val Gly
        275                 280                 285

Asn Tyr Gly Ala Gly Gln Ala Glu Ala Ala Ser Ala Ala Ala Ala
    290                 295                 300

Ala Ala Ala Ser Ala Ala Glu Ala Ala Thr Ile Ala Ser Leu Gly Tyr
305                 310                 315                 320

Gly Arg Gln Gly Gln Gly Thr Asp Ser Ser Ala Ser Ser Val Ser Thr
                325                 330                 335

Ser Thr Ser Val Ser Ser Ser Ala Thr Gly Pro Gly Ser Arg Tyr Pro
            340                 345                 350

Val Arg Asp Tyr Gly Ala Asp Gln Ala Glu Ala Ala Ala Ser Ala Ala
        355                 360                 365
```

```
Ala Ala Ala Ala Ala Ala Ser Ala Ala Glu Glu Ile Ala Ser Leu
        370                 375                 380

Gly Tyr Gly Arg Gln Gly Gln Gly Thr Asp Ser Val Ala Ser Ser Ala
385                 390                 395                 400

Ser Ser Ser Ala Ser Ala Ser Ser Ser Ala Thr Gly Pro Asp Thr Gly
                405                 410                 415

Tyr Pro Val Gly Tyr Gly Ala Gly Gln Ala Glu Ala Ala Ala Ser
                420                 425                 430

Ala Ala Ala Ala Ala Ala Ser Ala Ala Glu Ala Ala Thr Ile Ala
            435                 440                 445

Gly Leu Gly Tyr Gly Arg Gln Gly Gln Gly Thr Asp Ser Ala Ser
        450                 455                 460

Ser Val Ser Thr Ser Thr Ser Val Ser Ser Ala Thr Gly Pro Gly
465                 470                 475                 480

Ser Arg Tyr Pro Val Arg Asp Tyr Gly Ala Asp Gln Ala Glu Ala Ala
                485                 490                 495

Ala Ser Ala Thr Ala Ala Ala Ala Ala Ser Ala Ala Glu Glu
            500                 505                 510

Ile Ala Ser Leu Gly Tyr Gly Arg Gln Gly Gln Gly Thr Asp Ser Val
515                 520                 525

Ala Ser Ser Ala Ser Ser Ser Ala Ser Ala Ser Ser Ala Thr Gly
        530                 535                 540

Pro Asp Thr Gly Tyr Pro Val Gly Tyr Gly Ala Gly Gln Ala Glu
545                 550                 555                 560

Ala Ala Ala Ser Ala Ala Ala Ala Ala Ser Ala Ala Glu Ala
                565                 570                 575

Ala Thr Ile Ala Gly Leu Gly Tyr Gly Arg Gln Gly Gln Gly Thr Asp
            580                 585                 590

Ser Ser Ala Ser Ser Val Ser Thr Ser Thr Ser Val Ser Ser Ser Ala
        595                 600                 605

Thr Gly Pro Gly Ser Arg Tyr Pro Val Met Asp Tyr Gly Ala Asp Gln
    610                 615                 620

Ala Glu Ala Ala Ala Ser Ala Ala Ala Ala Ala Ala Glu Ala Ala
625                 630                 635                 640

Thr Ile Ala Gly Leu Asp Tyr Glu Gly Gln Gly Gln Gly Thr Asp Ser
                645                 650                 655

Gly Ala Ser Ser Val Ser Ser Ser Thr Ser Val Ser Ser Ser Ala Thr
            660                 665                 670

Gly Val Thr Gln Thr Thr Ile Ala Leu Pro Pro Asp Val Ser Ala Arg
        675                 680                 685

Ile Ser Phe Leu Thr Ser Tyr Leu Gln Ser Ala Gly Ser Gly Leu Ser
        690                 695                 700

Leu Tyr Thr Leu Ser Asn Leu Leu Ser Gln Thr Ala Leu Ala Ile Ser
705                 710                 715                 720

Lys Ser Arg Pro Glu Leu Ser Pro Asn Glu Val Leu Ile Gln Ser Leu
                725                 730                 735

Ala Glu Ile Ile Val Ala Leu Val Gln Ala Leu Thr Lys Gln Ala Ser
            740                 745                 750

Ser Ser Ala Ser Val Gln Tyr Phe Gly Arg Phe Leu
        755                 760
```

<210> SEQ ID NO 52
<211> LENGTH: 2016

<212> TYPE: PRT
<213> ORGANISM: Plectreurys tristis

<400> SEQUENCE: 52

```
Ala Ile Ser Ser Ser Leu Tyr Ala Phe Asn Tyr Gln Ala Ser Ala Ala
  1               5                  10                  15

Ser Ser Ala Ala Ala Gln Ser Ala Gln Thr Ala Ser Thr Ser Ala
             20                  25                  30

Lys Gln Thr Ala Ala Ser Thr Ser Ala Ser Thr Ala Ala Thr Ser Thr
             35                  40                  45

Thr Gln Thr Ala Ala Thr Thr Ser Ala Ser Thr Ala Ala Ser Ser Gln
 50                  55                  60

Thr Val Gln Lys Ala Ser Thr Ser Ser Ala Ala Ser Thr Ala Ala Ser
 65                  70                  75                  80

Lys Ser Gln Ser Ser Ser Ala Gly Ser Ser Arg Thr Thr Ser Thr Ala
                 85                  90                  95

Ala Ala Ser Ala Ser Ser Tyr Ala Phe Ala Gln Ser Leu Ser Gln
            100                 105                 110

Tyr Leu Leu Ser Ser Gln Gln Phe Thr Thr Ala Phe Ala Ser Ser Thr
            115                 120                 125

Ala Val Ala Ser Ser Gln Gln Tyr Ala Glu Ala Met Ala Gln Ser Val
            130                 135                 140

Ala Thr Ser Leu Gly Leu Gly Tyr Thr Tyr Ala Ser Ala Leu Ser Val
145                 150                 155                 160

Ala Met Ala Gln Ala Ile Ser Gly Val Gly Gly Ala Ser Ala Tyr
                165                 170                 175

Ser Tyr Ala Thr Ala Ile Ser Gln Ala Ile Ser Arg Ala Leu Thr Ser
            180                 185                 190

Ser Gly Val Ser Leu Ser Ser Gln Ala Thr Ser Val Ala Ser Ala
            195                 200                 205

Ile Ser Ser Ser Leu Tyr Ala Phe Asn Tyr Gln Ser Ala Ala Ser
            210                 215                 220

Ser Ala Ala Ala Gln Ser Ser Ala Gln Thr Ala Ser Thr Ser Ala Lys
225                 230                 235                 240

Gln Thr Ala Ala Ser Thr Ser Ala Ser Thr Ala Ala Thr Ser Thr Thr
            245                 250                 255

Gln Thr Ala Ala Thr Thr Ser Ala Ser Thr Ala Ala Ser Ser Gln Thr
            260                 265                 270

Val Gln Lys Ala Ser Thr Ser Ser Ala Ala Ser Thr Ala Ala Ser Lys
            275                 280                 285

Ser Gln Ser Ser Ser Val Gly Ser Ser Thr Thr Ser Thr Ala Ala Ala
            290                 295                 300

Ser Ala Ser Ser Tyr Ala Phe Ala Gln Ser Leu Ser Gln Tyr Leu
305                 310                 315                 320

Leu Ser Ser Gln Gln Phe Thr Thr Ala Phe Ala Ser Ser Thr Ala Val
                325                 330                 335

Ala Ser Ser Gln Gln Tyr Ala Glu Ala Met Ala Gln Ser Val Ala Thr
                340                 345                 350

Ser Leu Gly Leu Gly Tyr Thr Tyr Thr Ser Ala Leu Ser Val Ala Met
            355                 360                 365

Ala Gln Ala Ile Ser Gly Val Gly Gly Ala Ser Ala Tyr Ser Tyr
            370                 375                 380

Ala Thr Ala Ile Ser Gln Ala Ile Ser Arg Val Leu Thr Ser Ser Gly
385                 390                 395                 400
```

```
Ile Ser Leu Ser Ser Ser Gln Ala Thr Ser Val Ala Ser Ala Ile Ser
                405                 410                 415

Ser Ser Leu Tyr Ala Phe Asn Tyr Gln Ala Ser Ala Ala Ser Ser Ala
            420                 425                 430

Ala Ala Gln Ser Ser Ala Gln Thr Ala Ser Thr Ser Ala Lys Gln Thr
            435                 440                 445

Ala Ala Ser Thr Ser Ala Ser Thr Ala Ala Thr Ser Thr Thr Gln Thr
            450                 455                 460

Ala Ala Thr Thr Ser Ala Ser Thr Ala Ala Ser Ser Gln Thr Val Gln
465                 470                 475                 480

Lys Ala Ser Thr Ser Ser Ala Ala Ser Thr Ala Ala Ser Lys Ser Gln
                485                 490                 495

Ser Ser Ser Val Gly Ser Ser Thr Ser Thr Ala Ala Ala Ser Ala
                500                 505                 510

Ser Ser Ser Tyr Ala Phe Ala Gln Ser Leu Ser Gln Tyr Leu Leu Ser
                515                 520                 525

Ser Gln Gln Phe Thr Thr Ala Phe Ala Ser Ser Thr Ala Val Ala Ser
            530                 535                 540

Ser Gln Gln Tyr Ala Glu Ala Met Ala Gln Ser Val Ala Thr Ser Leu
545                 550                 555                 560

Gly Leu Gly Tyr Thr Tyr Thr Ser Ala Leu Ser Val Ala Met Ala Gln
                565                 570                 575

Ala Ile Ser Gly Val Gly Gly Ala Ser Ala Tyr Ser Tyr Ala Thr
                580                 585                 590

Ala Ile Ser Gln Ala Ile Ser Arg Val Leu Thr Ser Ser Gly Val Ser
                595                 600                 605

Leu Ser Ser Ser Gln Ala Thr Ser Val Ala Ser Ala Ile Ser Ser Ser
                610                 615                 620

Leu Tyr Ala Phe Asn Tyr Arg Ala Ser Ala Ala Ser Ser Ala Ala Ala
625                 630                 635                 640

Gln Ser Ser Ala Gln Thr Ala Ser Thr Ser Ala Lys Gln Thr Ala Ala
                645                 650                 655

Ser Thr Ser Ala Ser Thr Ala Ala Thr Ser Thr Thr Gln Thr Ala Ala
                660                 665                 670

Thr Thr Ser Ala Ser Thr Ala Ala Ser Ser Gln Thr Val Gln Lys Ala
                675                 680                 685

Ser Thr Ser Ser Ala Ala Ser Thr Ala Ala Gln Gln Thr Gly Gln Ser
                690                 695                 700

Ser Ser Val Gln Asn Gln Gly Ser Ser Ala Ser Ser Ser Val
705                 710                 715                 720

Ser Val Ser Asp Ile Ser Asp Ser Leu Thr Thr Ser Leu Leu Gln Ser
                725                 730                 735

Glu Glu Phe Thr Ser Ala Phe Gly Ser Thr Val Ser Glu Ala Glu Ala
                740                 745                 750

Gln Ser Tyr Ala Glu Ala Val Ala Gln Ser Thr Val Ala Gln Leu Gly
                755                 760                 765

Ile Asp Tyr Ser Gln Ser Ser Ala Leu Ala Thr Ala Val Ala Asn Ala
                770                 775                 780

Val Ser Gln Val Lys Gln Gly Ser Ser Arg Ala Tyr Ala Arg Ala
785                 790                 795                 800

Ile Ala Tyr Ala Ile Thr Thr Tyr Leu Lys Thr Thr Arg Ile Ile Thr
                805                 810                 815
```

```
Thr Ile Thr Arg Thr Gln Val Lys Ser Phe Ala Ser Ala Ile Ser Ser
            820                 825                 830

Ser Leu Ser Thr Ala Arg Ala Thr Ser Ser Ala Asn Ala Tyr Gln Glu
        835                 840                 845

Gln Thr Thr Gln Ser Ser Ala Ala Ala Ser Ala Ala Ala Gln Ser Ser
    850                 855                 860

Glu Tyr Gln Thr Gln Asn Thr Gln Ser Ser Ala Ser Ala Ala Ser Ser
865                 870                 875                 880

Asp Ala Ser Thr Ser Tyr Gln Thr Gln Gln Ser Tyr Ser Asp Ala Ser
            885                 890                 895

Ala Ala Ser Val Ala Ala Glu Ser Thr Ser Ala Asn Gln Ala Gln Ser
            900                 905                 910

Thr Gln Ser Ser Ala Ala Ala Ser Ser Ser Thr Asn Ser Ala Tyr Gln
        915                 920                 925

Ser Gln Gln Ser Tyr Ile Asp Ala Ser Thr Val Ser Ser Ala Ser Ala
    930                 935                 940

Asn Thr Ala Gln Ser Thr Tyr Gln Val Thr Ile Pro Asp Asn Thr Tyr
945                 950                 955                 960

Phe Ala Glu Ser Leu Ser Ser Thr Leu Ile Gln His Glu Gln Phe Asn
            965                 970                 975

Ser Lys Phe Gly Ser Tyr Ile Pro Leu Val Thr Ala Arg Glu Tyr Ala
            980                 985                 990

Ser Ala Met Ala Arg Ala Thr Ala Leu Ile Ile Gly Phe Asp Ser Thr
        995                 1000                1005

Gly Thr Ser Ala Leu Glu Ser Ala Val Ala Val Ala Val Ser Asn Val
    1010                1015                1020

Asp Tyr Ala Ser Ala Tyr Ser Tyr Ala Arg Ala Ile Ala Phe Ala Ile
1025                1030                1035                1040

Ser Asn Val Leu Thr Asn Asn Gly Ile Phe Ala Ser Ala Ser Glu Ala
            1045                1050                1055

Leu Tyr Leu Ala Pro Ala Met Ile Ala Ser Leu His Ala Phe Gly Lys
            1060                1065                1070

Ser Ser Phe Ser Glu Ser Ser Ala Phe Ala Leu Ala Asn Ser Ile Ser
            1075                1080                1085

Pro Ser Thr Ala Ile Thr Ser Ala Gln Ser Ser Ser Val Ser Ala Gly
            1090                1095                1100

Ala Ser Ser Gly Gln Ser Ser Tyr Asp Thr Ser Ser Val Val Ser Ser
1105                1110                1115                1120

Ala Ser Ser Ala Glu Ala Thr Glu Ser Ser Ser Val Phe Asp Thr Tyr
            1125                1130                1135

Gln Ala Thr Gln Ile Glu Ser Ser Ala Ala Ala Ala Ala Ser Ser
        1140                1145                1150

Ser Ala Tyr Asp Ser Gln Phe Ser Glu Ser Ser Ala Ser Ser Ala
    1155                1160                1165

Ala Ala Ser Ala Phe Ser Glu Gln Thr Ser Tyr Asp Ile Ser Ser Asp
    1170                1175                1180

Leu Ser Ser Ala Ser Ala Thr Ala Ala Ala Ser Ser Ser Ala
1185                1190                1195                1200

Tyr Glu Ser Gln Phe Ser Asp Ala Ser Ser Gly Ser Ser Ala Ala Ala
            1205                1210                1215

Ala Ala Ser Ser Gln Gln Asn Ser Tyr Asp Thr Asp Ala Leu Tyr Ser
            1220                1225                1230

Ala Ser Ser Ala Ala Ser Ala Ala Ala Ser Ala Ser Ala Tyr Glu Leu
```

```
                    1235                1240                1245

Glu Phe Ser Asp Ala Ser Ser Ser Ser Ala Val Ala Val Ala Ser
1250                1255                1260

Ser Gln Gln Gly Ser Tyr Asp Thr Ser Ser Asp Phe Ser Ser Ala Ser
1265                1270                1275                1280

Ser Ala Ala Ala Ala Ala Ser Ala Tyr Glu Ser Lys Phe Leu Asp
                1285                1290                1295

Ala Ser Ser Ser Ser Ala Ala Ala Ala Ser Ser Gln Gln Ser
            1300                1305                1310

Ser Tyr Glu Thr Ser Ser Asp Leu Val Ser Ala Ser Ala Ala Ala
            1315                1320                1325

Ala Ala Ala Ser Ala Ser Ala Tyr Gln Ser Gln Phe Leu Asp Ala Ser
            1330                1335                1340

Ser Ser Ser Asn Ala Ala Ala Thr Thr Ser Ser Arg Gln Ser Ser Tyr
1345                1350                1355                1360

Asp Thr Ser Ser Asp Phe Ser Ser Ala Ser Ile Ala Ala Ala Ala
                1365                1370                1375

Ala Ser Ala Ser Ser Tyr Glu Ser Gln Phe Ser Asp Ala Ser Ser Ser
            1380                1385                1390

Ser Asn Ala Ala Ala Ala Ala Ser Ser Gln Gln Ser Ser Tyr Asp Thr
            1395                1400                1405

Ser Ser Asp Leu Val Ser Ala Ala Ser Ala Ser Ala Tyr Glu Ser Gln
            1410                1415                1420

Phe Leu Asp Ala Ser Ser Ser Asn Ala Ala Ala Thr Thr Ser Ser
1425                1430                1435                1440

Gln Gln Ser Ser Tyr Asp Thr Ser Ser Asp Phe Ser Ser Ala Ser Ile
                1445                1450                1455

Ala Ala Ala Ala Ala Ala Ser Ala Ser Ser Tyr Glu Ser Gln Phe Ser
                1460                1465                1470

Asp Ala Ser Ser Ser Asn Ala Ala Ala Ala Ala Ser Ser Gln Gln
            1475                1480                1485

Ser Ser Tyr Asp Thr Ser Ser Asp Leu Val Ser Ala Ser Ser Ala Ala
            1490                1495                1500

Ala Ala Ala Ala Ser Ala Ser Ser Tyr Glu Ser Gln Phe Ser Asp Ala
1505                1510                1515                1520

Ser Ser Ser Ser Asn Ala Ala Ala Ala Ser Ser Gln Gln Ser Ser
            1525                1530                1535

Tyr Asp Thr Ser Ser Asp Leu Val Ser Ala Ser Ser Ala Ala Ala Ala
            1540                1545                1550

Ala Ala Ser Ala Ser Ala Tyr Glu Ser Gln Phe Ser Asp Ala Ser Ser
            1555                1560                1565

Ser Arg Asn Ala Ala Ala Ala Ala Ser Ser Gln Gln Ser Ser Tyr Asp
            1570                1575                1580

Thr Ser Ser Asp Leu Val Ser Ala Ser Ser Ala Ala Ala Ala Ala
1585                1590                1595                1600

Ser Ala Ser Ser Tyr Glu Ser Gln Phe Leu Asp Ala Ser Ser Ser Ser
                1605                1610                1615

Asn Ala Ala Ala Thr Thr Ser Ser Gln Gln Ser Ser Tyr Asp Thr Ser
            1620                1625                1630

Ser Asp Phe Ser Ser Ala Ser Ile Ala Ala Ala Val Ala Ala Ser Ala
            1635                1640                1645

Ser Ser Tyr Glu Ser Gln Phe Ser Asp Ala Ser Ser Ser Ser Lys Ala
            1650                1655                1660
```

Ala Ala Ala Ala Ser Ser Gln Gln Ser Ser Tyr Asp Thr Ser Ser Asp
1665                1670                1675                1680

Leu Val Ser Ala Ser Ser Ala Ala Ala Ala Ala Ser Ala Ser Ser
            1685                1690                1695

Tyr Glu Ser Gln Phe Ser Asp Ala Ser Ser Ser Ser Asn Ala Ala Ala
            1700                1705                1710

Ala Ala Ser Ser Gln Gln Ser Ser Tyr Asp Thr Ser Ser Asp Phe Ser
            1715                1720                1725

Ser Ala Asn Ser Ala Ala Leu Ala Glu Ser Ser Ala Ala Thr Glu Ile
            1730                1735                1740

Tyr Gln Glu Thr Gln Ile Ala Ser Ser Ile Ala Ala Ala Ser Ala Leu
1745                1750                1755                1760

Ser Glu Ala His Thr Ser Glu Leu Ala Glu Ala Ser Ser Ser Ser Ser
            1765                1770                1775

Ala Ala Ser Ala Ala Ala Ala Ala Ser Glu Gln Ser Leu Tyr Asp
            1780                1785                1790

Thr Ser Ser Ala Ala Ser Ser Ala Ser Ser Ser Asp Phe Ile Ala Ser
            1795                1800                1805

Ser Asp Ile Arg Asn Gln Gln Ser Leu Ser Val Asn Ser Ala Ala Ser
            1810                1815                1820

Ser Ser Ala Ala Glu Glu Ser Val Ser Gln Val Asp Glu Glu Thr Tyr
1825                1830                1835                1840

Gln Asn Phe Asp Gln Tyr Ser Ser Ile Ser Ala Ser Ala Ser Ala Ala
            1845                1850                1855

Gln Ser Ser Glu Ile Tyr Gln Asp Val Ser Ser Ser Ala Ala Ala
            1860                1865                1870

Ser Thr Ser Ser Ala Ala Ser Ser Leu Glu Thr Ser Gly Thr Val Ala
            1875                1880                1885

Glu Ser Gly Ser Thr Ala Ala Ser Ser Ser Tyr Ala Ala Ala Ala Ala
            1890                1895                1900

Ala Ser Ser Ser Ala Gly Ser Thr Ser Ser Pro Ser Phe Leu Ser Ala
1905                1910                1915                1920

Asp Ser Leu Ser Ser Ser Leu Ala Ser Leu Arg Ile Cys Ser Phe Ser
            1925                1930                1935

Ser Lys Leu Met Ser Ser Leu Tyr Ser Gly Asp Gly Leu Asp Ile Ala
            1940                1945                1950

Glu Phe Ser Asp Ala Val Ser Ser Met Val Ser Ser Ile Lys Ser Ser
            1955                1960                1965

Asn Pro Gly Val Ser Ala Ser Gln Ile Leu Thr Glu Leu Leu Phe Glu
            1970                1975                1980

Val Ile Val Ala Phe Val Gln Ala Leu Thr Lys Ser Lys Phe Ser Thr
1985                1990                1995                2000

Met Glu Thr Ala Glu Ser Leu Ile Ala Ala Phe Ala Gln Ala Phe Val
            2005                2010                2015

<210> SEQ ID NO 53
<211> LENGTH: 1814
<212> TYPE: PRT
<213> ORGANISM: Plectreurys tristis

<400> SEQUENCE: 53

Ser Gln Gln Gly Pro Ile Gly Gly Val Gly Gly Ser Asn Ala Phe Ser
 1               5                  10                  15

Ser Ser Phe Ala Ser Ala Leu Ser Leu Asn Arg Gly Phe Thr Glu Val

```
                  20                  25                  30
Ile Ser Ser Ala Ser Ala Thr Ala Val Ala Ser Ala Phe Gln Lys Gly
            35                  40                  45
Leu Ala Pro Tyr Gly Thr Ala Phe Ala Leu Ser Ala Ala Ser Ala Ala
 50                  55                  60
Ala Asp Ala Tyr Asn Ser Ile Gly Ser Gly Ala Asn Ala Phe Ala Tyr
 65                  70                  75                  80
Ala Gln Ala Phe Ala Arg Val Leu Tyr Pro Leu Val Arg Gln Tyr Gly
                85                  90                  95
Leu Ser Ser Ser Gly Lys Ala Ser Ala Phe Ala Ser Ala Ile Ala Ser
                100                 105                 110
Ser Phe Ser Ser Gly Thr Ser Gly Gln Gly Pro Ser Ile Gly Gln Gln
                115                 120                 125
Gln Pro Pro Val Thr Ile Ser Ala Ala Ser Ala Ser Ala Gly Ala Ser
    130                 135                 140
Ala Ala Ala Val Gly Gly Gly Gln Val Gly Gln Gly Pro Tyr Gly Gly
145                 150                 155                 160
Gln Gln Gln Ser Thr Ala Ala Ser Ala Ser Ala Ala Ala Thr Ala
                165                 170                 175
Thr Ser Gly Ala Ala Gln Lys Gln Pro Ser Gly Glu Ser Ser Val Ala
                180                 185                 190
Thr Ala Ser Ala Ala Ala Thr Ser Val Thr Ser Gly Gly Ala Pro Val
            195                 200                 205
Gly Lys Pro Gly Val Pro Ala Pro Ile Phe Tyr Pro Gln Gly Pro Leu
    210                 215                 220
Gln Gln Gly Pro Ala Pro Gly Pro Ser Asn Val Gln Pro Gly Thr Ser
225                 230                 235                 240
Gln Gln Gly Pro Ile Gly Gly Val Gly Gly Ser Asn Ala Phe Ser Ser
                245                 250                 255
Ser Phe Ala Ser Ala Leu Ser Leu Asn Arg Gly Phe Thr Glu Val Ile
                260                 265                 270
Ser Ser Ala Ser Ala Thr Ala Val Ala Ser Ala Phe Gln Lys Gly Leu
            275                 280                 285
Ala Pro Tyr Gly Thr Ala Phe Ala Leu Ser Ala Ala Ser Ala Ala Ala
    290                 295                 300
Asp Ala Tyr Asn Ser Ile Gly Ser Gly Ala Asn Ala Phe Ala Tyr Ala
305                 310                 315                 320
Gln Ala Phe Ala Arg Val Leu Tyr Pro Leu Val Arg Gln Tyr Gly Leu
                325                 330                 335
Ser Ser Ser Gly Lys Ala Ser Ala Phe Ala Ser Ala Ile Ala Ser Ser
                340                 345                 350
Phe Ser Ser Gly Thr Ser Gly Gln Gly Pro Ser Ile Gly Gln Gln Gln
                355                 360                 365
Pro Pro Val Thr Ile Ser Ala Ala Ser Ala Ser Ala Gly Ala Ser Ala
    370                 375                 380
Ala Ala Val Gly Gly Gly Gln Val Gly Gln Gly Pro Tyr Gly Gly Gln
385                 390                 395                 400
Gln Gln Ser Thr Ala Ala Ser Ala Ser Ala Ala Ala Thr Ala Thr
                405                 410                 415
Ser Gly Ala Ala Gln Lys Gln Pro Ser Gly Glu Ser Ser Val Ala Thr
                420                 425                 430
Ala Ser Ala Ala Ala Thr Ser Val Thr Ser Gly Gly Ala Pro Val Gly
            435                 440                 445
```

-continued

```
Lys Pro Gly Val Pro Ala Pro Ile Phe Tyr Pro Gln Gly Pro Leu Gln
    450                 455                 460

Gln Gly Pro Ala Pro Gly Pro Ser Asn Val Gln Pro Gly Thr Ser Gln
465                 470                 475                 480

Gln Gly Pro Ile Gly Gly Val Gly Gly Ser Asn Ala Phe Ser Ser Ser
            485                 490                 495

Phe Ala Ser Ala Leu Ser Leu Asn Arg Gly Phe Thr Glu Val Ile Ser
        500                 505                 510

Ser Ala Ser Ala Thr Ala Val Ala Ser Ala Phe Gln Lys Gly Leu Ala
    515                 520                 525

Pro Tyr Gly Thr Ala Phe Ala Leu Ser Ala Ala Ser Ala Ala Ala Asp
530                 535                 540

Ala Tyr Asn Ser Ile Gly Ser Gly Ala Asn Ala Phe Ala Tyr Ala Gln
545                 550                 555                 560

Ala Phe Ala Arg Val Leu Tyr Pro Leu Val Gln Gln Tyr Gly Leu Ser
                565                 570                 575

Ser Ser Ala Lys Ala Ser Ala Phe Ala Ser Ala Ile Ala Ser Ser Phe
            580                 585                 590

Ser Ser Gly Thr Ser Gly Gln Gly Pro Ser Ile Gly Gln Gln Gln Pro
        595                 600                 605

Pro Val Thr Ile Ser Ala Ala Ser Ala Ser Ala Gly Ala Ser Ala Ala
    610                 615                 620

Ala Val Gly Gly Gly Gln Val Gly Gln Gly Pro Tyr Gly Gly Gln Gln
625                 630                 635                 640

Gln Ser Thr Ala Ala Ser Ala Ser Ala Ala Ala Thr Ala Thr Ser
                645                 650                 655

Gly Gly Ala Gln Lys Gln Pro Ser Gly Glu Ser Ser Val Ala Thr Ala
            660                 665                 670

Ser Ala Ala Ala Thr Ser Val Thr Ser Ala Gly Ala Pro Val Gly Lys
        675                 680                 685

Pro Gly Val Pro Ala Pro Ile Phe Tyr Pro Gln Gly Pro Leu Gln Gln
    690                 695                 700

Gly Pro Ala Pro Gly Pro Ser Asn Val Gln Pro Gly Thr Ser Gln Gln
705                 710                 715                 720

Gly Pro Ile Gly Gly Val Gly Gly Ser Asn Ala Phe Ser Ser Ser Phe
                725                 730                 735

Ala Ser Ala Leu Ser Leu Asn Arg Gly Phe Thr Glu Val Ile Ser Ser
            740                 745                 750

Ala Ser Ala Thr Ala Val Ala Ser Ala Phe Gln Lys Gly Leu Ala Pro
        755                 760                 765

Tyr Gly Thr Ala Phe Ala Leu Ser Ala Ala Ser Ala Ala Ala Asp Ala
    770                 775                 780

Tyr Asn Ser Ile Gly Ser Gly Ala Asn Ala Phe Ala Tyr Ala Gln Ala
785                 790                 795                 800

Phe Ala Arg Val Leu Tyr Pro Leu Val Gln Gln Tyr Gly Leu Ser Ser
                805                 810                 815

Ser Ala Lys Ala Ser Ala Phe Ala Ser Ala Ile Ala Ser Ser Phe Ser
            820                 825                 830

Ser Gly Thr Ser Gly Gln Gly Pro Ser Asn Gly Gln Gln Gln Pro Pro
        835                 840                 845

Val Thr Ile Ser Ala Ala Ser Ala Ser Ala Gly Ala Ser Ala Ala Ala
    850                 855                 860
```

```
Val Gly Gly Gly Gln Val Ser Gln Gly Pro Tyr Gly Gln Gln Gln
865                 870                 875                 880

Ser Thr Ala Ala Ser Ala Ser Ala Ala Ala Thr Ala Thr Ser Gly
            885                 890                 895

Gly Ala Gln Lys Gln Pro Ser Gly Glu Ser Ser Val Ala Thr Ala Ser
        900                 905                 910

Ala Ala Ala Thr Ser Val Thr Ser Ala Gly Ala Pro Gly Gly Lys Pro
        915                 920                 925

Gly Val Pro Ala Pro Ile Phe Tyr Pro Gln Gly Pro Leu Gln Gln Gly
        930                 935                 940

Pro Ala Pro Gly Pro Ser Asn Val Gln Pro Gly Thr Ser Gln Gln Gly
945                 950                 955                 960

Pro Ile Gly Gly Val Gly Gly Ser Asn Ala Phe Ser Ser Ser Phe Ala
                965                 970                 975

Ser Ala Leu Ser Leu Asn Arg Gly Phe Thr Glu Val Ile Ser Ser Ala
            980                 985                 990

Ser Ala Thr Ala Val Ala Ser Ala Phe Gln Lys Gly Leu Ala Pro Tyr
        995                 1000                1005

Gly Thr Ala Phe Ala Leu Ser Ala Ala Ser Ala Ala Ala Asp Ala Tyr
    1010                1015                1020

Asn Ser Ile Gly Ser Gly Ala Asn Ala Phe Ala Tyr Ala Gln Ala Phe
1025                1030                1035                1040

Ala Arg Val Leu Tyr Pro Leu Val Gln Gln Tyr Gly Leu Ser Ser Ser
                1045                1050                1055

Ala Lys Ala Ser Ala Phe Ala Ser Ala Ile Ala Ser Ser Phe Ser Ser
            1060                1065                1070

Gly Thr Ser Gly Gln Gly Pro Ser Ile Gly Gln Gln Gln Pro Pro Val
            1075                1080                1085

Thr Ile Ser Ala Ala Ser Ala Ser Ala Gly Ala Ser Ala Ala Ala Val
        1090                1095                1100

Gly Gly Gly Gln Val Gly Gln Gly Pro Tyr Gly Gly Gln Gln Gln Ser
1105                1110                1115                1120

Thr Ala Ala Ser Ala Ser Ala Ala Ala Thr Ala Thr Ser Gly Gly
                1125                1130                1135

Ala Gln Lys Gln Pro Ser Gly Glu Ser Ser Val Ala Thr Ala Ser Ala
        1140                1145                1150

Ala Ala Thr Ser Val Thr Ser Ala Gly Ala Pro Val Gly Lys Pro Gly
            1155                1160                1165

Val Pro Ala Pro Ile Phe Tyr Pro Gln Gly Pro Leu Gln Gln Gly Pro
        1170                1175                1180

Ala Pro Gly Pro Ser Tyr Val Gln Pro Ala Thr Ser Gln Gln Gly Pro
1185                1190                1195                1200

Ile Gly Gly Ala Gly Arg Ser Asn Ala Phe Ser Ser Ser Phe Ala Ser
                1205                1210                1215

Ala Leu Ser Gly Asn Arg Gly Phe Ser Glu Val Ile Ser Ser Ala Ser
            1220                1225                1230

Ala Thr Ala Val Ala Ser Ala Phe Gln Lys Gly Leu Ala Pro Tyr Gly
            1235                1240                1245

Thr Ala Phe Ala Leu Ser Ala Ala Ser Ala Ala Ala Asp Ala Tyr Asn
    1250                1255                1260

Ser Ile Gly Ser Gly Ala Asn Ala Phe Ala Tyr Ala Gln Ala Phe Ala
1265                1270                1275                1280

Arg Val Leu Tyr Pro Leu Val Gln Gln Tyr Gly Leu Ser Ser Ser Ala
```

-continued

```
                1285                1290                1295
Lys Ala Ser Ala Phe Ala Ser Ala Ile Ala Ser Ser Phe Ser Ser Gly
            1300                1305                1310
Ala Ala Gly Gln Gly Gln Ser Ile Pro Tyr Gly Gly Gln Gln Gln Pro
            1315                1320                1325
Pro Met Thr Ile Ser Ala Ala Ser Ala Ser Ala Gly Ala Ser Ala Ala
            1330                1335                1340
Ala Val Lys Gly Gly Gln Val Gly Gln Gly Pro Tyr Gly Gly Gln Gln
1345                1350                1355                1360
Gln Ser Thr Ala Ala Ser Ala Ser Ala Ala Thr Thr Ala Thr Ala
            1365                1370                1375
Gly Gly Ala Gln Lys His Pro Ser Gly Glu Tyr Ser Val Ala Thr Ala
            1380                1385                1390
Ser Ala Ala Ala Thr Ser Val Thr Ser Gly Gly Ala Pro Val Gly Lys
            1395                1400                1405
Pro Gly Val Pro Ala Pro Ile Phe Tyr Pro Gln Gly Pro Leu Gln Gln
            1410                1415                1420
Gly Pro Ala Pro Gly Pro Ser Asn Val Gln Pro Gly Thr Ser Gln Gln
1425                1430                1435                1440
Gly Pro Ile Gly Gly Val Gly Glu Ser Asn Thr Phe Ser Ser Phe
            1445                1450                1455
Ala Ser Ala Leu Gly Gly Asn Arg Gly Phe Ser Gly Val Ile Ser Ser
            1460                1465                1470
Ala Ser Ala Thr Ala Val Ala Ser Ala Phe Gln Lys Gly Leu Ala Pro
            1475                1480                1485
Tyr Gly Thr Ala Phe Ala Leu Ser Ala Ala Ser Ala Ala Ala Asp Ala
            1490                1495                1500
Tyr Asn Ser Ile Gly Ser Gly Ala Ser Ala Ser Ala Tyr Ala Gln Ala
1505                1510                1515                1520
Phe Ala Arg Val Leu Tyr Pro Leu Leu Gln Gln Tyr Gly Leu Ser Ser
            1525                1530                1535
Ser Ala Asp Ala Ser Ala Phe Ser Ala Ile Ala Ser Ser Phe Ser
            1540                1545                1550
Thr Gly Val Ala Gly Gln Gly Pro Ser Val Pro Tyr Val Gly Gln Gln
            1555                1560                1565
Gln Pro Ser Ile Met Val Ser Ala Ala Ser Ala Ser Ala Ala Ala Ser
1570                1575                1580
Ala Ala Ala Val Gly Gly Gly Pro Val Val Gln Gly Pro Tyr Asp Gly
1585                1590                1595                1600
Gly Gln Pro Gln Gln Pro Asn Ile Ala Ala Ser Ala Ala Ala Ala
            1605                1610                1615
Thr Ala Thr Ser Ser Gly Pro Lys Glu Glu Pro Leu Gly Glu Ser Ser
            1620                1625                1630
Val Ile Ala Thr Ser Val Ser Ala Ala Ser Ser Val Ser Ser Gly Gly
            1635                1640                1645
Ala Pro Gly Val Gln Gly Gly Pro Val Thr Val Ser Tyr Arg Glu
            1650                1655                1660
Gly Pro Ser Gln Ile Pro Ser Gln Gln Thr Leu Leu Gln Ala Val Pro
1665                1670                1675                1680
Ser Thr Gln Ser Val Gly Ser Gly Val Pro Val Gly Pro Asn Gln Tyr
            1685                1690                1695
Glu Met Val Tyr Ala Pro Leu Gln Gln Phe Gly Gly Val Ser Ala Ser
            1700                1705                1710
```

Asn Leu Leu Ser Pro Ser Ala His Ser Arg Ile Ala Ser Leu Met Ser
          1715                1720                1725

Asp Val Leu Ser Leu Phe Ser Pro Gly Asn Ser Gly Phe Asn Tyr Gly
          1730                1735                1740

Gly Phe Ala Arg Ala Leu Ser Ser Val Ala Arg Ala Val Ser Gln Ser
1745                1750                1755                1760

Asn Ala Lys Leu Ser Thr Thr Asp Val Ile Ile Gln Val Leu Met Glu
          1765                1770                1775

Ala Leu Val Ala Leu Ile Glu Leu Leu Ser Gly Ala Lys Ile Gly Val
          1780                1785                1790

Val His Pro Val Arg Ala Gln Ala Gly Ala Ser Ala Phe Ala Gln His
          1795                1800                1805

Phe Gly Ser Ala Phe Gly
          1810

<210> SEQ ID NO 54
<211> LENGTH: 525
<212> TYPE: PRT
<213> ORGANISM: Phidippus audax
<220> FEATURE:
<221> NAME/KEY: misc_feature
<222> LOCATION: (355)
<223> OTHER INFORMATION: Xaa = Pro or Ala
<220> FEATURE:
<221> NAME/KEY: misc_feature
<222> LOCATION: (359)
<223> OTHER INFORMATION: Xaa = Thr or Ala

<400> SEQUENCE: 54

Ala Gly Ala Gly Ala Gly Tyr Gly Ala Gly Ala Gly Ser Gly Ala Gly
 1               5                  10                  15

Ala Gly Ser Gly Ala Gly Ala Gly Ala Gly Ala Gly Ala Gly Ala Gly
              20                  25                  30

Ala Gly Tyr Gly Ala Gly Ala Gly Ser Gly Ala Gly Ala Gly Ala Gly
              35                  40                  45

Tyr Gly Arg Gly Ala Gly Ala Gly Ala Gly Ala Gly Ala Gly Tyr Gly
              50                  55                  60

Gln Gly Ala Gly Ala Gly Ala Gly Ala Gly Ala Gly Tyr Gly Ala Gly
65                  70                  75                  80

Ala Gly Ser Gly Ala Gly Ala Gly Tyr Gly Thr Gly Ala Gly Ser Gly
              85                  90                  95

Ala Gly Ser Gly Ala Gly Ser Gly Ala Gly Ser Gly Ala Gly Ala Gly
             100                 105                 110

Ala Gly Ala Gly Ala Gly Tyr Gly Ala Gly Ala Gly Ser Gly Ala Gly
             115                 120                 125

Ala Gly Ala Gly Tyr Gly Arg Gly Ala Gly Ala Gly Ala Gly Ala Gly
             130                 135                 140

Ala Gly Tyr Gly Gln Gly Ala Gly Ala Gly Ala Gly Ala Gly Ala Gly
145                 150                 155                 160

Ala Gly Ser Gly Ala Gly Ala Gly Ser Gly Ala Gly Ala Gly Ala Gly
             165                 170                 175

Ala Gly Tyr Gly Gln Gly Ala Gly Ala Gly Ala Gly Ala Gly Ala Gly
             180                 185                 190

Tyr Gly Ala Gly Ala Gly Ser Gly Ala Gly Ala Gly Ala Gly Tyr Gly
             195                 200                 205

Ala Gly Ala Gly Ser Gly Ala Gly Ala Gly Ser Gly Ala Gly Ala Gly
             210                 215                 220

```
Ala Gly Ala Gly Tyr Gly Gln Gly Ala Gly Ala Gly Ala Gly
225                 230                 235                 240

Tyr Gly Ala Gly Ala Gly Ser Gly Ala Gly Ala Gly Ser Gly Ala Gly
                245                 250                 255

Ala Gly Ser Gly Ala Gly Ala Gly Ser Gly Tyr Gly Ala Gly Ala Gly
            260                 265                 270

Ser Gly Ala Gly Ala Gly Ala Gly Tyr Gly Gln Gly Ala Gly Ala Gly
        275                 280                 285

Ala Gly Ala Gly Ala Gly Tyr Gly Ala Gly Ala Gly Ser Gly Ala Gly
    290                 295                 300

Thr Gly Ala Gly Tyr Gly Ala Gly Ala Gly Ala Gly Tyr Gly Ala Gly
305                 310                 315                 320

Ala Gly Ala Gly Ala Gly Ser Gly Ala Gly Ala Gly Ala Gly Tyr Gly
                325                 330                 335

Ala Gly Ala Gly Ala Gly Ala Gly Tyr Gly Ala Gly Ala Gly Ala Gly
            340                 345                 350

Ser Gly Xaa Gly Ala Gly Xaa Gly Tyr Gly Ala Gly Ala Gly Ala Gly
        355                 360                 365

Ser Gly Val Gly Ala Gly Ala Gly Ala Gly Ala Gly Ala Gly Tyr Gly
    370                 375                 380

Ala Gly Ala Gly Ala Gly Ala Gly Tyr Gly Ala Gly Ala Gly Ala Gly
385                 390                 395                 400

Ala Gly Ala Gly Ala Gly Ala Gly Tyr Gly Ala Gly Ala Gly Ala Gly
                405                 410                 415

Ala Ser Val Ser Ser Thr Val Ser Asn Thr Ala Ser Arg Met Ser Ser
            420                 425                 430

Glu Asn Thr Ser Arg Arg Val Ser Ser Ala Ile Ser Ser Ile Val Gly
        435                 440                 445

Ser Gly Gly Val Asn Met Asn Ser Leu Ser Asn Val Ile Ser Asn Val
    450                 455                 460

Ser Ser Ser Val Ala Ala Ser Asn Pro Gly Leu Ser Gly Cys Glu Val
465                 470                 475                 480

Leu Val Gln Thr Leu Leu Glu Val Val Ser Ala Leu Val His Ile Leu
                485                 490                 495

Ser Tyr Ala Ser Val Gly Ser Val Asp Ala Ser Ala Ala Gly Gln Ser
            500                 505                 510

Ala Gln Thr Val Ala Thr Ala Met Ser Ser Val Met Gly
        515                 520                 525

<210> SEQ ID NO 55
<211> LENGTH: 252
<212> TYPE: PRT
<213> ORGANISM: Zorocrates sp.

<400> SEQUENCE: 55

Gly Ala Ala Ala Ala Ser Ala Ala Ala Gly Gly Arg Gly Ser
1               5                   10                  15

Gln Gly Gly Tyr Gly Asp Asp Gly Ala Ala Ala Ala Ala Ala
            20                  25                  30

Ala Ala Ala Ala Ala Ala Gly Ser Gly Gly Thr Gly Gly Gln
        35                  40                  45

Gly Gly Arg Gly Asp Gly Gly Ala Ala Ala Ala Ala Ala Ala
    50                  55                  60

Glu Ala Ala Ala Gly Gly Lys Gly Arg Gln Gly Ser Tyr Gly Asp Asp
```

-continued

```
                65                  70                  75                  80
Gly Gly Ala Ala Val Ala Ala Ala Ala Ala Ala Ala Gly
                85                  90                  95
Arg Gly Gly Ser Gly Arg Gly Gln Gly Leu Arg Arg Asp Lys Gly Ser
                100                 105                 110
Tyr Gly Val Asp Gly Gly Ala Glu Ala Ala Ser Ala Ala Ala Thr
                115                 120                 125
Ala Gly Arg Gln Gly Arg Gln Gly Ser Tyr Gly Asp Asp Gly Gly Ala
    130                 135                 140
Ala Ala Ala Ala Ala Ala Ala Ser Ala Ser Arg Leu Ala Ser Ser
145                 150                 155                 160
Ser Ala Val Ser Arg Val Ser Ser Ala Val Ser Ala Leu Leu Ser Asn
                165                 170                 175
Gly Phe Ser Asp Val Asn Ser Leu Ser Asn Val Ile Ser Gly Leu Ser
                180                 185                 190
Ala Ser Val Ser Ser Ser Thr Pro Glu Leu Thr Gly Cys Glu Val Leu
                195                 200                 205
Val Glu Val Leu Leu Glu Val Val Ser Ala Leu Val His Ile Leu Asn
    210                 215                 220
Phe Ala Asp Ile Gly Asn Val Asn Ile Ser Ala Ser Gly Asp Ser Thr
225                 230                 235                 240
Ser Leu Val Gly Arg Thr Val Leu Glu Ala Phe Gly
                245                 250

<210> SEQ ID NO 56
<211> LENGTH: 197
<212> TYPE: PRT
<213> ORGANISM: Argiope trifasciata

<400> SEQUENCE: 56

Gly Ile Asn Val Asp Ser Gly Ser Val Gln Ser Asp Ile Ser Ser Ser
1               5                   10                  15
Ser Ser Phe Leu Ser Thr Ser Ser Ser Ala Ser Tyr Ser Gln Ala
                20                  25                  30
Ser Ala Ser Ser Ser Gly Ala Gly Tyr Thr Gly Pro Ser Gly Pro
            35                  40                  45
Ser Thr Gly Pro Ser Gly Tyr Pro Gly Pro Leu Ser Gly Gly Ala Ser
    50                  55                  60
Phe Gly Ser Gly Gln Ser Ser Phe Gly Gln Thr Ser Ala Phe Ser Ala
65                  70                  75                  80
Ser Gly Ala Gly Gln Ser Ala Gly Val Ser Val Ile Ser Ser Leu Asn
                85                  90                  95
Ser Pro Val Gly Leu Arg Ser Pro Ser Ala Ala Ser Arg Leu Ser Gln
                100                 105                 110
Leu Thr Ser Ser Ile Thr Asn Ala Val Gly Ala Asn Gly Val Asp Ala
                115                 120                 125
Asn Ser Leu Ala Arg Ser Leu Gln Ser Ser Phe Ser Ala Leu Arg Ser
    130                 135                 140
Ser Gly Met Ser Ser Ser Asp Ala Lys Ile Glu Val Leu Leu Glu Thr
145                 150                 155                 160
Ile Val Gly Leu Leu Gln Leu Leu Ser Asn Thr Gln Val Arg Gly Val
                165                 170                 175
Asn Pro Ala Thr Ala Ser Ser Val Ala Asn Ser Ala Ala Arg Ser Phe
    180                 185                 190
```

-continued

```
Glu Leu Val Leu Ala
        195

<210> SEQ ID NO 57
<211> LENGTH: 200
<212> TYPE: PRT
<213> ORGANISM: Argiope trifasciata

<400> SEQUENCE: 57

Ser Ser Val Val Gln Arg Ala Ala Gln Ser Leu Ala Ser Thr Leu Gly
1               5                   10                  15

Val Asp Gly Asn Asn Leu Ala Arg Phe Ala Val Gln Ala Val Ser Arg
            20                  25                  30

Leu Pro Ala Gly Ser Asp Thr Ser Ala Tyr Ala Gln Ala Phe Ser Ser
        35                  40                  45

Ala Leu Phe Asn Ala Gly Val Leu Asn Ala Ser Asn Ile Asp Thr Leu
    50                  55                  60

Gly Ser Arg Val Leu Ser Ala Leu Leu Asn Gly Val Ser Ser Ala Ala
65                  70                  75                  80

Gln Gly Leu Gly Ile Asn Val Asp Ser Gly Ser Val Gln Ser Asp Ile
                85                  90                  95

Ser Ser Ser Ser Ser Phe Leu Ser Thr Ser Ser Ser Ser Ala Ser Tyr
            100                 105                 110

Ser Gln Ala Ser Ala Ser Ser Thr Ser Gly Ala Gly Tyr Thr Gly Pro
        115                 120                 125

Ser Gly Pro Ser Thr Gly Pro Ser Gly Tyr Pro Gly Pro Leu Gly Gly
    130                 135                 140

Gly Ala Pro Phe Gly Gln Ser Gly Phe Gly Gly Ser Ala Gly Pro Gln
145                 150                 155                 160

Gly Gly Phe Gly Ala Thr Gly Gly Ala Ser Ala Gly Leu Ile Ser Arg
                165                 170                 175

Val Ala Asn Ala Leu Ala Asn Thr Ser Thr Leu Arg Thr Val Leu Arg
            180                 185                 190

Thr Gly Val Ser Gln Gln Ile Ala
        195                 200

<210> SEQ ID NO 58
<211> LENGTH: 20
<212> TYPE: DNA
<213> ORGANISM: Artificial Sequence
<220> FEATURE:
<221> NAME/KEY: misc_feature
<222> LOCATION: (3, 6, 18)
<223> OTHER INFORMATION: w = a or t
<220> FEATURE:
<221> NAME/KEY: misc_feature
<222> LOCATION: (5)
<223> OTHER INFORMATION: y = c or t
<220> FEATURE:
<221> NAME/KEY: misc_feature
<222> LOCATION: (9)
<223> OTHER INFORMATION: n = a or c or g or t

<400> SEQUENCE: 58
ccwaywccnc catatccwcc                                              20

<210> SEQ ID NO 59
<211> LENGTH: 26
<212> TYPE: DNA
<213> ORGANISM: Artificial Sequence
<220> FEATURE:
<221> NAME/KEY: misc_feature
```

```
<222> LOCATION: (3, 6, 9, 15, 18, 21, 24)
<223> OTHER INFORMATION: w = a or t
<220> FEATURE:
<221> NAME/KEY: misc_feature
<222> LOCATION: (12, 13 , 14)
<223> OTHER INFORMATION: n = a or c or g or t

<400> SEQUENCE: 59
ccwccwggwc cnnnwccwcc wggwcc                                          26

<210> SEQ ID NO 60
<211> LENGTH: 23
<212> TYPE: DNA
<213> ORGANISM: Artificial Sequence
<220> FEATURE:
<221> NAME/KEY: misc_feature
<222> LOCATION: (3, 6, 15, 18, 21)
<223> OTHER INFORMATION: w = a or t

<400> SEQUENCE: 60
ccwggwcctt gttgwccwgg wcc                                             23

<210> SEQ ID NO 61
<211> LENGTH: 17
<212> TYPE: DNA
<213> ORGANISM: Artificial Sequence
<220> FEATURE:
<221> NAME/KEY: misc_feature
<222> LOCATION: (3, 6, 9, 12, 15)
<223> OTHER INFORMATION: d = a or g or t)

<400> SEQUENCE: 61
gcdgcdgcdg cdgcdgc                                                    17

<210> SEQ ID NO 62
<211> LENGTH: 20
<212> TYPE: DNA
<213> ORGANISM: Artificial Sequence
<220> FEATURE:
<221> NAME/KEY: misc_feature
<222> LOCATION: (3, 6, 9, 12, 15, 18)
<223> OTHER INFORMATION: w = a or t

<400> SEQUENCE: 62
ccwgcwccwg cwccwgcwcc                                                 20

<210> SEQ ID NO 63
<211> LENGTH: 20
<212> TYPE: DNA
<213> ORGANISM: Artificial Sequence
<220> FEATURE:
<221> NAME/KEY: misc_feature
<222> LOCATION: (6)
<223> OTHER INFORMATION: d = a or g or t

<400> SEQUENCE: 63
ccagadagac caggattact                                                 20

<210> SEQ ID NO 64
<211> LENGTH: 22
<212> TYPE: DNA
<213> ORGANISM: Artificial Sequence
<220> FEATURE:
<223> OTHER INFORMATION: Primer

<400> SEQUENCE: 64
ggtgctggac aaggaggata cg                                              22
```

<210> SEQ ID NO 65
<211> LENGTH: 25
<212> TYPE: DNA
<213> ORGANISM: Artificial Sequence
<220> FEATURE:
<223> OTHER INFORMATION: Primer

<400> SEQUENCE: 65
ggcttgataa actgattgac caacg                                       25

<210> SEQ ID NO 66
<211> LENGTH: 24
<212> TYPE: DNA
<213> ORGANISM: Artificial Sequence
<220> FEATURE:
<223> OTHER INFORMATION: Primer

<400> SEQUENCE: 66
cacagccaga gagaccagga ttgc                                        24

<210> SEQ ID NO 67
<211> LENGTH: 22
<212> TYPE: DNA
<213> ORGANISM: Artificial Sequence
<220> FEATURE:
<223> OTHER INFORMATION: Primer

<400> SEQUENCE: 67
ccaggaggat atggaccagg tc                                          22

<210> SEQ ID NO 68
<211> LENGTH: 22
<212> TYPE: DNA
<213> ORGANISM: Artificial Sequence
<220> FEATURE:
<223> OTHER INFORMATION: Primer

<400> SEQUENCE: 68
ccgacaactt gggcgaactg ag                                          22

<210> SEQ ID NO 69
<211> LENGTH: 20
<212> TYPE: DNA
<213> ORGANISM: Artificial Sequence
<220> FEATURE:
<223> OTHER INFORMATION: Primer

<400> SEQUENCE: 69
caaggatctg gacagcaagg                                             20

<210> SEQ ID NO 70
<211> LENGTH: 21
<212> TYPE: DNA
<213> ORGANISM: Artificial Sequence
<220> FEATURE:
<223> OTHER INFORMATION: Primer

<400> SEQUENCE: 70
caacaaggac caggaagtgg c                                           21

<210> SEQ ID NO 71
<211> LENGTH: 20
<212> TYPE: DNA
<213> ORGANISM: Artificial Sequence
<220> FEATURE:
<221> NAME/KEY: misc_feature

```
<222> LOCATION: (8)
<223> OTHER INFORMATION: w = a or t

<400> SEQUENCE: 71
ccaaccawtt gcgcatactg                                          20

<210> SEQ ID NO 72
<211> LENGTH: 20
<212> TYPE: DNA
<213> ORGANISM: Artificial Sequence
<220> FEATURE:
<221> NAME/KEY: misc_feature
<222> LOCATION: (15)
<223> OTHER INFORMATION: y = c or t

<400> SEQUENCE: 72
gcttgagtta aagaytgacc                                          20

<210> SEQ ID NO 73
<211> LENGTH: 19
<212> TYPE: DNA
<213> ORGANISM: Artificial Sequence
<220> FEATURE:
<223> OTHER INFORMATION: Primer

<400> SEQUENCE: 73
gcaggaccag gaagttatg                                           19
```